(12) United States Patent
Ryan et al.

(10) Patent No.: US 11,071,596 B2
(45) Date of Patent: Jul. 27, 2021

(54) SYSTEMS AND METHODS FOR SENSORY AUGMENTATION IN MEDICAL PROCEDURES

(71) Applicant: Insight Medical Systems, Inc., Laguna Hills, CA (US)

(72) Inventors: Matthew William Ryan, Alisa Viejo, CA (US); Andrew Philip Hartman, Encinitas, CA (US); Nicholas van der Walt, Laguna Hills, CA (US); Jonathan Kirk Nielsen, Aliso Viejo, CA (US)

(73) Assignee: Insight Medical Systems, Inc., Austin, TX (US)

(*) Notice: Subject to any disclaimer, the term of this patent is extended or adjusted under 35 U.S.C. 154(b) by 0 days.

(21) Appl. No.: 16/786,938

(22) Filed: Feb. 10, 2020

(65) Prior Publication Data

US 2020/0197107 A1 Jun. 25, 2020

Related U.S. Application Data

(63) Continuation-in-part of application No. PCT/US2018/018330, filed on Feb. 15, 2018, which
(Continued)

(51) Int. Cl.
*A61B 34/00* (2016.01)
*A61B 90/00* (2016.01)
(Continued)

(52) U.S. Cl.
CPC ............ *A61B 34/25* (2016.02); *A61B 90/361* (2016.02); *G02B 27/0093* (2013.01);
(Continued)

(58) Field of Classification Search
CPC ....... A61B 34/00; A61B 34/25; A61B 90/361; A61B 2017/00216; A61B 2090/365;
(Continued)

(56) References Cited

U.S. PATENT DOCUMENTS 4,462,119 A * 7/1984 Rudd ............... A42B 3/221
2/424
5,351,339 A * 10/1994 Reuber ............ A42B 3/226
2/15
(Continued)

FOREIGN PATENT DOCUMENTS

WO 2005088539 A2 9/2005
WO 2006079211 A1 8/2006
(Continued)

OTHER PUBLICATIONS

Biocca ["Attention Issues in Spatial Information Systems: Directing Mobile Users' Visual Attention Using Augmented Reality" Journal of Management Information Systems vol. 23, 2007—Issue 4] (Year: 2007).*
(Continued)

*Primary Examiner* — Oommen Jacob
(74) *Attorney, Agent, or Firm* — Aurora Consulting LLC; Ashley Sloat

(57) ABSTRACT

Described here are self-contained surgical navigation systems which include a head-worn display device to be worn by a user during surgery. The system includes a display generator for generating a visual display on the display device, and a sensor suite having at least one tracking camera. The system further includes a support module including: a user-replaceable, modular battery that is reversibly insertable into a housing of the support module, and a processor unit configured to receive data from the sensor suite and calculate a position and an orientation of at least one marker. The support module is electrically coupled to
(Continued)

the head-worn display device to provide power and data to the head-worn display device. The display device and the support module together comprise the entire sensing and computing capability of the system, without requiring external sensors, cameras, computers, or other electrical equipment.

17 Claims, 47 Drawing Sheets

Related U.S. Application Data is a continuation-in-part of application No. 15/674,749, filed on Aug. 11, 2017, now abandoned, which is a continuation-in-part of application No. PCT/US2017/046438, filed on Aug. 11, 2017.

(60) Provisional application No. 62/375,483, filed on Aug. 16, 2016.

(51) Int. Cl.
| | |
|---|---|
| G02B 27/01 | (2006.01) |
| G02B 27/00 | (2006.01) |
| G06T 19/00 | (2011.01) |
| G06T 7/73 | (2017.01) |
| A61B 17/00 | (2006.01) |

(52) U.S. Cl.
CPC ........... *G02B 27/0172* (2013.01); *G06T 7/74* (2017.01); *G06T 19/006* (2013.01); *A61B 2017/00216* (2013.01); *A61B 2090/363* (2016.02); *A61B 2090/365* (2016.02); *G02B 2027/0187* (2013.01)

(58) Field of Classification Search
CPC .... A61B 2034/2055; A61B 2034/2046; A61B 2034/2068–2072; A61B 2090/363–366; G06T 19/006; G06T 7/74; G02B 27/0172; G02B 27/0093; G02B 2027/0187
See application file for complete search history.

(56) References Cited

U.S. PATENT DOCUMENTS

| | | | | |
|---|---|---|---|---|
| 5,365,615 A | * | 11/1994 | Piszkin | A42B 3/22 2/10 |
| 5,667,291 A | * | 9/1997 | Caplan | F21V 21/084 362/105 |
| 5,870,166 A | * | 2/1999 | Chang | G02B 7/002 351/158 |
| 6,046,712 A | * | 4/2000 | Beller | G02B 27/017 345/7 |
| 6,340,234 B1 | * | 1/2002 | Brown, Jr. | A61F 9/06 362/105 |
| 6,900,777 B1 | | 5/2005 | Hebert et al. | |
| 7,190,378 B2 | * | 3/2007 | Sauer | G06F 3/011 345/156 |
| 7,599,789 B2 | * | 10/2009 | Leonard | G01C 21/005 382/103 |
| 7,725,949 B2 | * | 6/2010 | Landis | A61F 9/029 2/9 |
| 8,933,935 B2 | | 1/2015 | Yang et al. | |
| 9,414,633 B2 | * | 8/2016 | Giroux Bernier | A42B 3/042 |
| 9,448,758 B2 | * | 9/2016 | Georgeson | G06F 3/1454 |
| 10,013,808 B2 | | 7/2018 | Jones et al. | |
| 10,016,243 B2 | | 7/2018 | Esterberg | |
| 10,134,166 B2 | | 11/2018 | Benishti et al. | |
| 10,194,990 B2 | | 2/2019 | Amanatullah et al. | |
| 10,258,427 B2 | | 4/2019 | Saget et al. | |
| 10,368,947 B2 | | 8/2019 | Lang | |
| 2002/0075201 A1 | * | 6/2002 | Sauer | H04N 13/344 345/7 |
| 2002/0113756 A1 | * | 8/2002 | Tuceryan | H04N 13/376 345/8 |
| 2003/0063132 A1 | * | 4/2003 | Sauer | G06F 3/011 715/848 |
| 2004/0019274 A1 | | 1/2004 | Galloway, Jr. et al. | |
| 2004/0181149 A1 | | 9/2004 | Langlotz | |
| 2004/0215057 A1 | * | 10/2004 | Wellman | A61B 1/00048 600/114 |
| 2005/0047117 A1 | * | 3/2005 | Scholl | A61F 9/06 362/106 |
| 2005/0203380 A1 | | 9/2005 | Sauer et al. | |
| 2005/0281465 A1 | | 12/2005 | Marquart | |
| 2006/0004280 A1 | * | 1/2006 | Kotake | G06T 7/73 600/414 |
| 2006/0043296 A1 | * | 3/2006 | Mian | G01J 5/0846 250/330 |
| 2006/0133069 A1 | * | 6/2006 | Clupper | F21L 14/00 362/106 |
| 2006/0264740 A1 | * | 11/2006 | Van Vaals | A61B 5/055 600/414 |
| 2007/0028372 A1 | * | 2/2007 | VanDerWoude | A41D 13/1153 2/457 |
| 2007/0273610 A1 | * | 11/2007 | Baillot | G08G 5/0069 345/8 |
| 2008/0202509 A1 | | 8/2008 | Dillon | |
| 2009/0227852 A1 | * | 9/2009 | Glaser | A42B 3/0433 600/324 |
| 2011/0105851 A1 | * | 5/2011 | Horvath | H05B 47/28 600/249 |
| 2011/0170280 A1 | * | 7/2011 | Soto | A42B 3/044 362/105 |
| 2012/0317706 A1 | * | 12/2012 | Lebel | F41H 1/08 2/422 |
| 2013/0123801 A1 | | 5/2013 | Umasuthan et al. | |
| 2013/0150863 A1 | | 6/2013 | Baumgartner | |
| 2013/0237811 A1 | * | 9/2013 | Mihailescu | A61B 90/361 600/424 |
| 2014/0022283 A1 | | 1/2014 | Chan et al. | |
| 2014/0028856 A1 | * | 1/2014 | Ehrlich | F41G 3/12 348/169 |
| 2014/0031668 A1 | | 1/2014 | Mobasser | |
| 2014/0369584 A1 | | 12/2014 | Fan et al. | |
| 2015/0145887 A1 | * | 5/2015 | Forutanpour | G02B 27/017 345/633 |
| 2015/0205388 A1 | * | 7/2015 | Osterhout | G06F 3/042 345/179 |
| 2015/0297177 A1 | * | 10/2015 | Boctor | A61B 34/30 600/437 |
| 2015/0356772 A1 | * | 12/2015 | Osterhout | G02B 27/0179 345/633 |
| 2016/0000518 A1 | * | 1/2016 | Thoranaghatte | G06F 3/04815 703/11 |
| 2016/0183841 A1 | | 6/2016 | Duindam et al. | |
| 2016/0191887 A1 | | 6/2016 | Casas | |
| 2016/0206379 A1 | | 7/2016 | Flett et al. | |
| 2016/0324580 A1 | | 11/2016 | Esterberg | |
| 2017/0011555 A1 | * | 1/2017 | Li | G06T 1/60 |
| 2017/0053545 A1 | * | 2/2017 | Yang | G06F 3/005 |
| 2017/0178375 A1 | * | 6/2017 | Benishti | G02B 27/0172 |
| 2017/0296292 A1 | | 10/2017 | Mahmood et al. | |
| 2017/0312032 A1 | | 11/2017 | Amanatullah et al. | |
| 2017/0322410 A1 | * | 11/2017 | Watson | G02B 21/365 |
| 2018/0012416 A1 | | 1/2018 | Jones et al. | |
| 2018/0032130 A1 | | 2/2018 | Meglan | |
| 2018/0081179 A1 | * | 3/2018 | Samec | G01J 3/0248 |
| 2018/0168740 A1 | | 6/2018 | Ryan et al. | |
| 2018/0185100 A1 | | 7/2018 | Weinstein et al. | |
| 2018/0256256 A1 | | 9/2018 | May et al. | |
| 2018/0286136 A1 | | 10/2018 | Jones et al. | |
| 2018/0344309 A1 | | 12/2018 | Nawana et al. | |
| 2018/0344412 A1 | | 12/2018 | Esterberg | |
| 2019/0011709 A1 | | 1/2019 | Yadav et al. | |
| 2019/0094981 A1 | | 3/2019 | Bradski et al. | |
| 2019/0142520 A1 | | 5/2019 | VanDyken | |

(56) References Cited

U.S. PATENT DOCUMENTS

| 2019/0192230 | A1 | 6/2019 | Siemionow et al. |
| 2019/0192232 | A1 | 6/2019 | Altmann et al. |
| 2020/0197107 | A1* | 6/2020 | Ryan .................... G06T 19/006 |

FOREIGN PATENT DOCUMENTS

| WO | 2015192117 A1 | 12/2015 |
| WO | 2017185170 A1 | 11/2017 |
| WO | 2018063528 A1 | 4/2018 |

OTHER PUBLICATIONS

Lu ["Attributes of Subtle Cues for Facilitating Visual Search in Augmented Reality" IEEE Transactions on Visualization and Computer Graphics, vol. 20, No. 3, Mar. 2014] (Year: 2014).*

Bajura ["Dynamic Registration Correction in Video Based Augmented Reality" Virtual Reality 1995 ] (Year: 1995).*

Anonymous: "Simultaneous Localization and mapping—Wikipedia," dated Jul. 25, 2016, https://en.wikipedia.org/w/index.php?title=Simultaneous localization-and-mapping &oldid=731478358- [retrieved on Oct. 23, 2017].

International Search Report and Written Opinion dated May 23, 2018 re PCT/US2018/018330 filed Feb. 15, 2018 (19 pages).

Baker et al. article entitled "The Emergence of Augmented Reality in Orthopaedic Surgery and Education," The Orthopaedic Journal at Harvard Medical School, vol. 16 Jun. 2015.

Wang et al. article entitled "Augmented Reality Navigation With Automatic Marker-Free Image Registration Using 3-D Image Overlay for Dental Surgery," IEEE Transactions on Biomedical Engineering, vol. 61, No. 4, Apr. 2014.

He et al. article entitled "An Inertial and Optical Sensor Fusion Approach for Six Degree-of-Freedom Pose Estimation," Sensors 2015, 15, 16448-16465; doi:10.3390/s150716448, ISSN 1424-8220 www.mdpi.com/journal/sensor.

Niikou et al. article entitled "Augmented Reality Imaging Technology for Orthopaedic Surgery," Operative Techniques in Orthopaedics, vol. 10, No. 1 Jan. 2000: pp. 82-88.

Sadda et al. article entitled "Surgical Navigation with a head-Mounted Tracking System and Display," Medicine Meets Virtual Reality 20, J.D. Westwood et al. (Eds.), IOS Press, 2013.

Wikipedia article entitled "Mixed Reality," dated Jun. 16, 2016 retrieved from Internet on Oct. 23, 2017.

Partial International Search and Provisional Opinion re PCT/US2017/046438 (13 pages).

* cited by examiner

SYSTEMS AND METHODS FOR SENSORY AUGMENTATION IN MEDICAL PROCEDURES

CROSS-REFERENCE TO RELATED APPLICATIONS

This application is a continuation-in-part of Patent Cooperation Treaty Application No. PCT/US2018/18330 filed Feb. 15, 2018; which is a continuation-in-part of U.S. application Ser. No. 15/674,749 filed Aug. 11, 2017 and Patent Cooperation Treaty Application No. PCT/US2017/046438 filed Aug. 11, 2017, both of which claim the priority benefit of U.S. Provisional Application Ser. No. 62/375,483 filed on Aug. 16, 2016; the contents of each of which are incorporated by reference in their entireties for all purposes.

FIELD OF INVENTION

The present invention relates to novel visualization and sensory augmentation devices, systems, methods, and apparatuses for positioning, localization, and situational awareness during medical procedures including, but not limited to, surgical, diagnostic, therapeutic, and anesthetic procedures.

BACKGROUND INFORMATION

Current medical procedures are typically performed by a surgeon or medical professional with little or no assistance outside of the required tools to effect changes on the patient. For example, an orthopedic surgeon may have some measurement tools (e.g., rulers or similar) and cutting tools (e.g., saws or drills), but visual, audible, and/or tactile inputs to the surgeon are not assisted. In other words, the surgeon sees nothing but what he or she is operating on, hears nothing but the normal communications from other participants in the operating room, and feels nothing outside of the normal feedback from grasping tools or other items of interest in the procedure. Alternatively, large console type navigation or robotic systems are utilized in which the display and cameras are located outside the sterile field away from the surgeon. These require the surgeon to repeatedly shift his or her gaze between the surgical site and the two-dimensional display. Also, the remote location of the cameras introduces line-of-sight issues when drapes, personnel, and/or instruments obstruct the camera's view of the markers in the sterile field, and the vantage point of the camera does not lend itself to imaging within the wound. Anatomic registrations are typically conducted using a stylus with markers to probe in such a way that the markers are visible to the cameras.

SUMMARY OF INVENTION

The present invention provides projection of feedback necessary for the procedure(s) visually into the user's field of view that does not require an unnatural motion or turning of the user's head to view an external screen. The augmented or virtual display manifests to the user as a natural extension or enhancement of the user's visual perception. Further, sensors and cameras located in the headpiece of the user have the same vantage point as the user, which minimizes line of sight obscuration issues associated with external cameras. 3D mapping of anatomic surfaces and features with the present invention and matching them to models from pre-operative scans are faster and represent a more accurate way to register the anatomy during surgery than current stylus point cloud approaches.

The present invention comprises a novel sensory enhancement device or apparatus generally consisting of at least one augmentation for the user's visual, auditory, or tactile senses that assists in the conduct of medical procedures. Visual assistance can be provided in the form of real time visual overlays on the user's field of view in the form of augmented reality or as a replacement of the visual scene in the form of virtual reality. Auditory assistance can be provided in the form of simple beeps and tones or more complex sounds like speech and instruction. Tactile assistance can be provided in the form of simple warning haptic feedback or more complex haptic generation with the goal of guiding the user. In the preferred embodiments, the visual (augmented or virtual) assistance will be supplemented by audio or tactile or both audio and tactile feedback.

The present invention provides a mixed reality surgical navigation system comprising: a head-worn display device (e.g., headset or the like), to be worn by a user (e.g., surgeon) during surgery, comprising a processor unit, a display generator, a sensor suite having at least one tracking camera; and at least one visual marker trackable by the camera and fixedly attached to a surgical tool; wherein the processing unit maps three-dimensional surfaces of partially exposed surfaces of an anatomical object of interest with data received from the sensor suite; the processing unit establishes a reference frame for the anatomical object by matching the three dimensional surfaces to a three dimensional model of the anatomical object; the processing unit tracks a six-degree of freedom pose (comprised of location and orientation) of the surgical tool with data received from the sensor suite; the processing unit communicates with the display to provide a mixed reality user interface comprising stereoscopic virtual images of desired features of the surgical tool and desired features of the anatomical object in the user's field of view.

The present invention further provides a method of using a mixed reality surgical navigation system for a medical procedure comprising: (a) providing a mixed reality surgical navigation system comprising (i) a head-worn display device comprising a processor unit, a display, a sensor suite having at least one tracking camera; and (ii) at least one visual marker trackable by the camera; (b) attaching the display device to a user's head; (c) providing a surgical tool having the marker; (d) scanning an anatomical object of interest with the sensor suite to obtain data of three-dimensional surfaces of desired features of the anatomical object; (e) transmitting the data of the three-dimensional surfaces to the processor unit for registration of a virtual three-dimensional model of the desired features of the anatomical object; (f) tracking the surgical tool with a six-degree of freedom pose with the sensor suite to obtain data for transmission to the processor unit; and (g) displaying a mixed reality user interface comprising stereoscopic virtual images of the features of the surgical tool and the features of the anatomical object in the user's field of view.

The present invention further provides a mixed reality user interface for a surgical navigation system comprising: stereoscopic virtual images of desired features of a surgical tool and desired features of an anatomical object of interest in a user's field of view provided by a mixed reality surgical navigation system comprising: (i) a head-worn display device comprising a processor unit, a display, a sensor suite having at least one tracking camera; and (ii) at least one visual marker trackable by the camera; wherein the mixed reality user interface is obtained by the following processes:

(a) attaching the head-worn display device to a user's head; (b) providing a surgical tool having the marker; (c) scanning a desired anatomical object with the sensor suite to obtain data of three-dimensional surfaces of partially exposed surfaces of the anatomical object; (d) transmitting the data of the three-dimensional surfaces to the processor unit for registration of a virtual three-dimensional model of the features of the anatomical object; (e) tracking the surgical tool with a six-degree of freedom pose with the sensor suite to obtain data for transmission to the processor unit; and (f) displaying a mixed reality user interface comprising stereoscopic virtual images of the features of the surgical tool and the features of the anatomical object in the user's field of view.

The present invention further provides a method for tracking a probe during a surgical procedure. For example, the method may include: receiving two-dimensional images of an internal anatomy of a patient using an ultrasound transducer; tracking a position and an orientation of the ultrasound transducer; tracking a position and an orientation of the patient; combining the two-dimensional images of the patient with the position and the orientation of the ultrasound transducer relative to patient; reconstructing the two-dimensional images in a common reference frame using the position and the orientation of the ultrasound transducer and the position and the orientation of the patient to produce a three-dimensional image of the internal anatomy of the patient; tracking a position and an orientation of a probe; displaying an axis and a location of a tip of the probe relative to the three-dimensional image of the internal anatomy of the patient; and advancing the tip of the probe to a desired position based on the location relative to the internal anatomy of the patient. The method may further include receiving two-dimensional images of an outer anatomy or outer surface of the patient using one or more stereo cameras or tracking cameras or ultrasound transducers; and displaying the two-dimensional image of the outer anatomy with the reconstructed three-dimensional images. The method may be used to monitor position, advancement, retraction, etc. of a pin, needle, screw, injection apparatus, probe, etc. The method may be performed by any of the head-worn display devices and/or mixed reality surgical systems described elsewhere herein.

One aspect of the present disclosure is directed to self-contained, head-worn surgical navigation system. In some embodiments, the system includes: a display generator for generating a visual display on the display device, a sensor suite having at least one tracking camera, and a processor unit configured to receive data from the sensor suite and calculate a position and an orientation of at least two markers by: determining a position of a first marker of the at least two markers within a field of view of the at least one tracking camera, displaying a virtual guide to the user on the display device to direct the user to a position of a second marker of the at least two markers relative to the first marker, and determining the position of the second marker with the at least one tracking camera based on the direction from the virtual guide.

Another aspect of the present disclosure is directed to a self-contained surgical navigation system. In some embodiments, the system includes: a head-worn display device to be worn by a user during surgery includes: a display generator for generating a visual display on the display device, and a sensor suite having at least one tracking camera. The system includes a support module including: a user-replaceable, modular battery that is reversibly insertable into a housing of the support module, and a processor unit configured to receive data from the sensor suite and calculate a position and an orientation of at least one marker.

In any of the preceding embodiments, the system further includes one or more of: a face shield and a helmet, such that the display device is mounted to the face shield or helmet.

In any of the preceding embodiments, the system further includes the at least one marker affixed to an object of interest for tracking the object of interest. In some such embodiments, the at least one marker is outside of a field of view of the at least one tracking camera, such that the processor unit is further configured to: track an angle of the head of the user using one or more sensors of the sensor suite; calculate a relative position of the at least one marker based on a last known position of the at least one marker when the at least one marker was positioned in the field of view of the at least one tracking camera, wherein the last known position is relative to the angle of the head; and display a virtual guide to the user on the display device to direct the user to a position of the at least one marker.

In any of the preceding embodiments, the support module is electrically coupled to the head-worn display device to provide power and data to the head-worn display device.

In any of the preceding embodiments, the support module is worn on a body of the user on a location other than a head of the user.

In any of the preceding embodiments, the display device and the support module together comprise the entire sensing and computing capability of the system, without requiring external sensors, cameras, computers, or other electrical equipment.

In any of the preceding embodiments, the system further includes: at least two markers affixed to an object of interest for tracking the object of interest. The first marker is within a field of view of the at least one tracking camera and a second marker is outside of the field of view of the at least one tracking camera. In some such embodiments, the processor unit is further configured to: determine a position of the first marker within the field of view of the at least one tracking camera, display a virtual guide to the user on the display device to direct the user to a position of the second marker relative to the first marker, and determine the position of the second marker with the at least one tracking camera based on the direction from the virtual guide.

In any of the preceding embodiments, the system further includes acquiring an initial position of the first marker and the second marker; and when the second marker is not in the field of view of the at least one tracking camera, estimating the position of the second marker relative to the first marker based on the acquired initial position.

In any of the preceding embodiments, the system further includes acquiring an initial position of the first marker and the second marker relative to known anatomical landmarks; calculating a distance between the known anatomical landmarks; and when the second marker is not in the field of view of the at least one tracking camera, estimating the position of the second marker relative to the first marker based on the calculated distance.

In any of the preceding embodiments, the system further includes tracking a movement of the head of the user using one or more sensors in the sensor suite; and calculating the position of the second marker based on a last known position of the second marker when the second marker was within the field of view of the at least one tracking camera.

In any of the preceding embodiments, the system further includes at least two markers affixed to an object of interest for tracking the object of interest. In some such embodiments, one or both of the at least two markers is outside of the field of view of the at least one tracking camera, such that the processor unit is further configured to: display a virtual control between the at least two markers; display a user input control that is configured to be aligned with the virtual control based on user input; adjusting a position of the virtual control when the user turns its head to align the user input control with the virtual control; and tracking the at least two markers in the field of view of the at least one tracking camera when the at least two markers are both in the field of view of the at least one tracking camera.

In any of the preceding embodiments, the head-worn display device further comprises an infrared light.

In any of the preceding embodiments, the system further includes a visible light and an infrared light filter coupled to the visible light, such that the visible light is prevented from emitting infrared light when the infrared light filter is coupled to the visible light.

In any of the preceding embodiments, the system further includes a shroud comprising a plurality of sidewalls arranged around the infrared light and defining an aperture through which light from the infrared light is emitted, In any of the preceding embodiments, the at least one tracking camera, the visible light, and the infrared light are positioned behind a face shield when the head-worn display device is attached to a helmet.

In any of the preceding embodiments, the plurality of sidewalls is in contact with the face shield when the head-worn display device is attached to the helmet such that light emitted by the infrared light is prevented from being reflected into the at least one tracking camera and only passes through the face shield.

In any of the preceding embodiments, the system further includes the face shield and the helmet.

In any of the preceding embodiments, the housing of the support module further includes a base comprising a circuit board arranged for directing electrical power from the battery to the processor unit and the head-worn display device.

In any of the preceding embodiments, the housing of the support module further comprises a bracket configured to securely and reversibly restrain the battery and the processor unit when positioned in the bracket.

Another aspect of the present disclosure is directed to a self-contained surgical navigation system configured for use with a helmet and a face shield. In some embodiments, the system includes a head-worn display device to be worn by a user during surgery comprising: a display generator for generating a visual display on the display device, a sensor suite having at least one tracking camera, a visible light, an infrared light, and a processor unit configured to receive data from the sensor suite and calculate a position and an orientation of at least one marker.

In any of the preceding embodiments, the system further includes a shroud comprising a plurality of sidewalls arranged around the infrared light and defining an aperture through which light from the infrared light is emitted.

In any of the preceding embodiments, the at least one tracking camera, the visible light, and the infrared light are positioned behind a face shield when the head-worn display device is attached to a helmet.

In any of the preceding embodiments, the plurality of sidewalls is in contact with the face shield when the head-worn display device is attached to the helmet such that light emitted by the infrared light is prevented from being reflected into the at least one tracking camera and only passes through the face shield.

In any of the preceding embodiments, the system further includes an infrared light filter coupled to the visible light, such that the visible light is prevented from emitting infrared light when the infrared light filter is coupled to the visible light.

In any of the preceding embodiments, the system further includes at least two markers affixed to an object of interest for tracking the object of interest, wherein a first marker is within a field of view of the at least one tracking camera and a second marker is outside of the field of view of the at least one tracking camera. In some such embodiments, the processor unit is further configured to: determine a position of the first marker within the field of view of the at least one tracking camera, display a virtual guide to the user on the display device to direct the user to a position of the second marker relative to the first marker, and determine the position of the second marker with the at least one tracking camera based on the direction from the virtual guide.

In any of the preceding embodiments, the system further includes a support module comprising: a user-replaceable, modular battery that is reversibly insertable into a housing of the support module, and a processor unit configured to receive data from the sensor suite and calculate a position and an orientation of at least one marker.

In any of the preceding embodiments, the support module is electrically coupled to the head-worn display device to provide power and data to the head-worn display device.

In any of the preceding embodiments, the support module is worn on a body of the user on a location other than a head of the user.

In any of the preceding embodiments, the display device and the support module together comprise the entire sensing and computing capability of the system, without requiring external sensors, cameras, computers, or other electrical equipment.

In any of the preceding embodiments, the shroud has a monolithic construction.

In any of the preceding embodiments, a front surface coupled to the plurality of sidewalls is in contact with the face shield and has a radius of curvature that matches a radius of curvature of the face shield.

In any of the preceding embodiments, a front surface coupled to the plurality of sidewalls is in contact with the face shield and has a radius of curvature that approximately matches a radius of curvature of the face shield.

In any of the preceding embodiments, one or more of the plurality of sidewalls is angled 10 to 20 degrees relative to a central axis of the infrared light.

Another aspect of the present disclosure is directed to a self-contained surgical navigation system configured for use with a helmet and a face shield. In some embodiments, the system includes a head-worn display device to be worn by a user during surgery comprising: a display generator for generating a visual display on the display device, wherein the display device is mounted to one or more of: a surgical helmet and a face shield, and a sensor suite having at least one tracking camera.

In any of the preceding embodiments, the system further includes a support module comprising: a user-replaceable, modular battery that is reversibly insertable into a housing of the support module, and a processor unit.

In any of the preceding embodiments, the support module is electrically coupled to the head-worn display device to provide power and data to the head-worn display device.

In any of the preceding embodiments, the support module is worn on a body of the user on a location other than a head of the user.

In any of the preceding embodiments, the display device and the support module together comprise an entire sensing and computing capability of the system, without requiring external sensors, cameras, computers, or other electrical equipment.

In any of the preceding embodiments, the processor unit is configured to receive data from the sensor suite and calculate a position and an orientation of at least two markers by: determining a position of a first marker of the at least two markers within a field of view of the at least one tracking camera, displaying a virtual guide to the user on the display device to direct the user to a position of a second marker of the at least two markers relative to the first marker, and determining the position of the second marker with the at least one tracking camera based on the direction from the virtual guide.

BRIEF DESCRIPTION OF THE DRAWINGS

Some embodiments of the present invention are illustrated as an example and are not limited by the figures of the accompanying drawings, in which like references may indicate similar elements and in which.

DETAILED DESCRIPTION OF THE INVENTION

Figure 1:
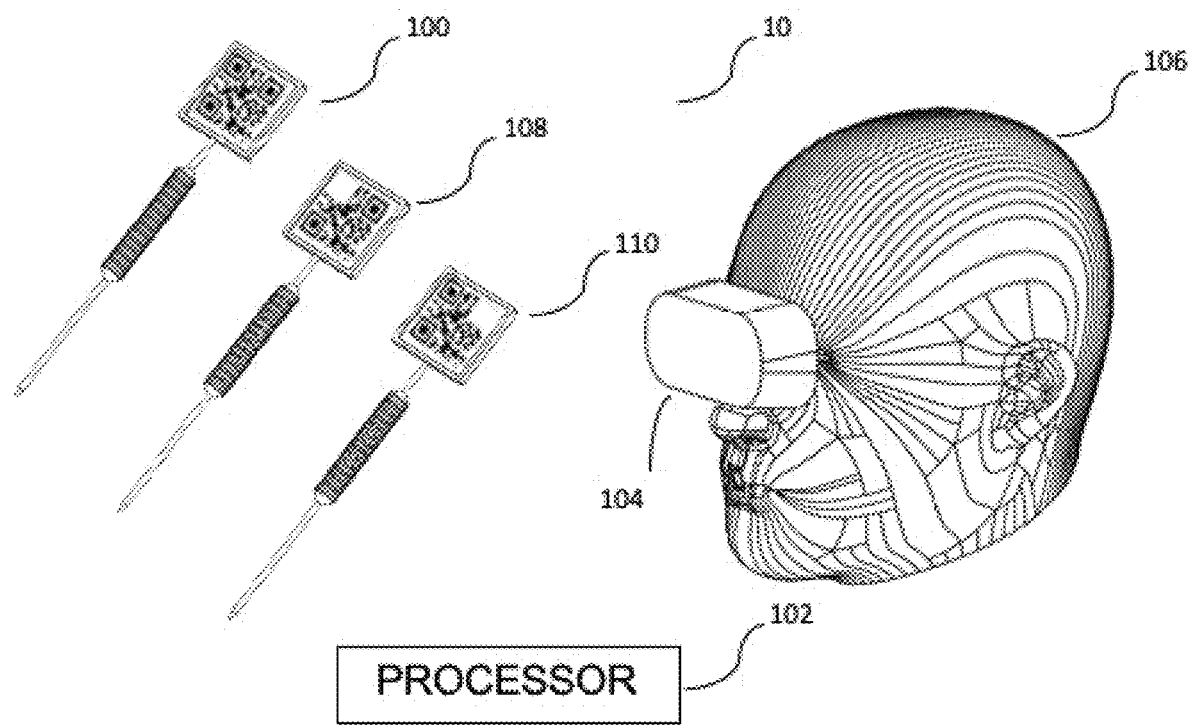
FIG. 1 is a diagrammatic depiction of an augmentation system in accordance with the principles of the present invention.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, and/or groups thereof.

Unless otherwise defined, all terms (including technical and scientific terms) used herein have the same meaning as commonly understood by one having ordinary skill in the art to which this invention belongs. It will be further understood that terms such as those defined in commonly used dictionaries should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and claims.

New sensory augmentation devices, apparatuses, and methods for providing data to assist medical procedures are discussed herein. In the following description, for purposes of explanation, numerous specific details are set forth in order to provide a thorough understanding of the present invention. It will be evident, however, to one skilled in the art that the present invention may be practiced without the specific details.

Further, it shall also be appreciated by one of skill in the art that any of the embodiments described herein can be combined with any other embodiments. For example, any combination of face shield, helmet, display device, etc. is contemplated herein. Further any processor unit executable method may be practiced with any combination of face shield, helmet, display device, etc. described herein or generally available in the art.

I. The Sensory Augmentation System

Referring to FIGS. 1, 2A-B, and 3, a sensory augmentation system 10 of the present invention is provided for use in medical procedures. The system 10 includes one or more visual markers (100, 108, 110), a processing unit 102, a sensor suite 210 having one or more tracking camera(s) 206, and a display device 104 having a display generator 204 that generates a visual display on the display device 104 for viewing by the user 106. The display device 104 is attached to a user 106 such that the display device 104 can augment his visual input. In one embodiment, the display device 104 is attached to the user's 106 head. Alternatively, the display device 104 is located separately from the user 106, while still augmenting the visual scene. In one embodiment, each of the markers (100, 108, and 110) is distinct and different from each other visually so they can be individually tracked by the camera(s) 206.

Figures 2A, 2B:
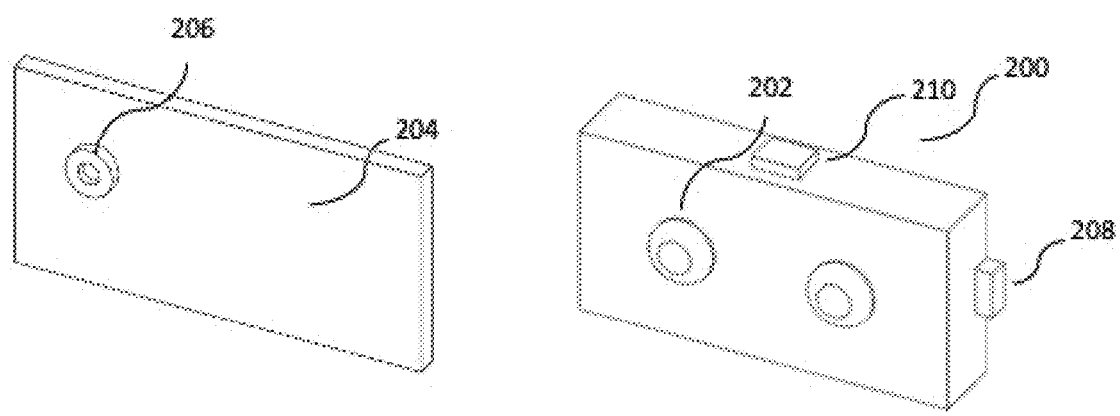
FIG. 2A shows a perspective front view of a diagrammatic depiction of a display device of the system of FIG. 1.
FIG. 2B shows a perspective back view of the display device of FIG. 2A.

Referring to FIGS. 2A-2B, another exemplary embodiment of the display device 104 includes a visor housing 200 having optics 202 that allow focusing of the display generator's 204 video display onto the user's 106 eyes. The sensor suite 210 is attached to or made part of the display device 104. The visor housing 200 includes an attachment mechanism 208 that allows attachment to the user's 106 head or face such that the alignment of the display device 104 to the user's 106 visual path is consistent and repeatable.

Figure 3:
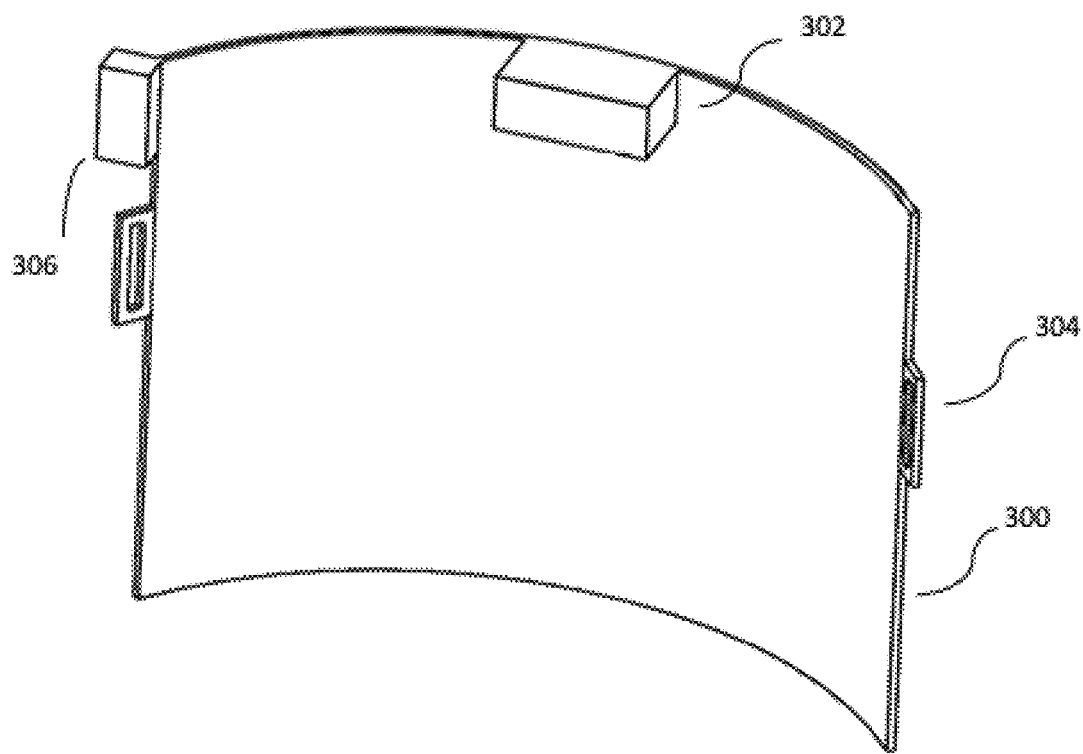
FIG. 3 is a diagrammatic depiction of another embodiment of the display device of the system of FIG. 1.

Referring to FIG. 3, another exemplary embodiment of the display device 104 includes a clear face shield 300 that allows a projection from the display generator 302 onto the shield 300 that overlays data and imagery within the visual path of the user's 106 eyes. The sensor suite 306 is attached to or made part of the display device, shown here as face shield 300. The face shield 300 further includes the attachment mechanism 304. The sensor suite 306 and the attachment mechanism 304 serve the same functions as the sensor suite 210 and the attachment mechanism 208 described above.

Figure 4:
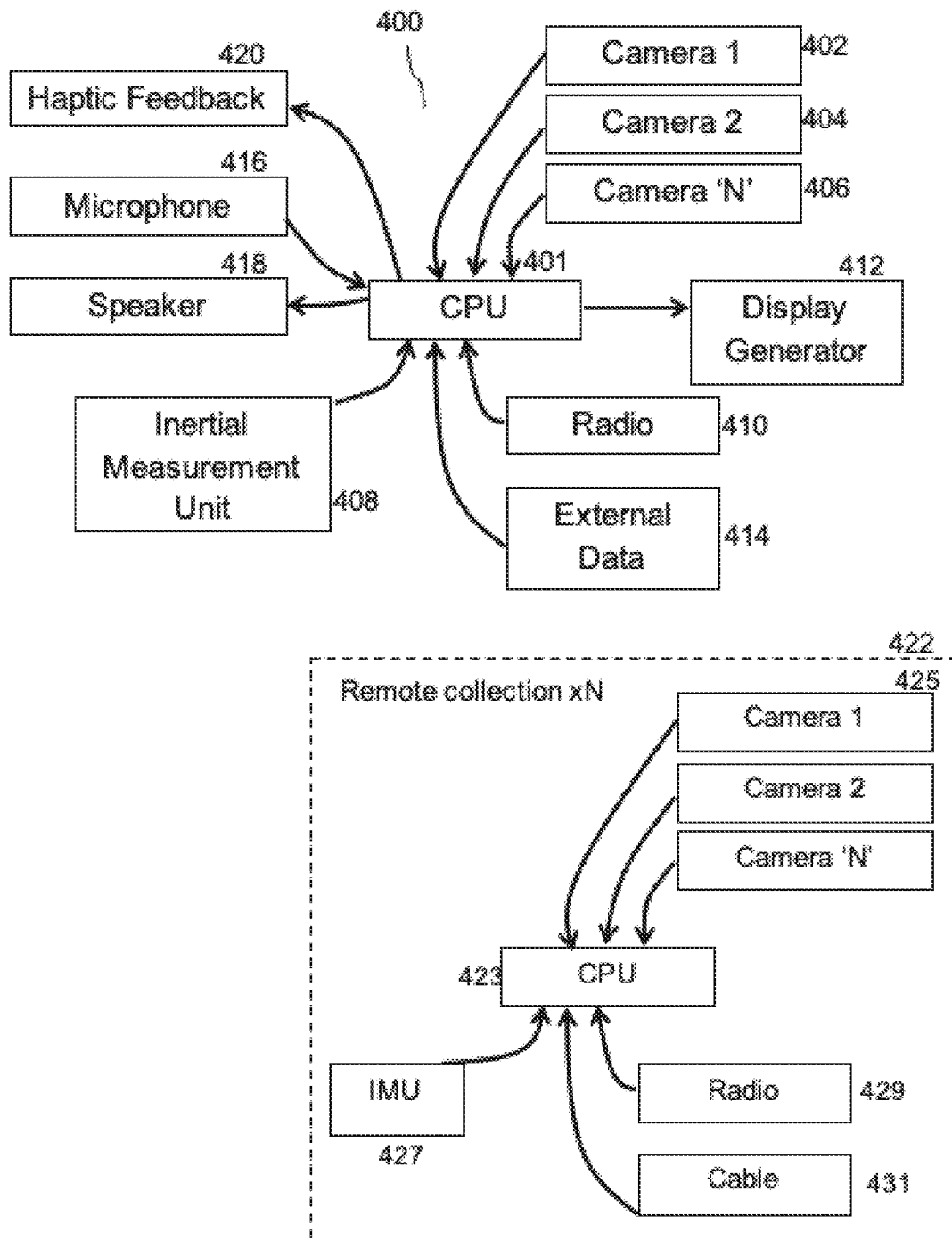
FIG. 4 is a schematic view of the electrical hardware configuration of system of FIG. 1.

Referring to FIG. 4 which shows the electronic hardware configuration of the system 10, the sensor suite (210, 306) not only includes one or more tracking cameras 402, 404, 406 (same as 206), it may optionally include an inertial measurement unit ("IMU") 408; a radio 410 for communication to other sensors or control units; a microphone 416 for voice activation of different display modes, including, but not limited to, removal of all displayed items for a clear field of view; one or more speakers 418 for audible alerts and other purposes; and haptic feedback 420 in the form of shaker motors, piezoelectric buzzers, or other embodiments. The IMU 408 provides added orientation and localization data for an object that is not visually based. The IMU 408 can be used for, but is not limited to, generation of simultaneous localization and mapping ("SLAM") data from camera tracking and IMU's 408 data to determine non-marker specific room features that assist in localization and generation of surface maps of the objects of interest. Furthermore, the sensor suite(s) (400, 210, and 306) includes external data 414 as relayed by wire, radio, or stored memory. External data 414 may optionally be in the forms of fluoroscopy imagery, computerized axial tomography ("CAT or CT") scans, positron emission tomography ("PET") scans, and/or magnetic resonance imaging ("MRI") data, or the like. Such data may be combined with other data collected by the sensor suite (400, 210, and 306) to create augmentation imagery.

During operation of the system 10, the display generator 412 (also shown as 204 and 302) and the processing unit 401 (also shown as 102) are in electronic communication with the components described above for the sensor suite (210, 306). The processing unit 401 is a central processing unit ("CPU") that controls display management and algorithm prosecution. Referring to FIG. 4, the system 10 may optionally include one or more remote sensor suites 422. These remote sensor suites 422 are physically located away from the display device 104. Each of these remote sensor suites 422 includes some or all of the components described above for the sensor suite (210, 306), for example cameras 425, IMU 427, radio 429, and cable 431 (e.g., for sharing data with system 400). It may also optionally include a separate and remote processing unit 423. The remote sensor suites 422 contribute data to the external data 414, which may be further processed by the processing unit 401 if desired. In another embodiment, the system 10 uses the remote suite(s) 422 to track not only the markers located in the field of regard, but also any marker(s) attached to the display unit 104 worn by the user 106, in order to localize the objects in the field of regard with respect to the user 106.

In one exemplary embodiment, the system 10 uses the sensor suite(s) (422, 210, 306) to create a three-dimensional point cloud of data representing objects in the workspace. These data can be used to create or match to already modeled objects for use in subsequent tracking, visualization, or playback at a later time.

Furthermore, the system 10 can optionally overlay imagery and masks using art-disclosed means in order to obscure objects in the field of view, including but not limited to, retractors or soft tissue around an exposure that are not the subject of the procedure to assist in highlighting the area, items, or regions of interest. In one embodiment, the external image can be projected with overlays in an augmented reality ("AR") mode. In another embodiment, the external image may be ignored, and only computer-generated graphics may be used to display data to the user 106 in a virtual reality ("VR") mode. VR mode is supported if the display device 104 or part thereof is made opaque to block the external visual data or if some other method is used to emphasize to the user 106 that concentration should be on the imagery and not the external imagery.

Other alternative embodiments of the display device 104 would include, but are not limited to, holographic or pseudo holographic display projections into the field of regard for the user 106. Furthermore, the display device may optionally provide art-disclosed means of eye tracking that allows determination of the optimal displayed imagery with respect to the user's 106 visual field of view.

The system 10 can optionally use algorithms to discriminate between items in the field of view to identify what constitutes objects of interest versus objects not important to the task at hand. This could include, but is not limited to, identifying bony landmarks on a hip acetabulum for use in comparison and merge with a pre-operative scan in spite of soft tissue and tools that are visible in the same field of regard.

Figure 5:
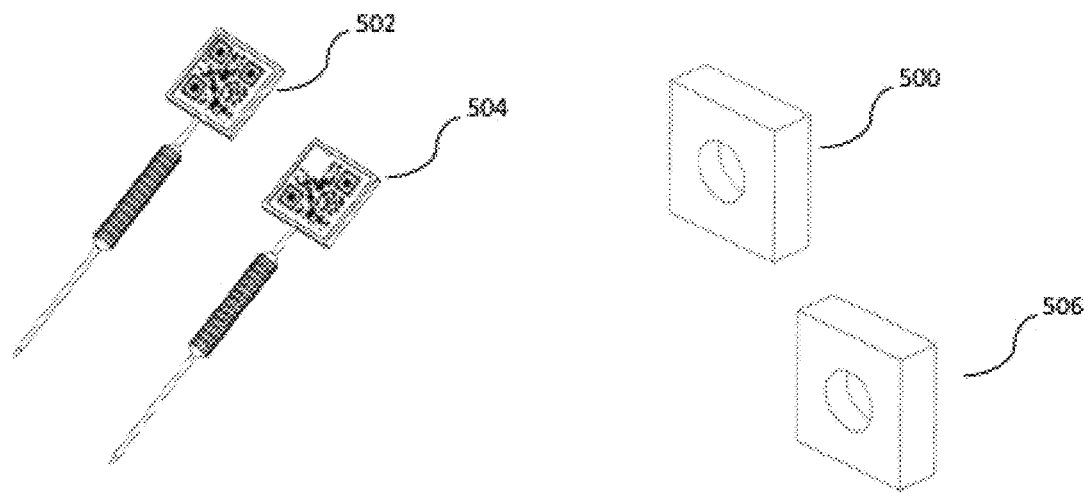
FIG. 5 is a diagrammatic depiction of markers and cameras of the system of FIG.

Referring to FIG. 5, the one or more cameras 500, 506 of the sensor suites (400, 422, 210, and 306) and the one or more visual markers 502, 504 are used to visually track a distinct object (e.g., a surgical tool, a desired location within an anatomical object, etc.) and determine altitude, location, orientation, and/or position relative to the user 106. In one embodiment, each of the one or more markers is distinct and different from each other visually. Standalone object recognition and machine vision technology can be used for marker recognition. Alternatively, the present invention also provides for assisted tracking using IMUS 408 on one or more objects of interest, including but not limited to, the markers 502, 504. Please note that the one or more cameras 500, 506 can be remotely located from the user 106 and provide additional data for tracking and localization.

Optimal filtering algorithms are optionally used to combine data from all available sources to provide the most accurate position and orientation data for items in the field of regard. This filter scheme will be able to accommodate events including, but not limited to, occlusions of the camera(s) field(s) of view, blood, tissue, or other organic temporary occlusions of the desired area of interest, head movement or other camera movement that move the camera(s) field(s) of view away from the area of interest, data drop outs, and battery/power supply depletion or other loss of equipment.

Referring to FIGS. 36A-B, 37A-B, 38A-B, and 39-41A-B, another exemplary embodiment of the display device 104 is a self-contained AR headset 3600. Previously available systems suffered from several technical problems or limitations. For example, previously available systems (1) required external sensors, cameras, computers, and/or power sources for full operation of a display device worn by the user; (2) were limited in their useful life during a procedure due to power source constraints (e.g., the power source was not easily or quickly replaceable during the procedure without experiencing data loss); and/or (3) the self-contained system was not adaptable to a variety of helmets, face shields, or hoods. The self-contained AR headsets described herein overcome these technical problems with technical solutions. As will be described in greater detail elsewhere herein, the self-contained AR headsets of the present disclosure include (1) all required sensor, cameras, computers, and/or power sources to fully execute a surgical procedure (i.e., no external electrical equipment is required); (2) a user replaceable power source or battery or a modular battery (i.e., not built into the support module but easily removable and separable from the support module), such that the battery is easily replaceable during a surgical procedure without tools, manipulating latches, or data loss so that the procedure can progress without delay; and (3) is readily adaptable to various surgical helmets, hoods, and face shields. Various embodiments of such self-contained AR headsets will now be described in greater detail.

The AR headset 3600 is used in various sterile surgical procedures (e.g., spinal fusion, hip and knee arthroplasty, etc.). The AR headset 3600 is clamped on the head of a surgeon 3602 (i.e., user 106) by adjusting a head strap 3604 by turning a thumb wheel 3606. A transparent protective face shield 3608 is optionally attached to the device 3600 by attachment to Velcro strips 3610. Alternatively, attachment may be via adhesive, magnetic, hooks, or other art-disclosed attachment means. A coupling feature 3612 is present for attachment of a surgical helmet 3700 both mechanically and electrically to the AR headset 3600. The surgical helmet 3700 is optionally connected to a surgical hood (not shown) that provides full body coverage for the surgeon 3602. Full body coverage is useful for certain surgical procedures such as hip and knee arthroplasty or the like. If the surgical helmet 3700 is to be attached to a surgical hood, then a fan draws air in through the surgical hood into air inlet 3702 and is circulated under the surgical hood and helmet to cool the surgeon 3602 and prevent fogging of the optical components. A chin piece 3704 spaces the helmet 3700 (and if applicable, the attached surgical hood) away from the surgeon's 3602 face. The location of the surgical helmet 3700 relative to the AR headset 3600 is designed to allow unobstructed view of the surgical site for the surgeon 3602 and all cameras and sensors. The surgical helmet 3700 includes the necessary features to attach to and interface with the surgical hood. A flexible cord 3706 connects the AR headset 3600 to a support module 3708, which can be worn on the surgeon's 3602 belt or any other location on the surgeon other than the surgeon's head. For example, the support module may be worn on a hip, on a lower back, on an upper back, on a shoulder (e.g., using a strap), on a chest, on a thigh, on a wrist, on a bicep, etc. A replaceable battery 3800 inserts into the support module 3708.

Figure 39:
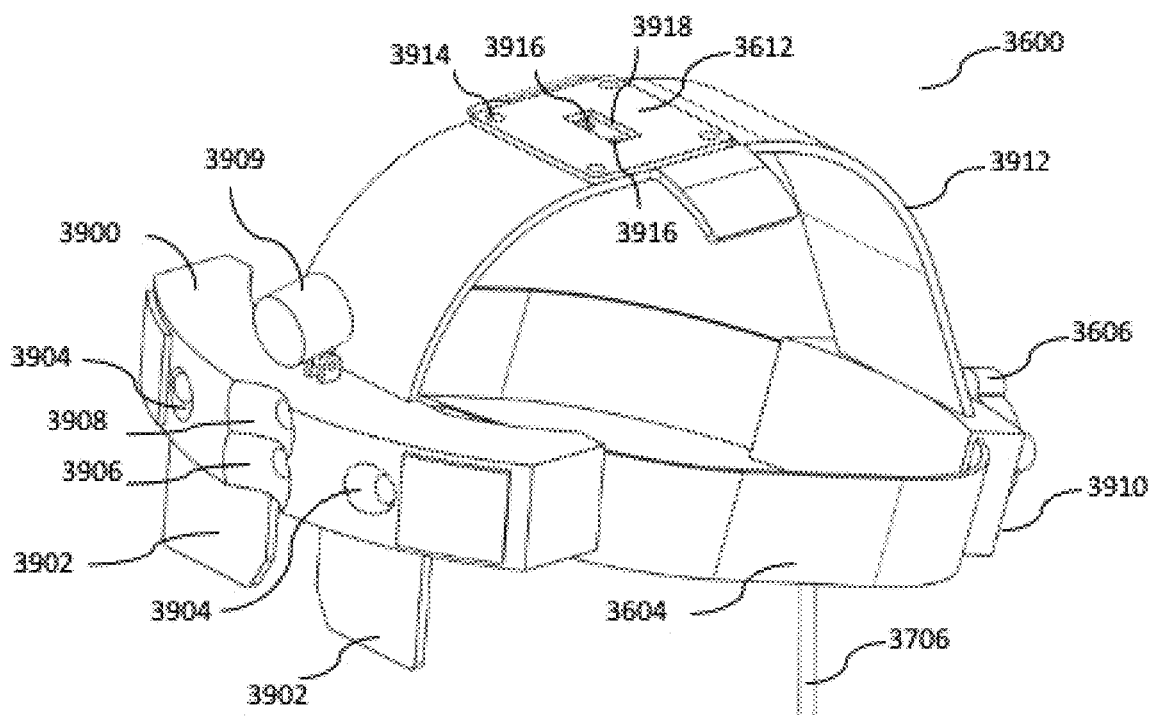
FIG. 39 shows a perspective front view of the AR headset shown in FIG. 36A.

Referring to FIG. 39, the AR headset 3600 includes a display section 3900 having a pair of see through optical displays 3902 for visual augmentation and one or more tracking cameras 3904 for performing tracking and stereoscopic imaging functions including two-dimensional and three-dimensional digital zoom functions. A depth sensor 3906 and a structured-light projector 3908 are included in the display section 3900. It is preferred that the depth sensor 3906 and the projector 3908 are located in the middle of the display section 3900. A surgical headlight 3909 is optionally mounted to the display section 3900 and may be electrically connected to the AR headset 3600 to allow its brightness to be controlled by the software of the AR headset 3600 including by voice command. This feature may be deployed, for example, to dim or switch off the surgical headlight when in mixed reality mode to allow better visualization of virtual content against a bright background. It may also be adjusted to optimize optical tracking which at times can be impaired by high contrast illumination of targets or by low ambient lighting. In another exemplary embodiment, the operating room lights may be controlled wirelessly by the software of the AR headset 3600 for the same reasons.

Figure 40:
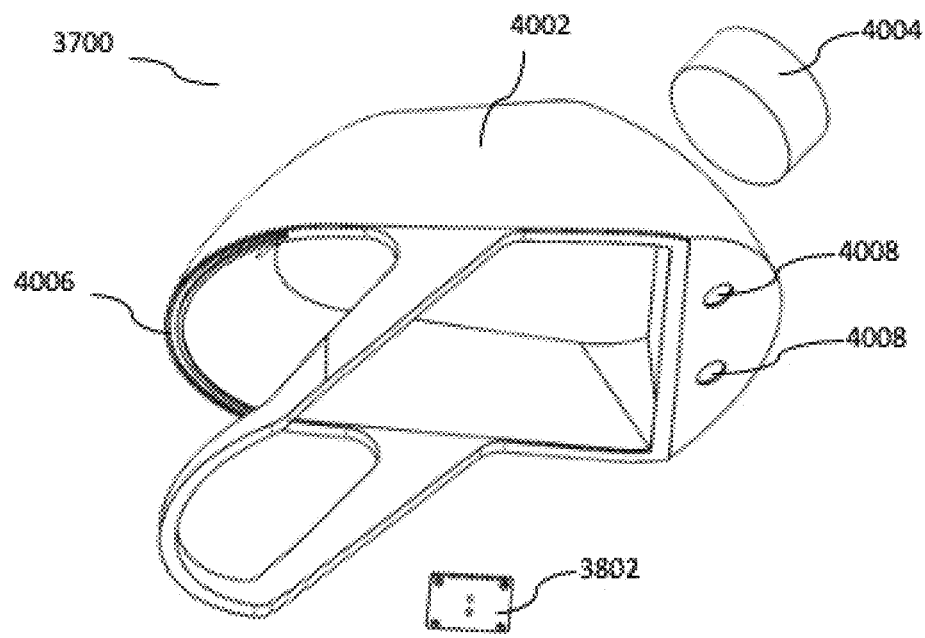
FIG. 40 is an exploded view of the surgical helmet shown in FIG. 37A.

Referring to FIGS. 39-40, the rear section 3910 of the AR headset 3600 may optionally contain the heat-generating and other components of the circuitry such as the microprocessor and internal battery. The arch-shaped bridge section 3912 and the head strap 3604 of the AR headset 3600 mechanically connect the rear section 3910 to the display section 3900. A portion of the bridge section 3912 is flexible to accommodate size adjustments. The bridge section 3912 may include wiring or a flexible circuit board to provide electrical connectivity between the display section 3900 and the rear section 3910. The bridge section 3912 includes the coupling feature 3612, which is a ferromagnetic plate with a plurality of locating holes 3914, which defines an aperture 3918 provides access to two electrical contacts 3916 for powering the fan of the surgical helmet 3700. In alternative embodiments, the coupling feature 3612 can be other art-disclosed means such as Velcro, latches or threaded fasteners or the like. The coupling feature 3612 may optionally include a vibration isolation mount to minimize transmission of mechanical noise from the fan of the surgical helmet 3700 to the AR headset 3600, which can be detrimental to tracking performance. The fan 4004 may be software controlled allowing it to be slowed or shut down to minimize the generation of mechanical noise. It may also be controlled by the surgeon 3602 using voice commands. A flexible cord 3706 connects the rear section 3910 to the support module 3708, shown in FIG. 38A.

Referring to FIG. 40, the surgical helmet 3700 includes a hollow shell 4002 into which a fan 4004 draws air which is exhausted through various vents in the shell to provide cooling air for the surgeon. A brim vent 4006 provides airflow over the visor of the surgical hood and rear vents 4008 provide cooling air to the rear including to the rear section 3910 of the AR headset 3600.

Figures 41A, 41B:
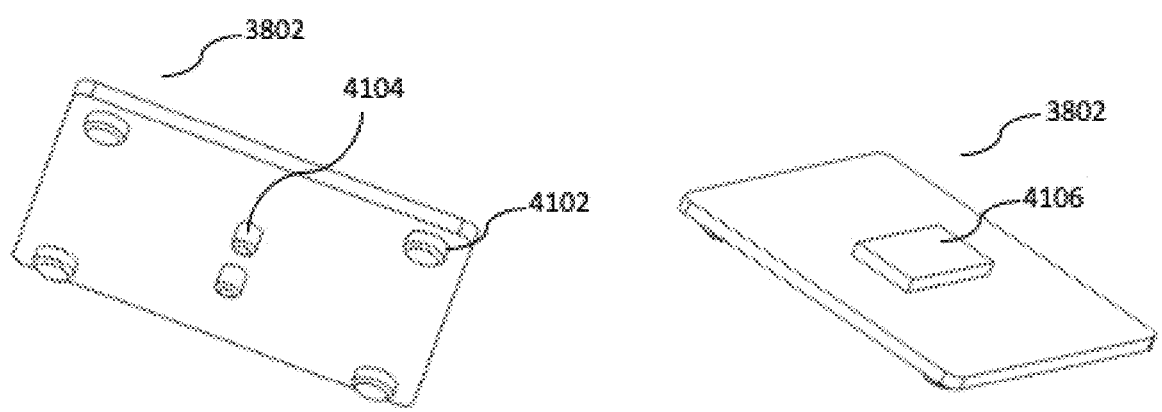
FIG. 41A is a perspective bottom view of the electromechanical coupling plate shown in FIG. 40.
FIG. 41B is a perspective top view of the electromechanical coupling plate shown in FIG. 40.

Referring to FIGS. 41A-B, the coupling plate 3802 includes a plurality of bosses 4102 for location with the holes 3914 in the AR headset 3600. The coupling plate 3802 also includes spring-loaded electrical contacts 4104, which connect with the electrical contacts 3916 of the AR headset 3600 to provide power to the fan 4004. The coupling plate 3802 further includes a magnet 4106, which provides a mechanical retention force between the coupling plate 3802 and the coupling feature 3612.

Figure 60:
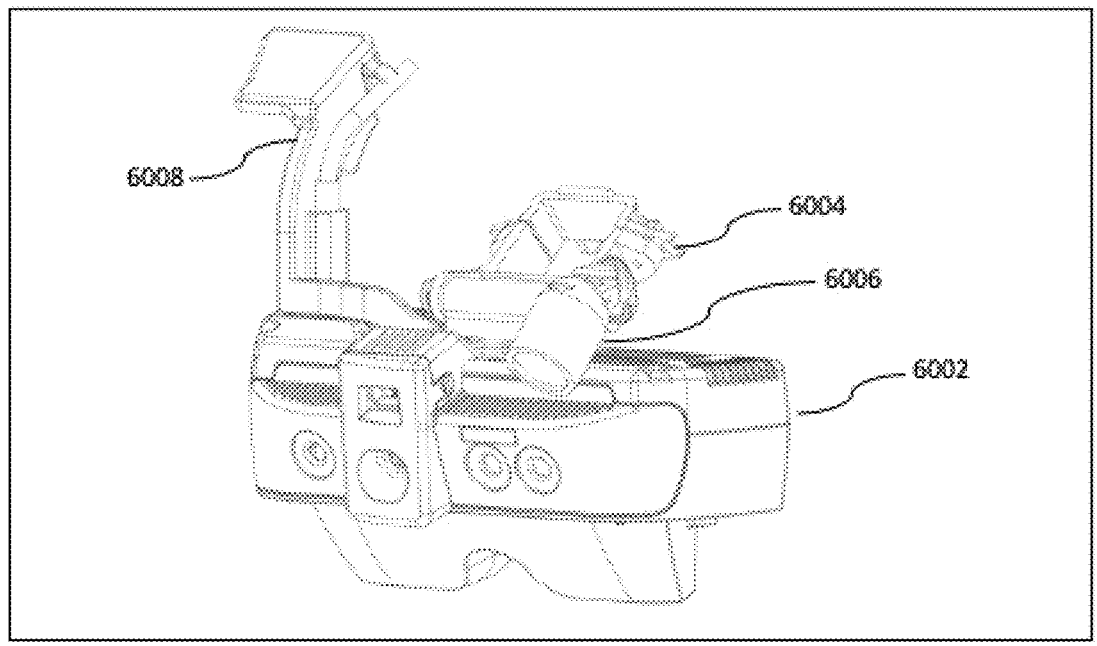
FIG. 60 is a diagrammatic depiction of an eyepiece with bracket.

Referring to FIG. 60, another exemplary embodiment of display device is in an eyepiece 6002, which includes a modular bracket 6004 configured to adapt to a headband or other support structure such as a surgical helmet 3700. A plurality of brackets 6004 can be interchanged to mount the eyepiece 6002 to different types of headgear. A focused spotlight or visible light 6006 is integrated to provide illumination to the procedural site and is mounted on a bracket allowing it to pivot up and down relative to the eyepiece so both the eyepiece display and the spotlight or visible light can be adjusted, independently of one another, to the correct angle for each user. In this embodiment, a handle 6008 is integrated to allow the user to easily adjust the position of display device even when worn under a surgical hood.

Figure 69:
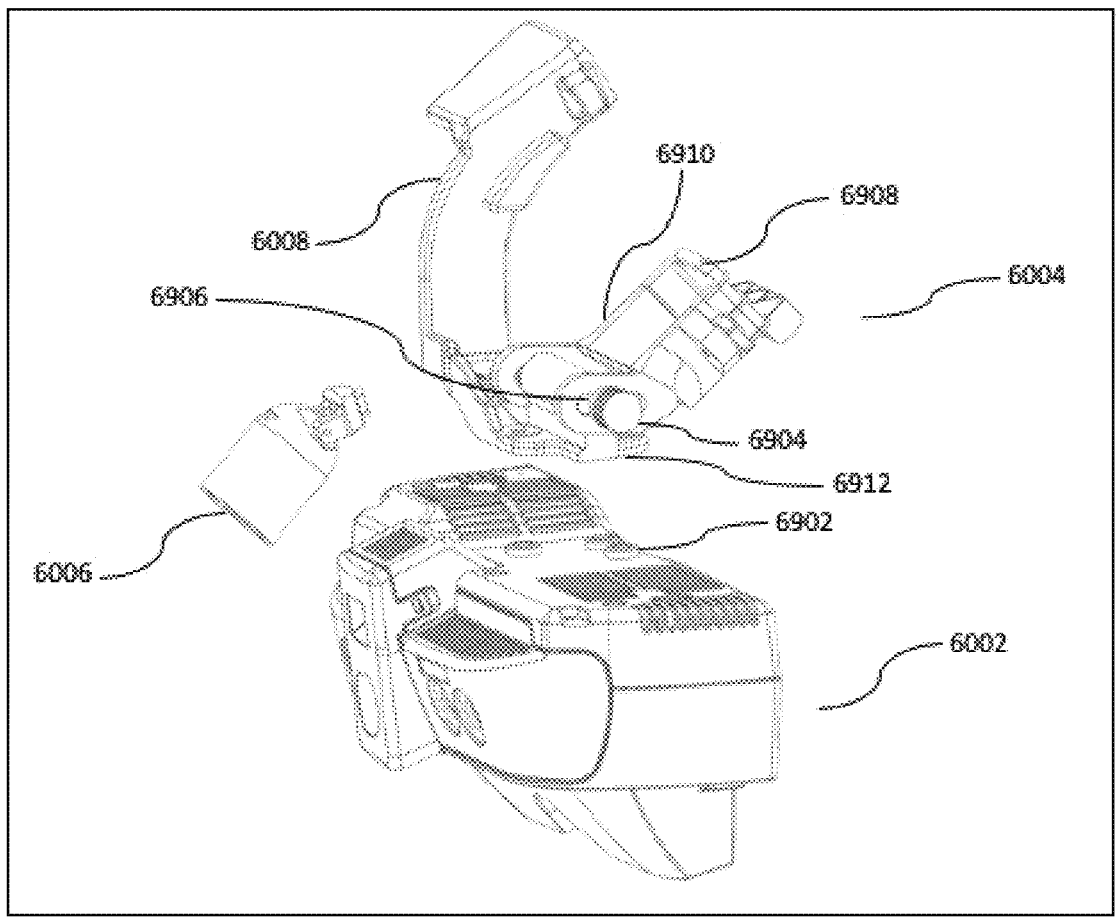
FIG. 69 shows an exploded view of the eyepiece and bracket depicted in FIG. 60.

In order for the display to be in focus, it must be positioned at the correct distance and angle to the user's eyes. Due to anatomic variations from user to user, it is beneficial to provide a means of adjusting the position and angle of the eyepiece 6002 for each user. Referring to FIG. 69, some additional features of eyepiece 6002 and bracket 6004 are shown which enable this adjustment. Bracket 6004 is mounted to eyepiece 6002 using one or more mounting features 6902, such as screws. Bracket 6004 comprises a lower bracket 6912 and an upper bracket 6910, which are connected by a locking knob 6904. Upper bracket 6910 further includes a clamp 6908 configured to rigidly connect it to a support structure such as a headband or surgical helmet. In this embodiment, the clamp 6908 is configured to mount the bracket 6904 to a Stryker Flyte surgical helmet. Lower bracket 6912 is rigidly coupled to eyepiece 6002. The upper bracket 6910 contains a slot 6906 interfacing with locking knob 6904 and allowing lower bracket 6912 and eyepiece 6002 to slide forward and backward when locking knob 6904 is loosened. Lower bracket 6912 can additionally pivot around locking knob 6904 to adjust the angle of eyepiece 6002. When worn under a surgical hood (not shown), the eyepiece 6002 may be difficult to reach and manipulate, since it is positioned behind a semi-rigid transparent face shield. In this embodiment, a handle 6008 is incorporated into lower bracket 6912 to enable the user to adjust the position and angle of eyepiece 6002 when worn under a hood.

Figure 71:
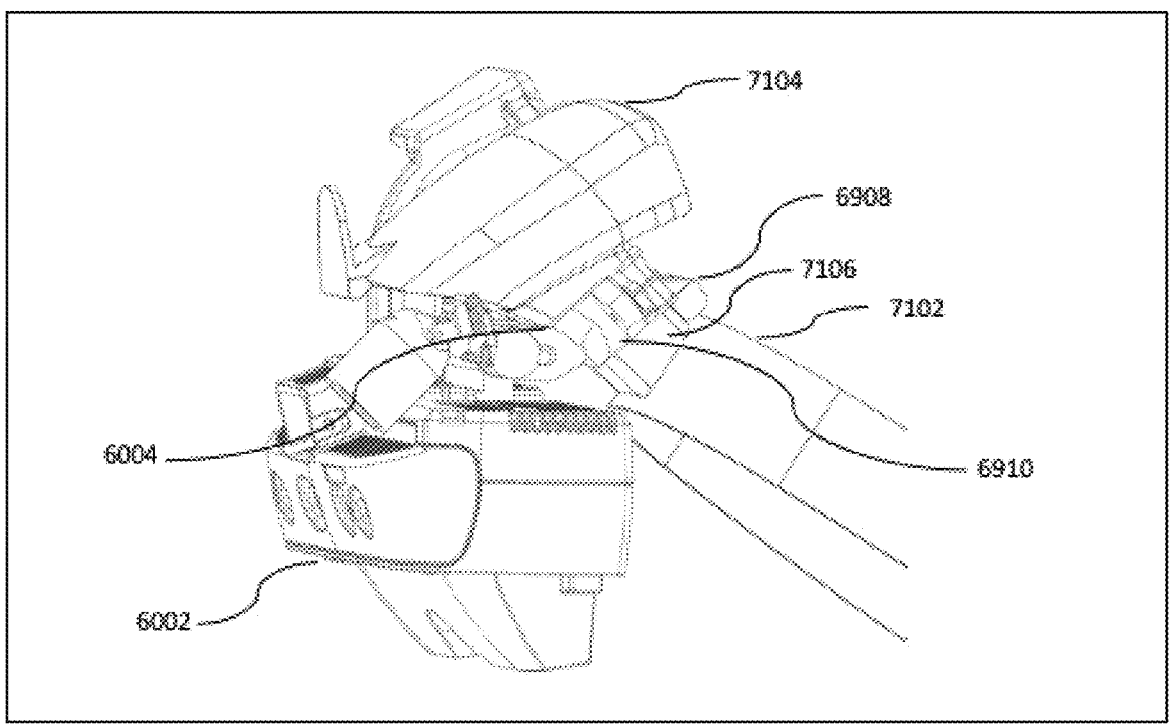
FIG. 71 shows the eyepiece and bracket depicted in FIG. 60 mounted in a surgical helmet.

Referring to FIG. 71, the eyepiece 6002 and bracket 6004 are shown mounted in a Flyte surgical helmet. The helmet includes a headband 7102 and a duct 7104 connected by a brace 7106. Bracket 6910 and clamp 6908 fully surround brace 7106 and fit tightly against its sides, top, and bottom to prevent angular movement between the bracket components (6908, 6910) and the brace 7106. In this embodiment, clamp 6908 contacts both duct 7104 and headband 7102 to prevent the bracket from moving forwards or backwards relative to the helmet. Bracket 6910 and clamp 6908 are drawn tightly together by two screws.

Figure 61:
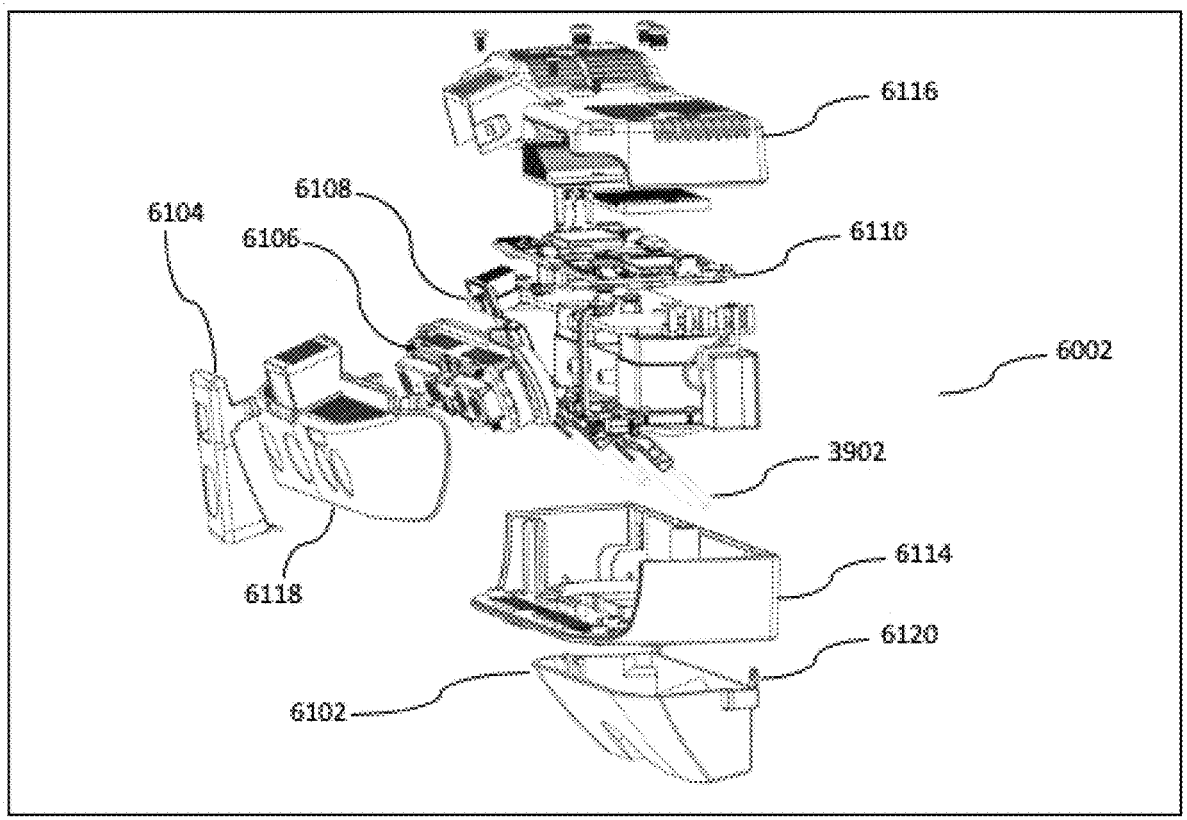
FIG. 61 shows an exploded view of the eyepiece depicted in FIG. 60.
Figure 70:
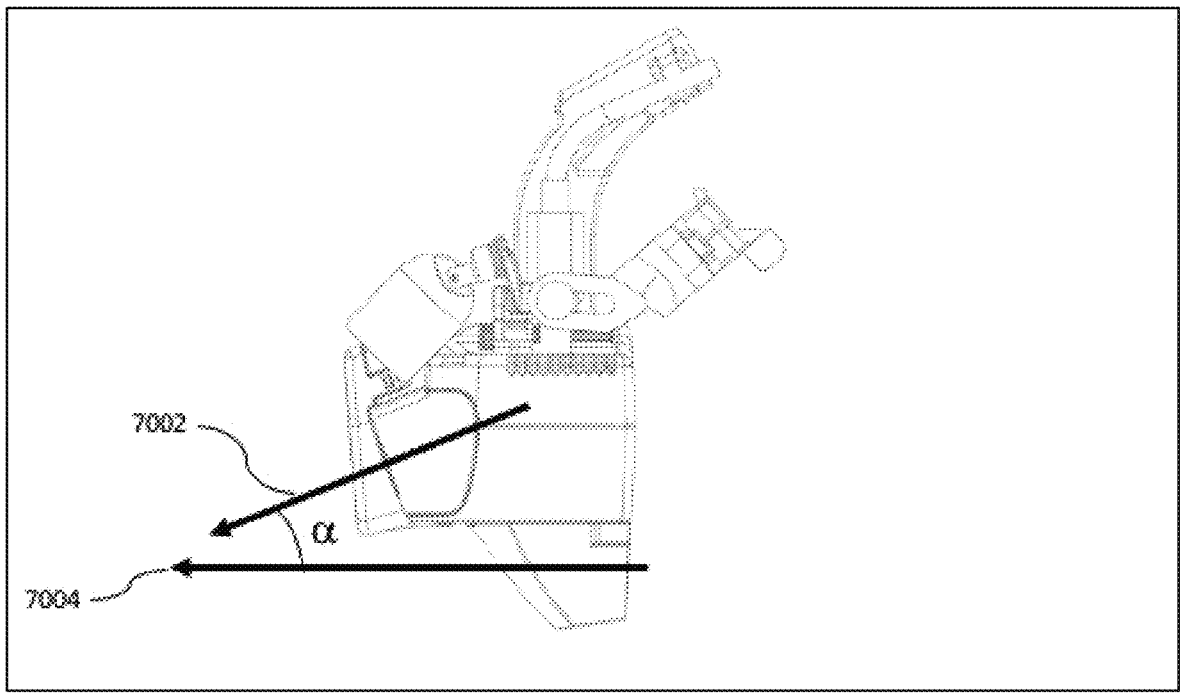
FIG. 70 shows a side view of the eyepiece and bracket depicted in FIG. 60.

Referring to FIG. 61, the components of one embodiment of eyepiece 6002 include a modular transparent visor 6102 and housing components 6114, 6116, and 6118 to protect the optical displays 3902. The visor 6102 can be removed and replaced without tools to allow easy replacement in case of damage or wear. Spring tabs 6120 engage with bottom housing 6114 to retain visor 6102. To attach the visor, the user pushes it into position against the bottom housing. The visor 61002 can be removed from bottom housing 6114 by lifting the tabs 6120 and pulling the visor off. A plurality of optional visors 6102 of various sizes and shapes allow optimal fit for each user accounting for the use of prescription eyewear, anatomical variations, and preference. In one embodiment, visor 6102 is configured to minimally obstruct outward view and allow the user 106 to look under the visor 6102 when not actively viewing information in the optical displays 3902. This may be additionally enabled by mounting the eyepiece 6002 high in the line of sight of user 106. Further referring to FIG. 61, this embodiment of the eyepiece 6002 includes a stereo camera module 6106 such as the Intel Realsense D435. In one embodiment, the stereo camera module 6106 utilizes infrared cameras, and the camera's viewing axis 7002 is angled down 20-30 degrees from the display's neutral viewing angle 7004, as shown as angle α in FIG. 70. In this embodiment, the camera module 6106 is positioned forward of the other internal electrical components to allow cooling air to pass around the camera module via vents in housing components 6114 below and 6118 above. Positioning camera module 6106 forward of the display module additionally moves the camera module closer to face shield 3608 (shown in FIG. 36B) and reduces the effect of reflections of light off of face shield 3608. Eyepiece 6002 further includes an infrared light 6108 to provide illumination for the stereo camera module 6106, allowing control over the scene illumination independent of the ambient room or procedural lighting. In one embodiment, the infrared light 6108 uses one or more dome LED components such as Lumileds L1I0-0850090000000. One embodiment includes a shroud 6104 comprising a plurality of sidewalls 7320 defining an aperture 7316 through which a light from an infrared light 6108 is emitted. The shroud 6104 is configured to fit closely to the face shield 3608 to minimize reflections of light from the infrared light 6108 into the camera module 6106. The shroud 6104 may be formed of or comprise a front surface 7204 coupled to border 7310 and may comprise a modular construction such that the shroud 6104 is easily replaceable or removable. Shroud 6104 may comprise a monolithic construction. Alternatively, border 7310 and front surface 7204 may be coupled, bonded, or otherwise fixed together to form shroud 6104. The shroud 6104 is further configured to avoid extending into the field of view of camera module 6106. In one embodiment, the shroud 6104 can be removed and replaced without tools, enabling the user 106 to select from a plurality of shrouds 6104 to optimize contact against face shield 3608, accounting for variations in eyepiece 6002 position for different user eyesight and anatomy. In one embodiment, spotlight or visible light 6006 includes an infrared light filter to prevent infrared light from the spotlight or visible light from reaching the camera module 6106. Infrared light illuminating the procedure site and reflecting back to camera module 6106 can also be limited by applying an infrared filter to spotlight 6006, ensuring its output is limited to visible wavelengths only. Circuit board 6110 coordinates communication of the camera module 6106 and optical displays 3902 with a computer located in the support module 3708.

Figure 72A:
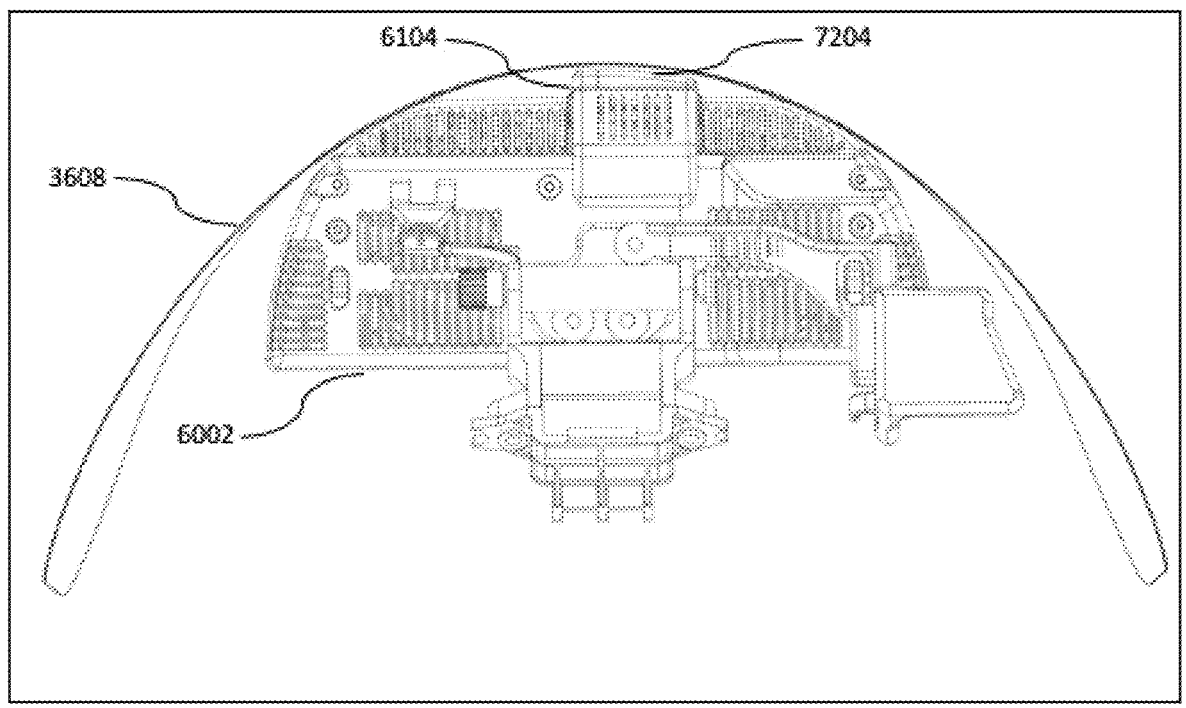
FIG. 72A shows a top view of the eyepiece depicted in FIG. 60 mounted relative to a surgical face shield.
Figure 72B:
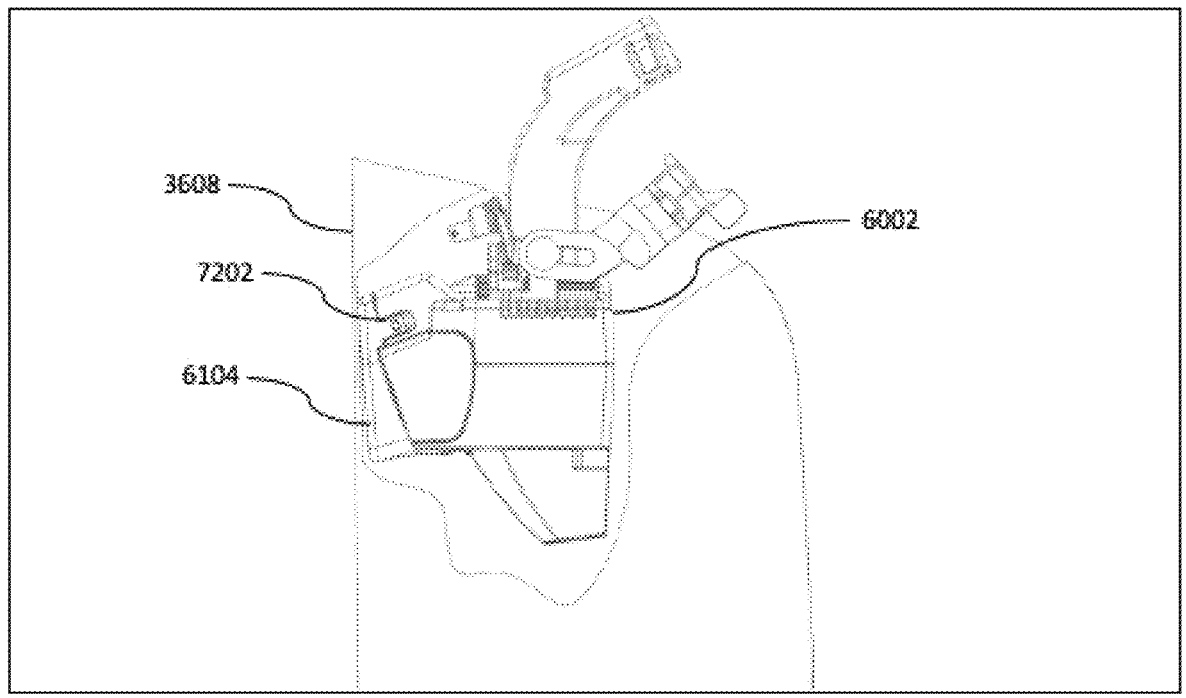
FIG. 72B shows a side view of the eyepiece depicted in FIG. 60 mounted relative to a surgical face shield.

Referring to FIGS. 72A and 72B, which show eyepiece 6002 in its installed position relative to face shield 3608 (shown transparent for clarity), some features of the system are illustrated. FIG. 72A shows a top view of the system, with FIG. 72B illustrating a side view of the same system. Because both infrared light 6108 and stereo camera module 6106 shown in FIG. 61, as components of eyepiece 6002, lie behind the face shield 3608, infrared light 6108 can be reflected off of face shield 3608 into camera module 3608, disrupting tracking of markers. This challenge is mitigated by the inclusion of shroud 6104, which extends around the infrared light 6108 to the face shield 3608. In some embodiments, aperture 7316 contacts face shield 3608; in other embodiments, a front surface 7204 coupled to and/or surrounding an outer perimeter 7324 of the plurality of sidewalls 7320 of shroud 6104 contacts the face shield 3608, is in close proximity (e.g., 0 to 5 mm, 0 to 1 mm, 0 to 2 mm, 0 to 3 mm, 0 to 4 mm, 0 to 6 mm, etc.) to the face shield 3608, or is otherwise adjacent to the face shield such that light emitted by the infrared light only escapes through the face shield and does not interfere with the camera module. Contact between any one or more portions of shroud 6104 and face shield 3608 prevents infrared light from escaping except through an aperture 7316 defined by the plurality of sidewalls 7320 of the shroud 6104 and thus through the face shield 3608. Any reflections of infrared light 6108 off of face shield 3608 are also contained within shroud 6104 and prevented from reaching camera module 6106. The plurality of sidewalls 7320 of shroud 6104 may be constructed from, may integrate, may be coated with, or otherwise include a material with low reflectivity of infrared light in the wavelengths discernable to camera module 6106, such as nylon PA12 or Cerakote ceramic coating. While face shield 3608 is in a fixed location relative to the user's head, eyepiece 6002 may be adjusted forward or backward to account for differences in eyesight and anatomy, which also decreases or increases the distance from shroud 6104 to face shield 3608. To minimize the gap between the shroud and face shield, a plurality of shrouds 6104 of varying lengths $L_{6104}$ can be provided, as shown in FIG. 73C, allowing the user to select the longest shroud that fits behind the face shield for a given position of eyepiece 6002. Shroud 6104 is held in place by one or more flexible spring tabs 7202 that mate with features on the eyepiece housing. Shroud 6104 snaps into place and can be removed without tools by lifting the spring tab(s) to release. To conform to the curved surface of face shield 3608 with minimal gap, shroud 6104 has a front surface 7204 with approximately the same radius of curvature as that of the face shield, as shown in FIG. 72A. In other words, a radius of curvature of the front surface 7204 of the shroud 6014 matches or approximately matches a radius of curvature of the face shield. In other embodiments (in the absence of front surface 7204), aperture 7316 has approximately the same radius of curvature as that of the face shield. In other words, a radius of curvature of the aperture 7316 of the shroud 6104 matches or approximately matches a radius of curvature of the face shield. The radius of the face shield may be zero (flat), 0 to 4 cm, 0 to 8 cm, 0 to 10 cm, etc.

Figure 73A:
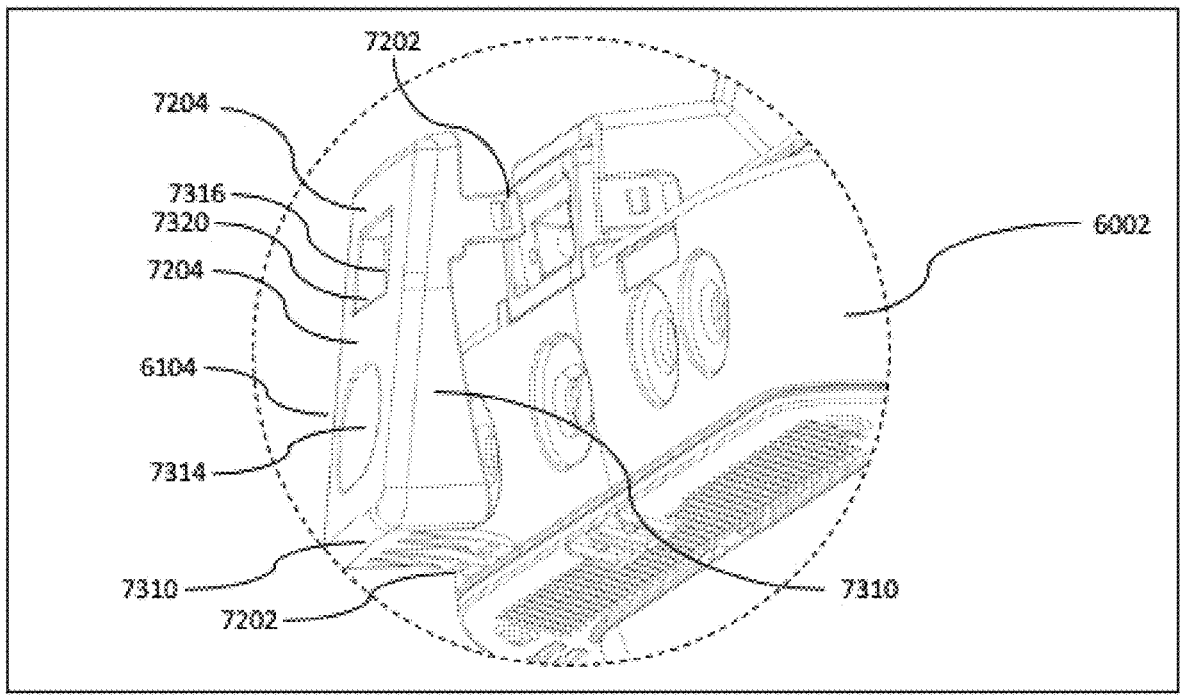
FIG. 73A shows a zoomed in view of a shroud of FIGS. 72A-72B.
Figure 73B:
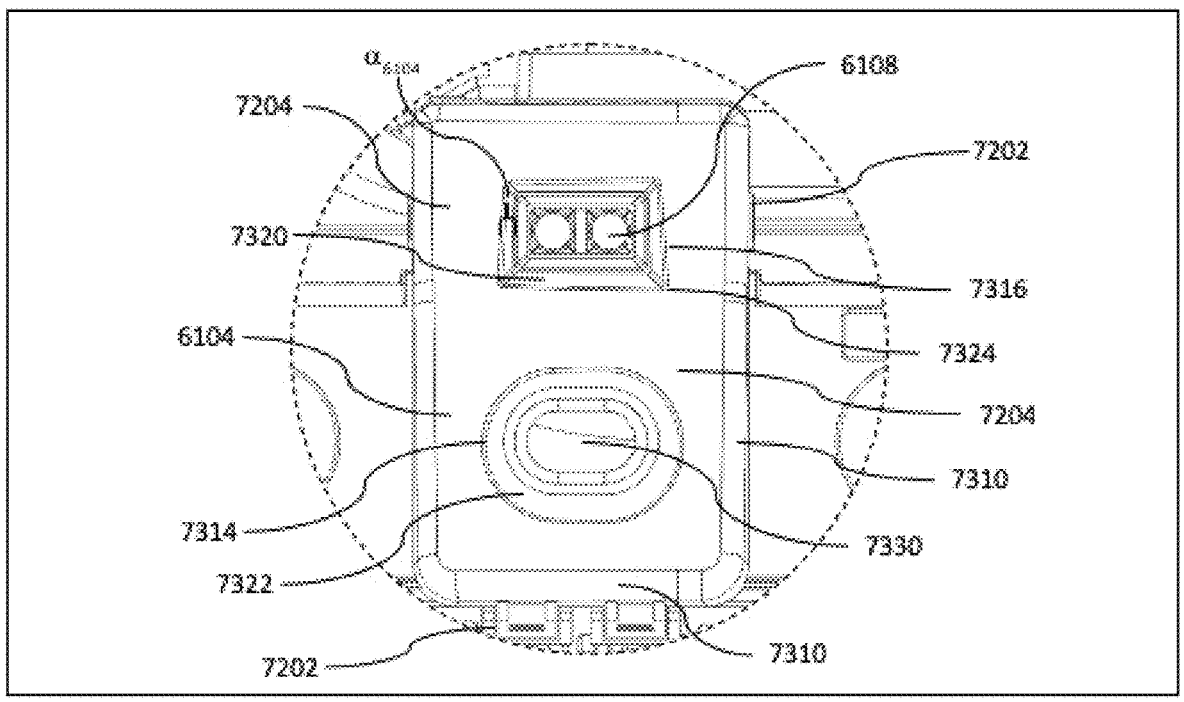
FIG. 73B shows a zoomed in front view of a shroud of FIGS. 72A-72B.
Figure 73C:
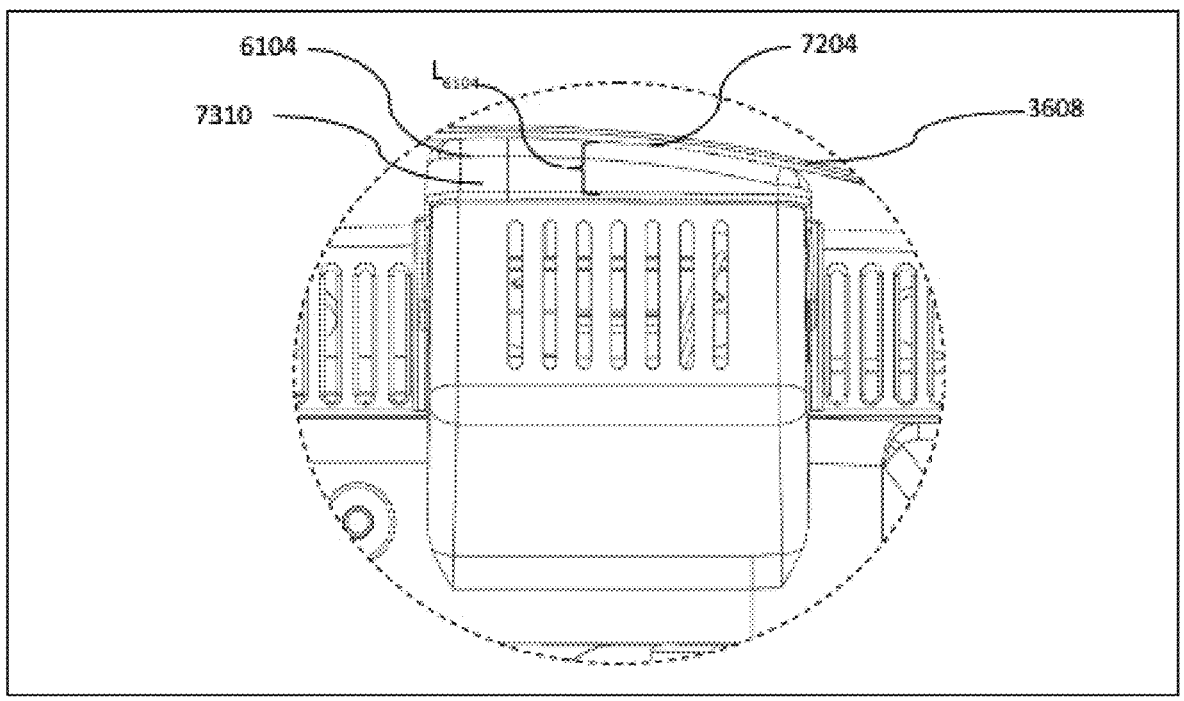
FIG. 73C shows a zoomed in top view of a shroud of FIGS. 72A-72B.

FIGS. 73A-73C show a perspective view, front view, and side view, respectively of shroud 6104. As shown in FIGS. 73A-73C, shroud 6104 includes a plurality of sidewalls that define one or more apertures. For example, the plurality of sidewalls 7320 define aperture 7316 which houses or surrounds infrared light 6108. Additionally, or alternatively, a second plurality of sidewalls 7322 may define a second aperture 7314 which houses a second infrared light, camera module, light projector, or other component 7330. In an embodiment comprising apertures 7314, 7316, the first and second apertures 7314, 7316 are combined into a modular component via front surface 7204 coupled to border 7310. The front surface 7204 interfaces with a face shield. In other embodiments, shroud 6104 does not include front surface 7204 such that the first and second plurality of sidewalls 7322, 7320 define the apertures 7314, 7316, respectively. Further, one or more of the plurality of sidewalls 7320 may have an angle $\alpha_{6104}$ as measured from a central axis of the infrared light 6108 or a central axis of a cone of light (e.g., cone may be substantially or about 90 degrees) emitted by the infrared light 6108. The angle $\alpha_{6104}$ may be about or substantially: 0 to 50 degrees, 0 to 40 degrees, 0 to 30 degrees, 0 to 20 degrees, 0 to 10 degrees, 0 to 5 degrees, 5 to 10 degrees, 10 to 20 degrees, 5 to 20 degrees, 5 to 25 degrees, etc. In one embodiment, angle $\alpha_{6104}$ is substantially or about 12 to 16 degrees. In another embodiment, angle $\alpha_{6104}$ is substantially or about 10 to 18 degrees. In some embodiments, each of the plurality of sidewalls is angled at the same or substantially the same angle. In other embodiments, opposing sidewalls have a same or similar angle. In still other embodiments, each of the plurality of sidewalls is angled at a different angle that the other sidewalls.

Figure 62:
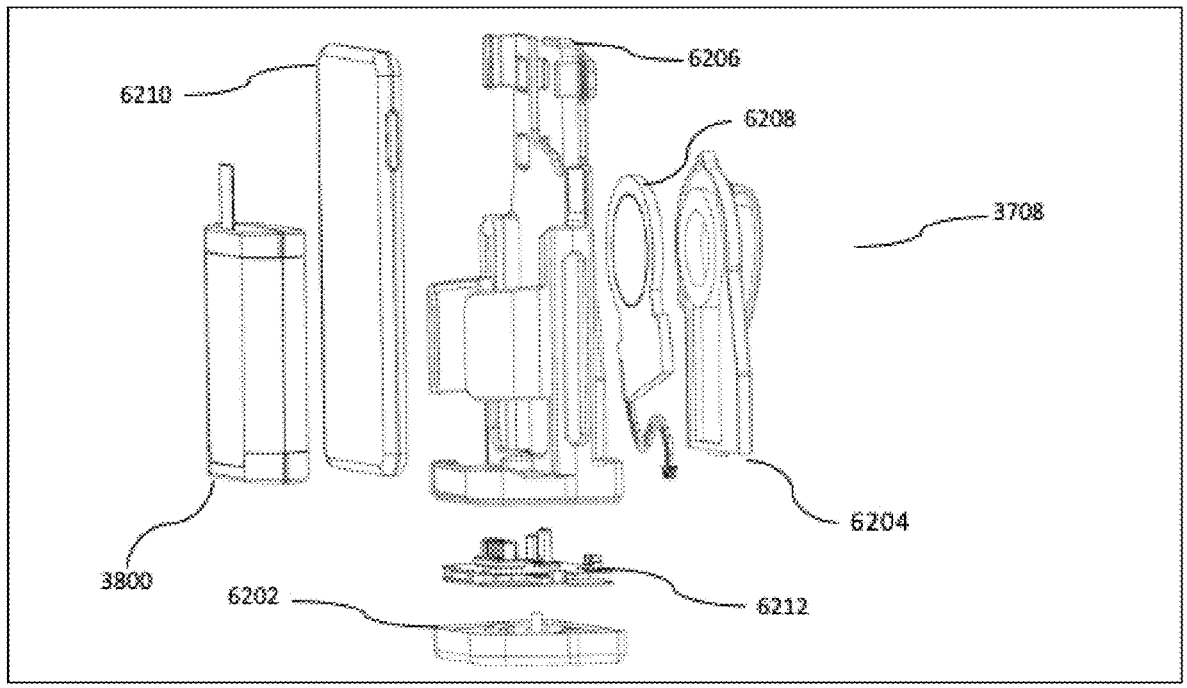
FIG. 62 shows an exploded view of the support module.

Referring to FIG. 62, which shows an exploded view of an embodiment of support module 3708, all electronic components are contained in or mounted to a housing comprising base 6202 configured to receive circuit board 6212; coupler 6204 configured to couple the housing to clothing, a strap, a belt, or the like; and bracket 6206 configured to securely and reversibly restrain battery 3800 and processor unit 6210. The battery 3800 may be received into housing in a fixed orientation; in other embodiments, the battery 3800 is configured to fit into the housing in more than one orientation. A replaceable battery 3800 powers computer module or processor unit 6210 and AR eyepiece 6002 or head-worn display device. Bracket 6206 is configured to allow an assistant to replace battery 6800 without using tools or manipulating mechanical latches. Circuit board 6212 is configured to direct electrical power from battery 3800 to computer module or processor unit 6210 and AR eyepiece 6002. In one embodiment, power and data flow between support module 3708 and AR eyepiece 6002 or a head-worn display device via a USB connection. In one embodiment, the computer module or processor unit 6210 is a mobile phone with a single USB connector. In one embodiment, the computer module or processor unit 6210 receives power from battery 3800 through a wireless charger 6208, enabling the USB connector of computer module or processor unit 6210 to behave as a full-time power source, and reduce the likelihood of it behaving as a power "sink."

Figure 63:
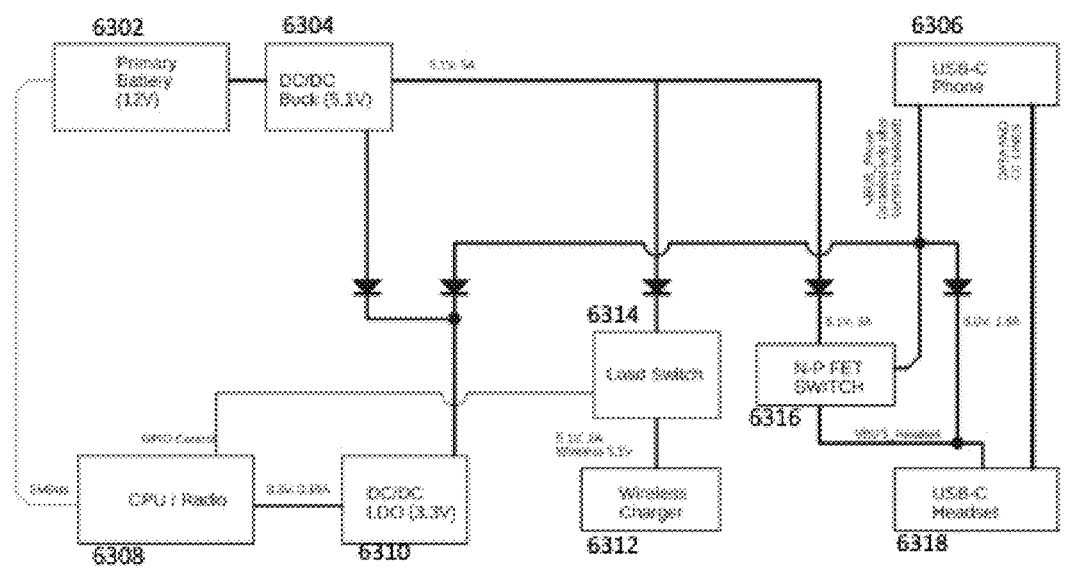
FIG. 63 is a schematic view of the electrical hardware configuration of support module circuit board 6212.

Referring to FIG. 63, in which an electrical schematic for a support module circuit board 6212 is shown, a battery connector 6302 receives power from replaceable battery 3800 and DC/DC buck circuit 6304 steps the voltage down to the nominal system voltage. DC/DC LDO regulator 6310 ensures the voltage is at the required level and passes power to CPU/Radio 6308. Power flows to wireless charger 6312 through load switch 6314 as directed by CPU/Radio 6308. Power flows through N-P FET switch 6316 to both phone USB connector 6306 and headset USB connector 6318. CPU/Radio 6308 monitors the charge level of battery 3800 and reports the level to computer module 6210 using radio transmission.

In an exemplary embodiment, the AR headset 3600 is optionally used as a system for reporting device complaints or design feature requests. The user interface can have a menu option or voice command to initiate a report at the time that it occurs. This would activate voice and video camera recording allowing the user 106 to capture and narrate the complaint in 3D while the issue is occurring. The user 106 terminates complaint with voice or selecting an option. The complaint record is compressed and transmitted to the company via the internet to wirelessly providing complaint handling staff excellent data to be able to "re-live" the situation firsthand for better diagnosis. Artificial intelligence can be used to parse and aggregate the complaint material to establish patterns and perform statistical analysis. The same sequence can be used to connect to live technical support during the procedure with the exception that the data stream is transmitted in real-time.

II. Pre-Operative Procedures

The present invention can be used for pre-operative tasks and surgical procedures. For example, an alternate general surgical procedure that includes possible pre-operative activities is now described. First, a scan of the region of interest of the patient such as CT or MM is obtained. If possible, the patient should be positioned in a way that approximates positioning during surgery. Second, segmentation of the scan data is performed in order to convert it into three-dimensional models of items of interest including but not limited to: teeth and bony structures, veins and arteries of interest, nerves, glands, tumors or masses, implants and skin surfaces. Models are segregated so that they can later be displayed, labeled or manipulated independently. These will be referred to as pre-operative models. Third, pre-operative planning is performed (optionally using VR for visualization and manipulation of models) using models to identify items including, but not limited to: anatomic reference frames, targets for resection planes, volumes to be excised, planes and levels for resections, size and optimum positioning of implants to be used, path and trajectory for accessing the target tissue, trajectory and depth of guidewires, drills, pins, screws or instruments. Fourth, the models and pre-operative planning data are uploaded into the memory of the display device 104 prior to or at time of surgery. This uploading process would most conveniently be performed wirelessly via the radio.

Fifth, the patient is prepared and positioned for surgery. During surgery, the surgical site is ideally be draped in a way that maximizes the visualization of skin surfaces for subsequent registration purposes. This could be achieved by liberal use of Ioban. It would be beneficial to use a film like Ioban that fluoresced or reflected differently when targeted by a specific LED or visible light emitter in a broad illumination, point, or projected pattern. This film may also have optical features, markers, or patterns, which allowed for easy recognition by the optical cameras of the headpiece.

Sixth, after the patient has been prepped and positioned for surgery, the system 10 (e.g., via the AR headset 3600) scans the present skin envelope to establish its present contour and creates pre-operative 3D models available for user 106 to see on the display device 104. The preferred method is to project a grid or checkerboard pattern in infrared ("IR") band that allows for determination of the skin envelope from the calculated warp/skew/scale of the known image. An alternate method is to move a stylus type object with a marker attached back and forth along exposed skin, allowing the position and orientation track of the stylus and subsequent generation of the skin envelope. Optionally, the skin model is displayed to the user 106, who then outlines the general area of exposed skin, which has been scanned. An optimum position and orientation of the pre-operative skin model is calculated to match the present skin surface. The appropriate pre-operative models are displayed via the display device 104 to the user 106 in 3D. Optionally, the user 106 may then insert an optical marker into a bone of the patient for precise tracking. Placement of this marker may be informed by his visualization of the pre-operative models. The position and orientation of pre-operative models can be further refined by alternative probing or imaging including, but not limited to, ultrasound.

Seventh, during surgery, the user 106 using the system 10 with the display device 104, can see the pre-operative planning information and can track instruments and implants and provide intraoperative measurements of various sorts including, but not limited to, depth of drill or screw relative to anatomy, angle of an instrument, angle of a bone cut, etc.

Figure 8:
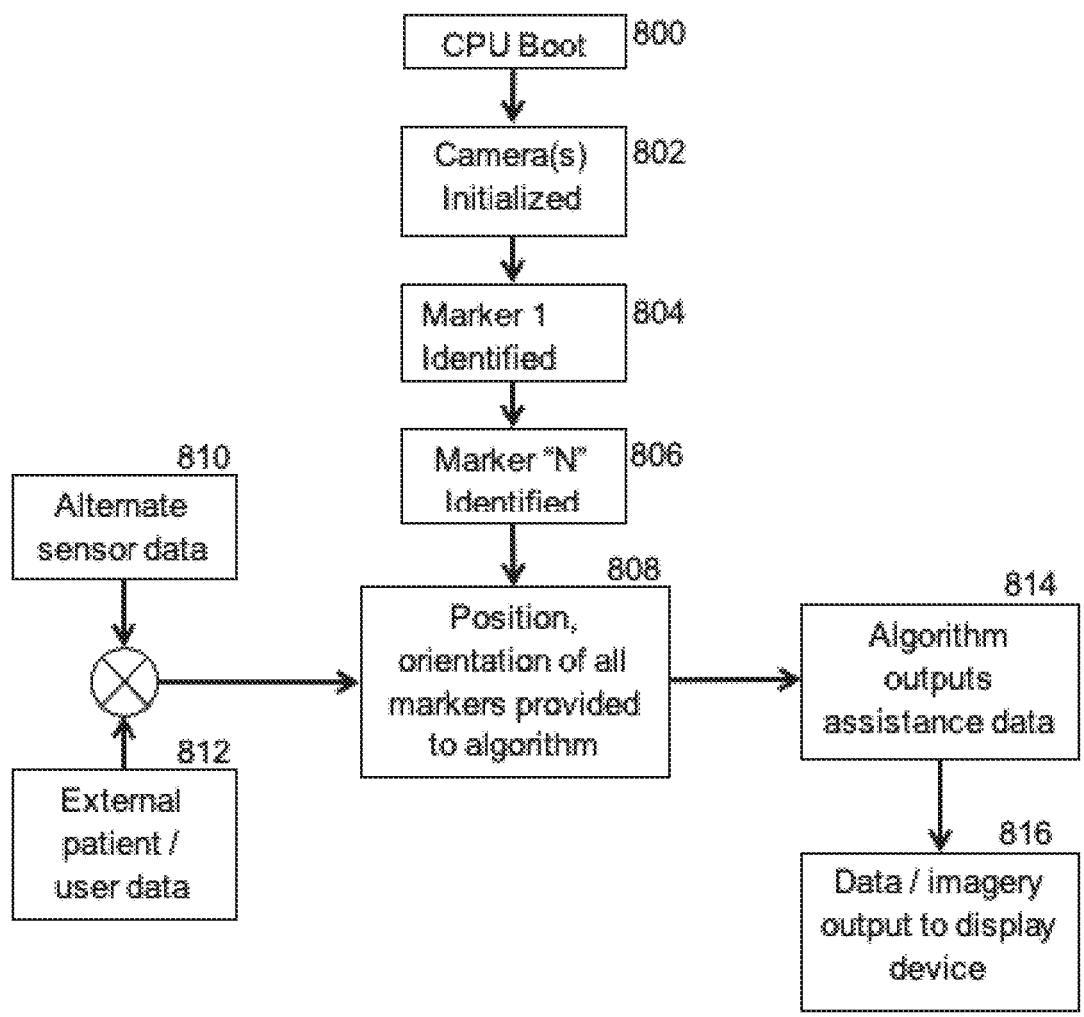
FIG. 8 is a flowchart showing the operational processes of the system of FIG. 1 during a medical procedure.

Referring to FIG. 8, an exemplary embodiment of the operational flow during a procedure using the system 10 is presented. In this embodiment, the CPU 401 boots (800) and initializes one or more cameras 402, 404, 406 (802). When in the field of view of the camera(s) 402, 404, 406, the first marker 100 is located and identified (804), followed by subsequent markers 108, 110 (806). The track of these markers 100, 108, 110 provides position and orientation relative to each other as well as the main camera locations (808). Alternate sensor data from sensors such as IMUs and cameras from the remote sensor suites 422 (810) can be optionally incorporated into the data collection. Further, external assistance data (812) about the patient, target, tools, or other portions of the environment may be optionally incorporated for use in the algorithms. The algorithms used in the present invention are tailored for specific procedures and data collected. The algorithms output (814) the desired assistance data for use in the display device (816).

III. Hip Replacement Procedures

Figure 6:
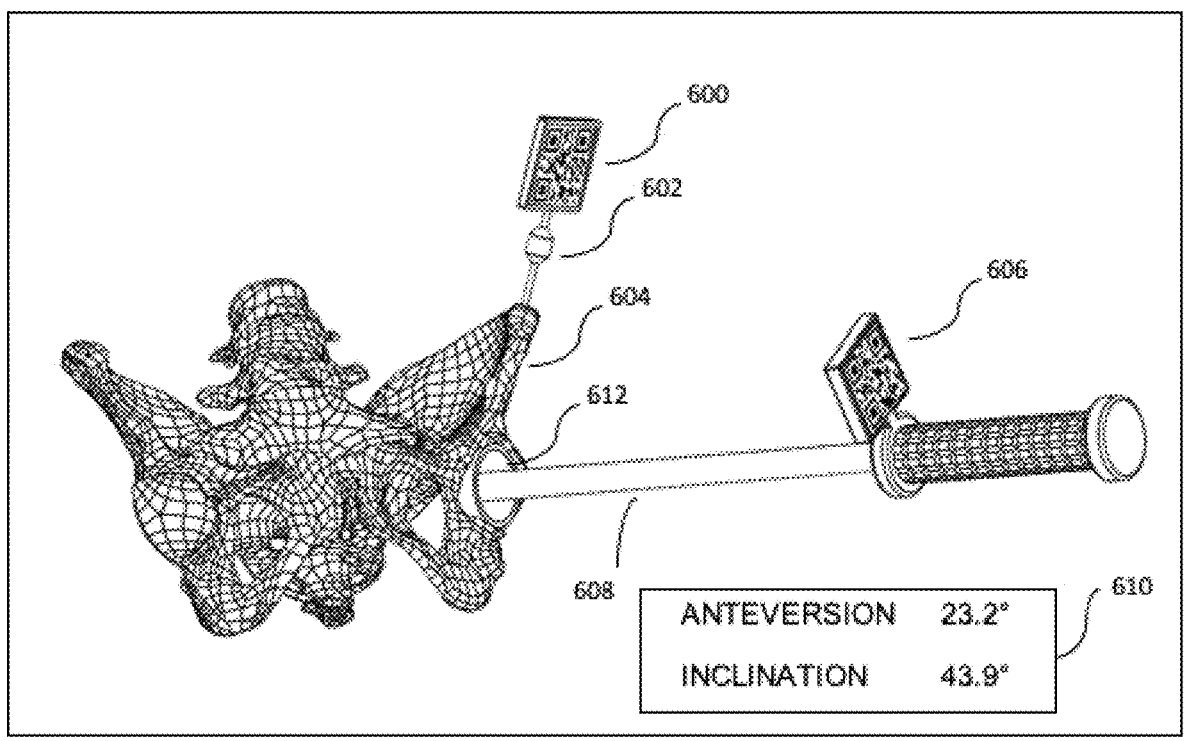
FIG. 6 is a diagrammatic depiction of a mixed reality user interface image ("MXUI") provided by system of FIG. 1 during positioning of an acetabular shell in a hip replacement procedure showing a virtual pelvis.

In one exemplary embodiment of the present invention and referring to FIG. 6, the system 10 is used for hip replacement surgery wherein a first marker 600 is attached via a fixture 602 to a pelvis 604 and a second marker 606 is attached to an impactor 608. The user 106 can see the mixed reality user interface image ("MXUI") shown in FIG. 6 via the display device 104. The MXUI provides stereoscopic virtual images of the pelvis 604 and the impactor 604 in the user's field of view during the hip replacement procedure.

The combination of markers (600, 606) on these physical objects, combined with the prior processing and specific algorithms allows calculation of measures of interest to the user 106, including real time version and inclination angles of the impactor 608 with respect to the pelvis 604 for accurate placement of acetabular shell 612. Further, measurements of physical parameters from pre- to post-operative states can be presented, including, but not limited to, change in overall leg length. Presentation of data can be in readable form 610 or in the form of imagery including, but not limited to, 3D representations of tools or other guidance forms.

Figure 7:
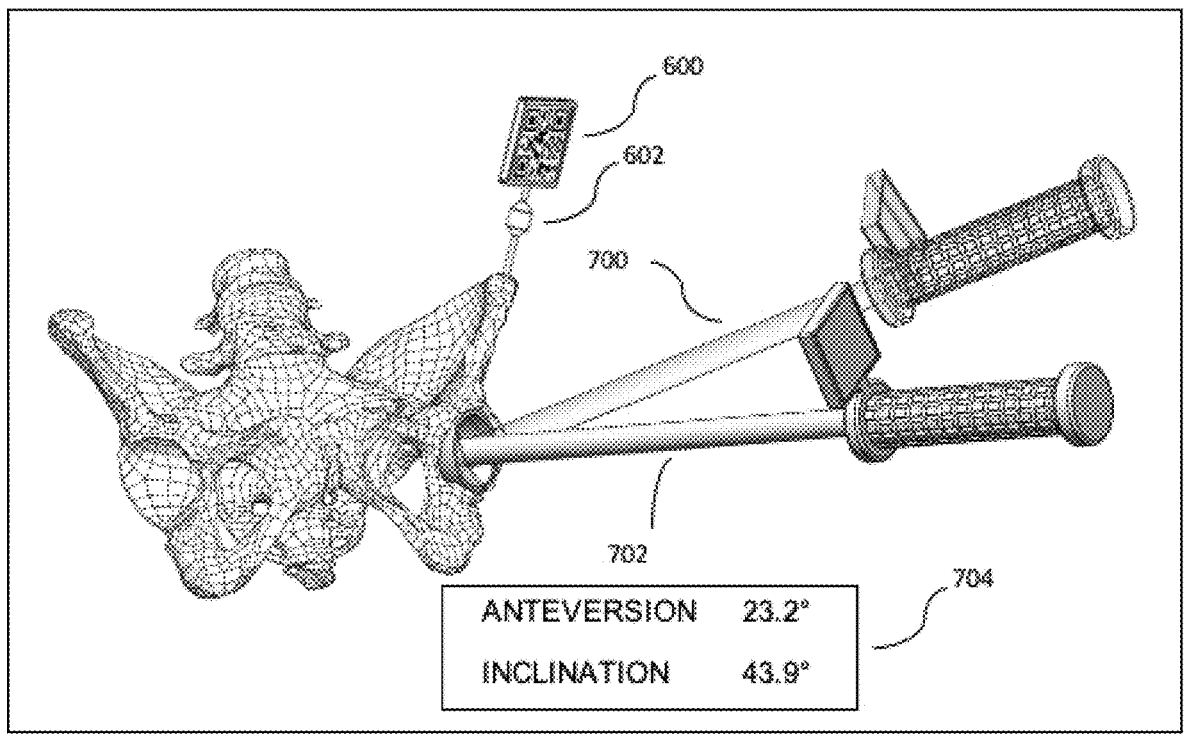
FIG. 7 is a diagrammatic depiction of a MXUI provided by system of FIG. 1 during positioning of an acetabular shell in a hip replacement procedure showing a virtual pelvis and virtual acetabular impactor.

FIG. 7 depicts an alternate view of the MXUI previously shown in FIG. 6, wherein a virtual target 700 and a virtual tool 702 are presented to the user 106 for easy use in achieving the desired version and inclination. In this embodiment, further combinations of virtual reality are used to optimize the natural feeling experience for the user by having a virtual target 700 with actual tool 702 fully visible or a virtual tool (not shown) with virtual target fully visible. Other combinations of real and virtual imagery can optionally be provided. Presentation of data can be in readable form 704 or in the form of imagery including, but not limited to, 3D representations of tools or other guidance forms.

Figure 9:
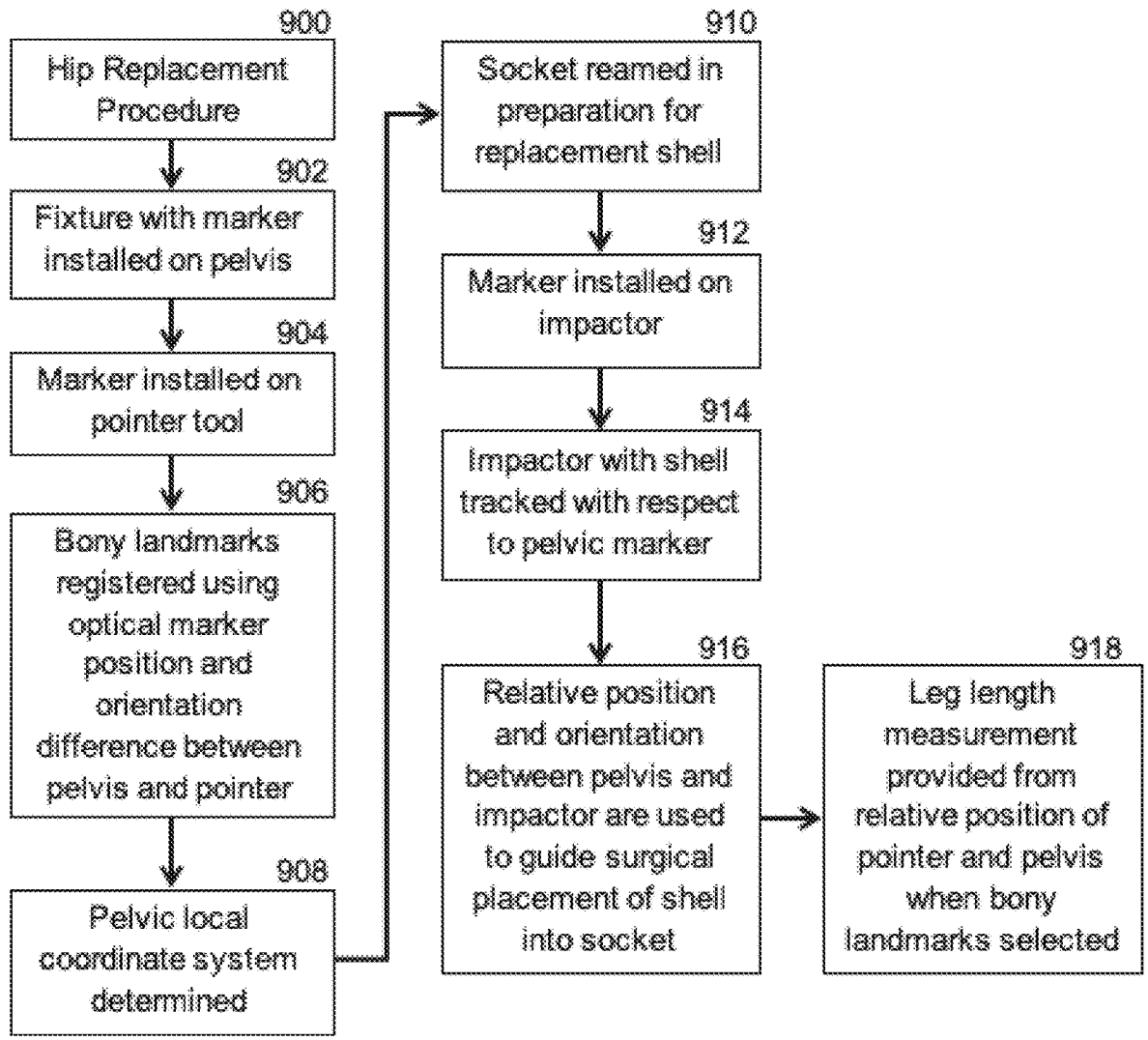
FIG. 9 is a flowchart showing a method of using the system of FIG. 1 to perform a hip replacement procedure in accordance with the principles of the present invention.

Referring to FIG. 9, the present invention further provides a method of using the system 10 to perform a hip replacement procedure (900) in which a hip bone has the socket reamed out and a replacement cup is inserted for use with a patient's leg. In this embodiment, a first marker (e.g., 100, 108, or 110, etc.) is installed on a fixture of known dimensions with respect to the marker and this fixture is installed on the hip bone of a patient (902). A second distinct marker (e.g., 100, 108, or 110, etc.) is installed on a pointing device of known dimensions with respect to the first marker (904). Bony landmarks or other anatomic landmarks position and orientation relative to the hip fixture are registered using the optical markers and the position/orientation difference between the hip and the pointer (906). These points are used to determine a local coordinate system (908). The pointer is used to determine position and orientation of the femur before the femur is dislocated and the acetabulum of the hip bone is reamed to make room for the replacement shell (910). An impactor with replacement shell installed on it has a third distinct marker installed with known dimensions of the impactor (912). The impactor with shell is tracked per the previously described algorithm with respect to the hip marker (914). The relative position and orientation between the hip marker and impactor are used to guide surgical placement of the shell via AR or VR display into the socket at a desired position and angle per medical requirement for the patient (916). The change in leg length can also be calculated at this point in the procedure using the marker position and orientation of the replaced femur (918). Another embodiment augments this procedure with pre-operative CT data to determine component positioning. Another embodiment uses the display output in an AR or VR manner to determine the femoral head cut. Another embodiment uses the data to place screws in the acetabulum.

The coordinate reference frame of the table or support on which the patient lies is desirable in some implementations. Table alignment with respect to ground, specifically gravity, can be achieved as follows. The IMU (from each of the sensor suites such as the one located within the AR headset 3600) provides the pitch and roll orientation of the display device 104 with respect to gravity at any given instant. Alternatively, SLAM or similar environment tracking algorithms will provide the pitch and roll orientation of the display device 104 with respect to gravity, assuming most walls and features associated with them are constructed parallel to the gravity vector. Separate from the display device's 104 relationship between to gravity, the table orientation may be determined by using the stylus to register three (3) independent points on the table. With these three points selected in the display device 104 coordinate frame, the table roll and pitch angles with respect to gravity can then be determined as well. Alternatively, the table may be identified and recognized using machine vision algorithms to determine orientation with respect to gravity. The alignment of the patient spine relative to the display device 104, and therefore any other target coordinate systems such as defined by the hip marker, in pitch and roll is now known. To provide a yaw reference, the stylus can be used in conjunction with the hip marker to define where the patient head is located, which provides the direction of the spine with respect to him. Alternatively, image recognition of the patients head can be used for automatic determination. Ultimately, the roll, pitch and yaw of the table and/or patient spine are now fully defined in the display device 104 and all related coordinate systems.

Figure 11:
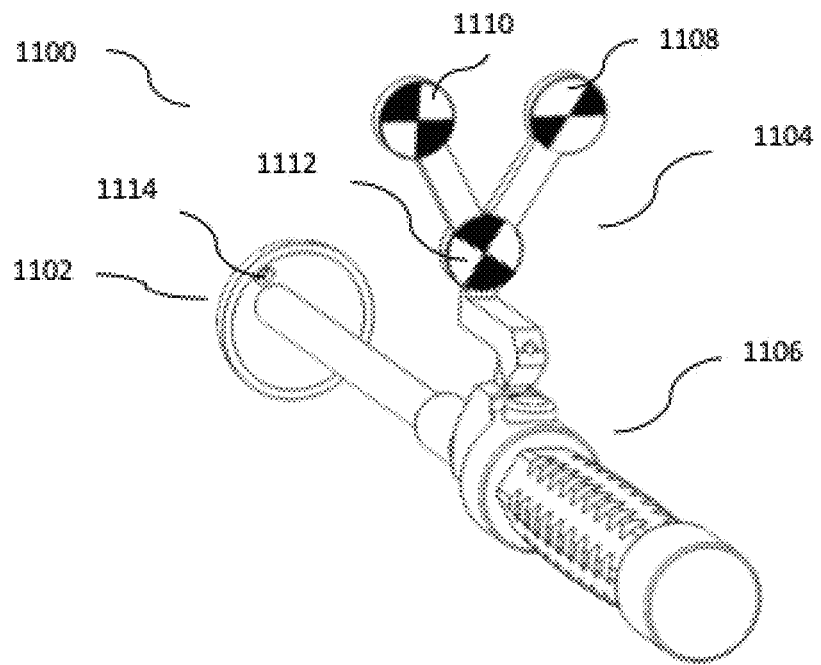
FIG. 11 shows a perspective view of a diagrammatic depiction of a hip impactor assembly including an acetabular shell and an optical marker.
Figure 12:
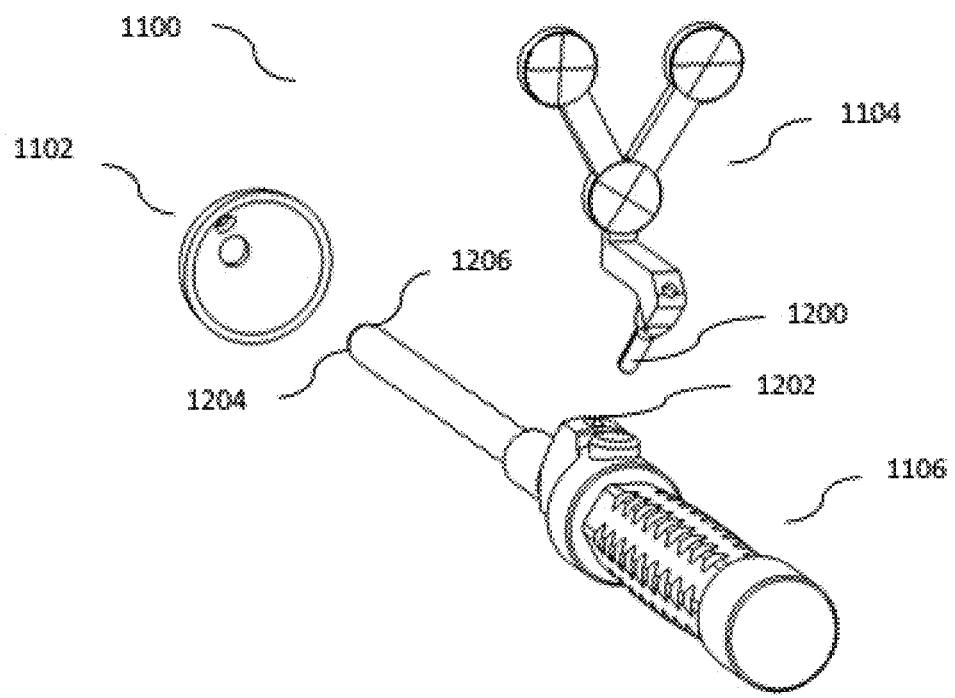
FIG. 12 shows an exploded view of the hip impactor assembly shown in FIG. 11.

Referring to FIGS. 11-12, the system 10 may optionally include a hip impactor assembly 1100 for use in hip arthroplasty procedures. The assembly includes an acetabular shell 1102, and an optical marker 1104 (same as 100, 108, 110, 502, 504, 600, 606, 804, 806, 904, 912 described above) assembled to an acetabular impactor 1106. FIG. 12 depicts an exploded view of the assembly 1100 illustrating how the optical marker 1104 attaches to the impactor 1106 in a reproducible way by insertion of an indexed post 1200 into an indexed hole 1202. The acetabular shell 1102 assembles reproducibly with the impactor 1106 by screwing onto a threaded distal end 1204 of the impactor and seating on a shoulder 1206. The marker 1104 includes a first fiducial 1108, a second fiducial 1110, and a third fiducial 1112; each having adjacent regions of black and white wherein their boundaries form intersecting straight lines. Algorithms in the AR headset 3600 are used to process the images from the stereoscopic cameras (3904) to calculate the point of intersection of each fiducial (1108, 1110, 1112) and thereby determine the six-degrees of freedom pose of the marker 1104. For the purpose of this specification, "pose" is defined as the combination of position and orientation of an object. The fiducials (1108, 1110, and 1112) can be created by printing on self-adhesive sticker, by laser-etching the black regions onto the surface of white plastic material, or alternative methods. The shell contains a fixation hole 1114 through which a screw is optionally used to fixate the shell 1102 to the bone of the acetabulum.

Figures 13A, 13B:
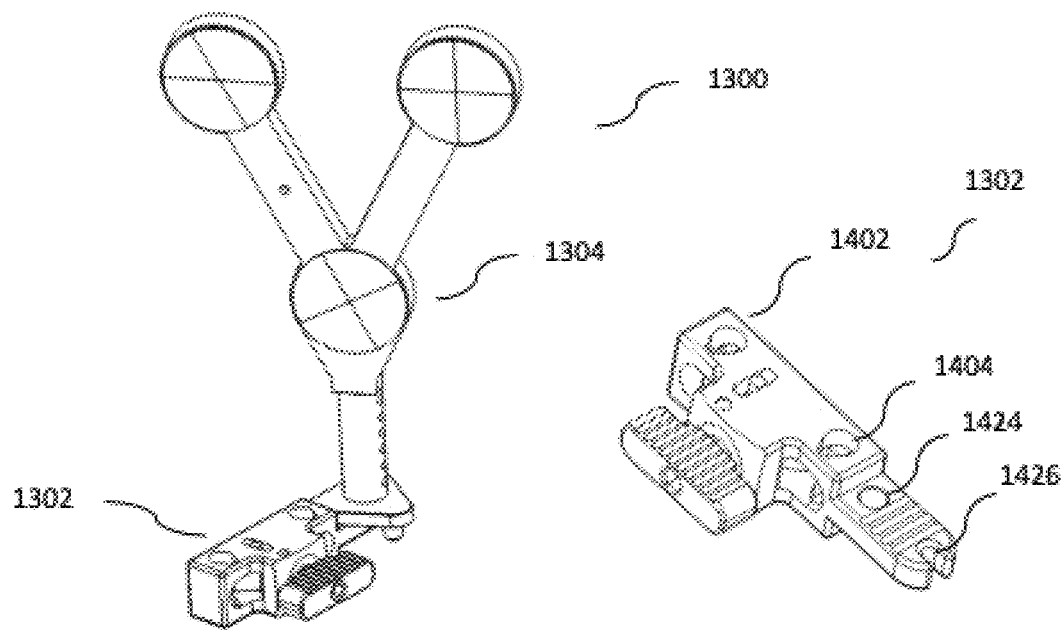
FIG. 13A shows a perspective view of a diagrammatic depiction of an anatomy marker assembly that is optionally included in the system of FIG. 1.
FIG. 13B shows a perspective view of a clamp assembly of the anatomy marker shown in FIG. 13A.
Figure 14:
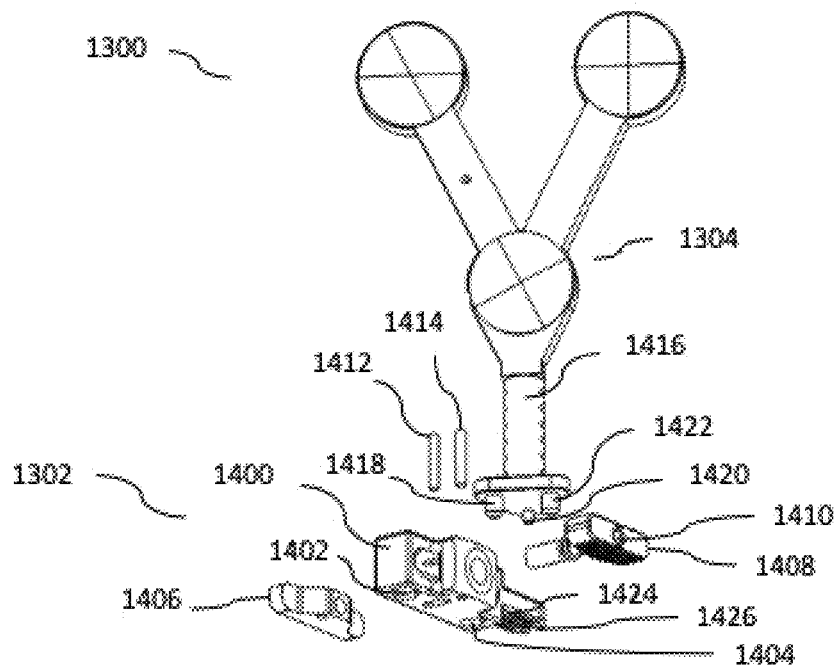
FIG. 14 shows an exploded view of the anatomy marker assembly shown in FIG. 13A.

In another exemplary embodiment and referring to FIGS. 13A-B and 14, the system 10 optionally includes an anatomy marker assembly 1300 comprising a clamp assembly 1302 and an optical marker 1304. The clamp assembly 1302 includes a base 1400, which defines a first teardrop-shaped hole 1402 and a second teardrop-shaped hole 1404. Fixation pins (not shown) which have been fixed to the bone can be inserted through the teardrop shaped holes (1402, 1404) and clamped between a clamp jaw 1406 and the body 1400 thereby fixing the clamp assembly 1302 to the pins and therefore to the bone. A clamp screw 1408 engages threads in the jaws and is used to tighten the assembly 1302 onto the pins. A hexagonal hole 1410 allows a hex driver to be used to tighten the assembly 1302. A first retaining pin 1412 and a second retaining pin 1414 prevent disassembly of the clamp assembly 1302. A marker body 1416 has a first locating post 1418, as second locating post 1420, and a third locating post 1422, which provide location to the base 1400 by engaging two locating posts with a locating hole 1424 and locating slot 1426 in the base. The design provides for two possible rotational positions of the marker 1304 which allows the marker 1304 to be oriented relative to the cameras (e.g., 3904) in the display device 104 (e.g., the AR headset 3600) for optimal tracking. The marker body 1416 encapsulates a magnet (not shown) which provides sufficient holding force to the base 1400.

Figure 15:
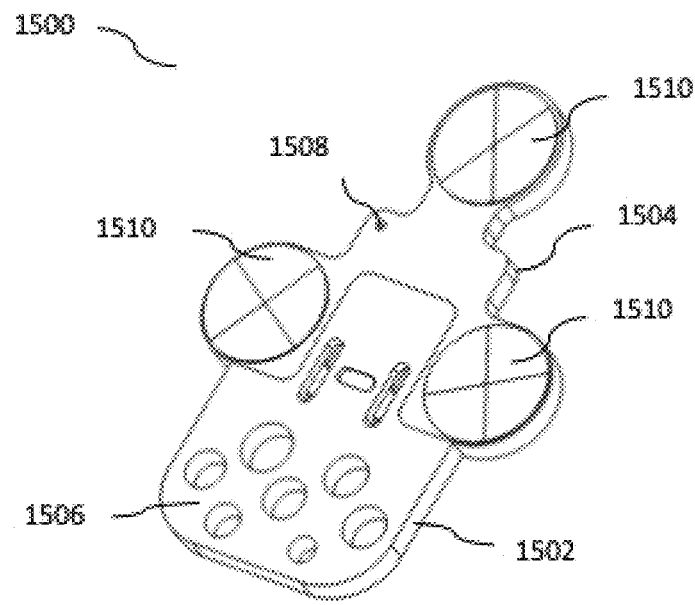
FIG. 15 shows a perspective view of a diagrammatic depiction of a calibration assembly that is optionally included in the system of FIG. 1.
Figure 16:
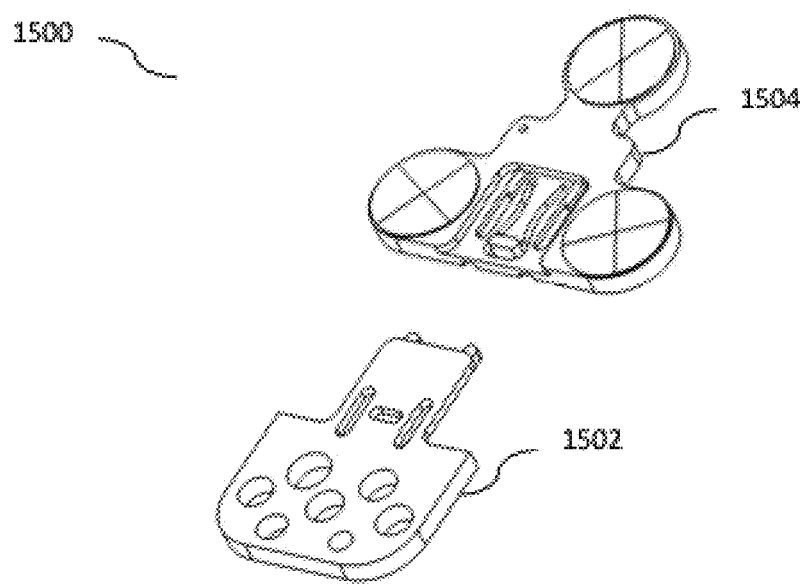
FIG. 16 shows an exploded front view of the calibration assembly shown in FIG. 15.
Figure 17:
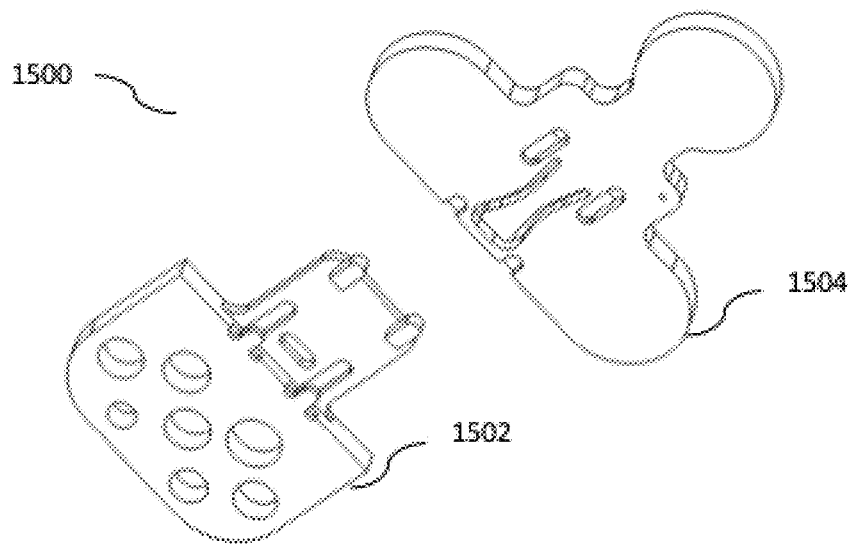
FIG. 17 shows an exploded back view of the calibration assembly shown in FIG. 16.

Referring to FIGS. 15-17, the system 10 may optionally include a calibration assembly 1500 comprising a plate 1502 and a marker 1504 with tongue and groove assembly features for coupling plate 1502 and marker 1504 together. The tongue and groove assembly features are especially useful for precisely assembling a metal part to a plastic part, which has a different rate of thermal expansion than the metal part. The plate 1502 has a plurality of holes 1506 having a plurality of thread types to accept various impactor types. The marker 1504 has a dimple 1508 into which the tip of a stylus may be inserted for registration. The marker 1504 has a plurality of fiducials 1510.

Figure 18:
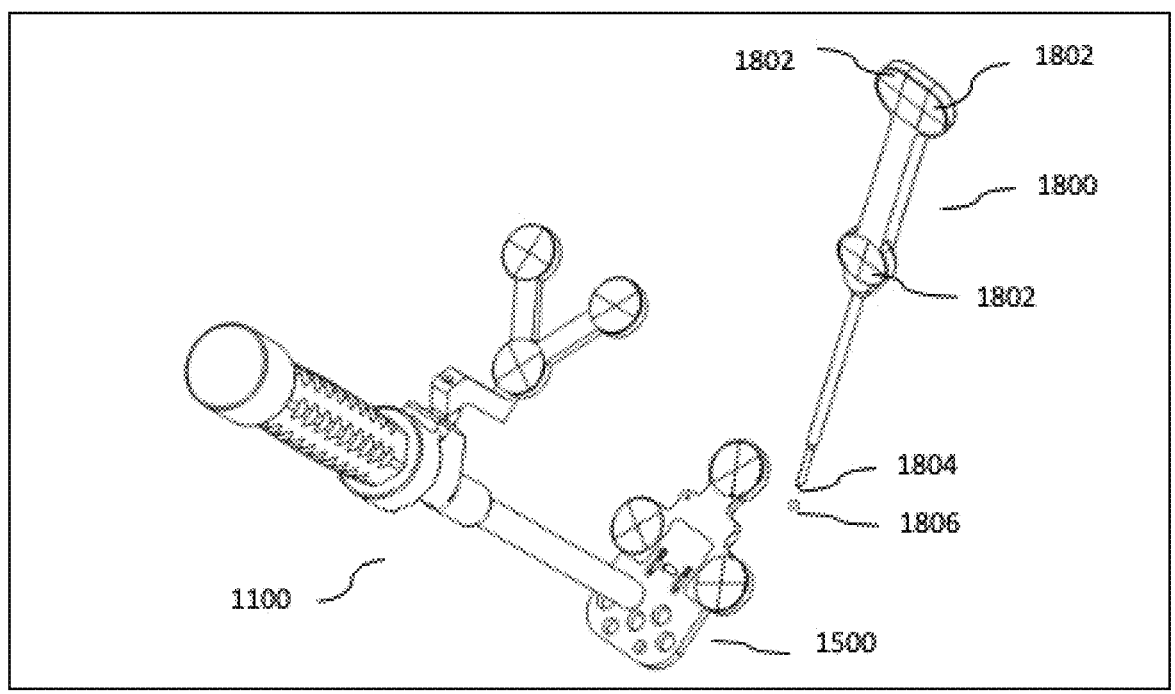
FIG. 18 shows a diagrammatic depiction of a MXUI provided by system of FIG. 1 during various calibration steps.

FIG. 18 depicts an exemplary embodiment of a MXUI shown to the user 106 via the display device 104 (e.g., the AR headset 3600) showing the calibration assembly 1500 being used for various calibration steps. First, the hip impactor assembly 1100 can be screwed into the appropriate hole of the plate 1502 so that the shoulder 1206 is seated squarely without play against the surface of the plate 1502. The cameras 3904 of the AR headset 3600 can then capture images which are processed by an algorithm to determine the relationship between the shoulder of the impactor on which the acetabular shell will seat and the marker 1104 of the hip impactor assembly 1100. A stylus 1800 is shown which contains a plurality of fiducials 1802 for tracking. The tip 1804 of the stylus 1800 may be inserted into the dimple 1508 of the plate 1502 allowing the coordinate of the tip 1804 relative to the marker of the stylus 1800 to be determined. A virtual guide point 1806 is shown which is projected into the user's 106 field of view at a specific location relative to the marker 1504. The user 106 places the tip 1804 of the actual stylus 1800 where the virtual guide point 1806 is located according to the user's 106 depth perception thereby connecting his actual view with the virtual view represented by the virtual guide point. An algorithm then applies a correction factor to account for variables such as the intraocular distance of the user 106. This is beneficial if the user's depth perception will be relied on in a mixed reality state for precise location of tools or implants.

Figure 19:
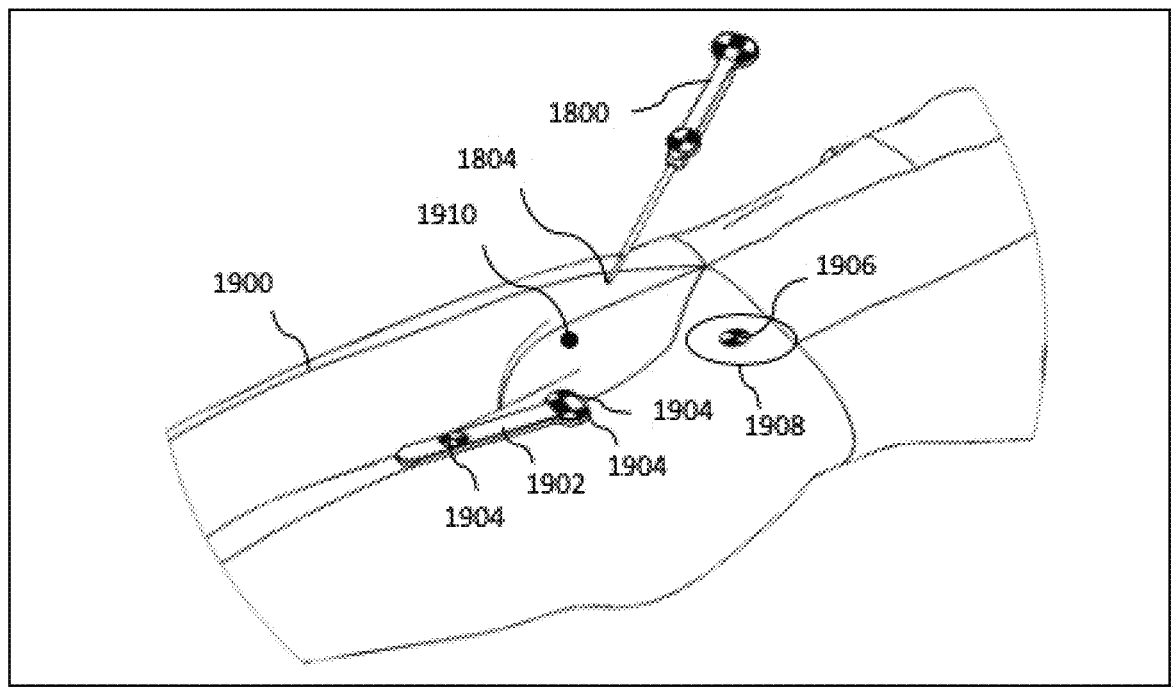
FIG. 19 is a diagrammatic depiction of a MXUI provided by system of FIG. 1 during a pelvic registration step of a hip replacement procedure.

FIG. 19 depicts an exemplary embodiment of a MXUI shown to the user 106 via the display device 104 of a patient 1900 at the beginning of a hip replacement procedure. A femur marker 1902, having a plurality of fiducials 1904 for tracking, is attached to the skin of the patient's 1900 thigh with adhesive tape such as Ioban. Alternatively, the femur marker 1902 could be fixated directly to the bone of the femur by use of pins and a clamp assembly like that depicted in FIG. 13B. The user 106 registers the anterior landmarks of the pelvis using the tip 1804 of the stylus 1800 to determine the location of the pelvis in the reference frame of the femur marker 1902 to establish a temporary pelvic reference frame. In another embodiment, this registration can be in the body reference frame defined by SLAM scanning of the visible surface of the patient. In another embodiment, the anterior landmarks of the pelvis can be registered by generating a surface map with SLAM and having the user 106 identify each point by positioning a virtual point 1910 on each landmark in turn by motion of his head. In another embodiment, a single fiducial 1906 can be placed at the location to be registered. A virtual circle 1908 can be used to define a mask whose position is controlled by the gaze of the user 106. The machine vision algorithm only looks for a single fiducial 1906 within the virtual circle 1908. Registration steps may be triggered with a voice command by the user 106 such as "register point." The user 106 may also register a point representing the distal femur such as the center of the patella or the medial and lateral epicondyles. When each point is registered, a virtual marker, such as a small sphere, may be positioned and remain at the location of the tip at the time of registration and beyond to provide the user 106 a visual confirmation to the user 106 and check on the quality of the registration.

Figure 20:
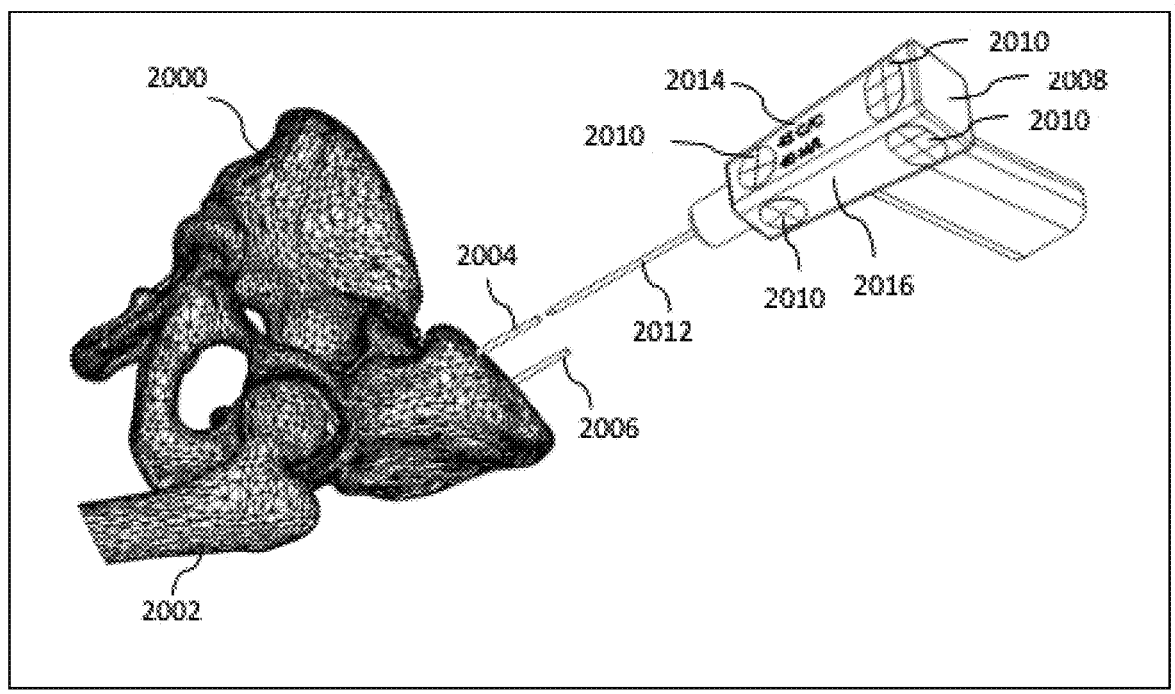
FIG. 20 is a diagrammatic depiction of a MXUI provided by system of FIG. 1 during insertion of a pin into a pelvis of a hip replacement procedure.

FIG. 20 depicts an exemplary embodiment of a MXUI shown to the user 106 via the display device 104 of a virtual pelvis 2000 and a virtual femur 2002 during a hip replacement procedure. If patient-specific models had been uploaded into the display device 104, then virtual models of these would be displayed along with any other virtual features of interest such as neurovascular structures. If not, the virtual pelvis and virtual femur could be gender-specific models, which have been scaled to best match the spacing of the registered landmarks. A first virtual trajectory 2004 and a second virtual trajectory 2006 for each of two fixation pins are displayed. In other embodiments, these may be tube-shaped or cone shaped. A drill 2008 is shown which includes a plurality of fiducials 2010 defining markers on a plurality of surfaces, which allows its pose to be tracked from various vantage points. Insertion of each pin can be guided either by lining up an actual pin 2012 with the virtual trajectory 2004 in the case where the drill is not tracked or by lining up a virtual pin (not shown) with the virtual trajectory in the case where the drill is tracked. If the drill is tracked, the angle of the drill relative to the pelvic reference frame is displayed numerically for additional augmentation. Virtual text 2014 is located on a surface 2016 of the actual drill and moves with the drill making it intuitive to the user the object to which the angles represented by the virtual text are associated.

Figure 21:
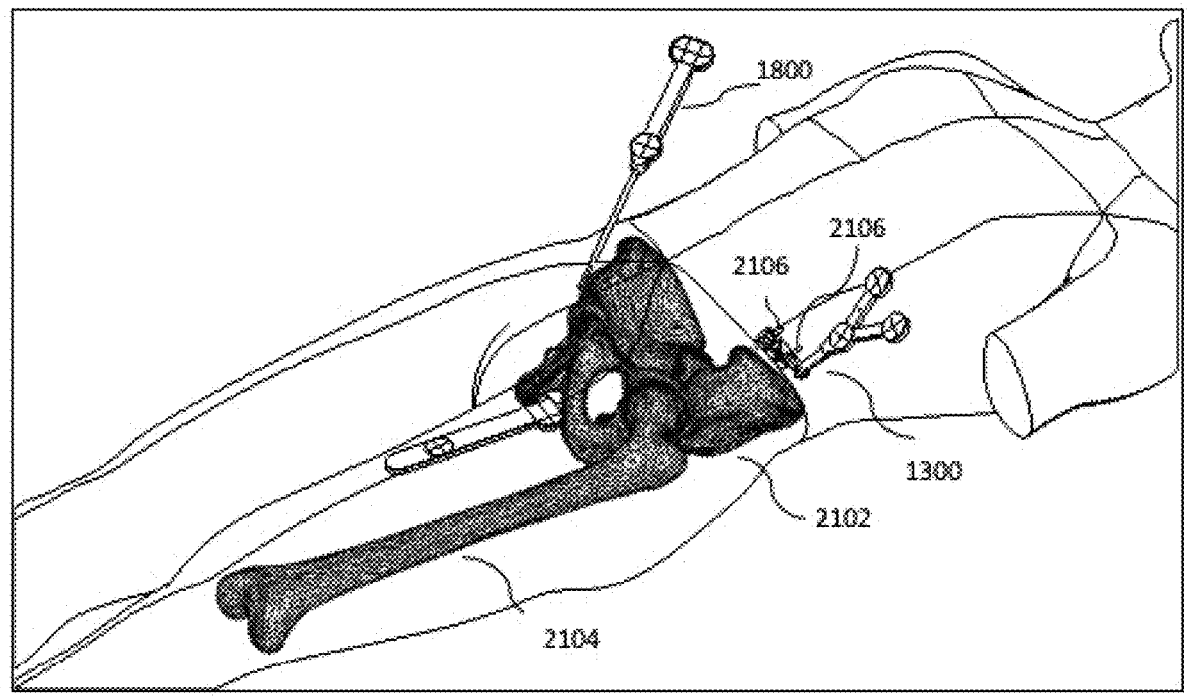
FIG. 21 is a diagrammatic depiction of a MXUI provided by system of FIG. 1 during a pelvic registration step of a hip replacement procedure.

FIG. 21 depicts an exemplary embodiment of a MXUI shown to the user 106 via the display device 104 during a hip replacement procedure with the anatomy marker 1300 attached to the patient's pelvis by way of clamping onto the pins 2106 inserted into the iliac crest. At this point, the reference frame relating to tracking the pelvis is transferred from the previous reference frame to that of the anatomy marker 1300. If desired, the pelvis may be re-registered to increase accuracy. The user 106 then makes an incision and exposes the femur using a virtual pelvis 2102, a virtual femur 2104, and virtual neurovascular structures (not shown) as a guide for the location of the incision and dissection of the muscles and joint capsule to expose the hip joint and neck of the femur. At this point, the user 106 places the leg in a reference position having approximately neutral abduction, flexion and rotation relative to the pelvis.

Figure 22:
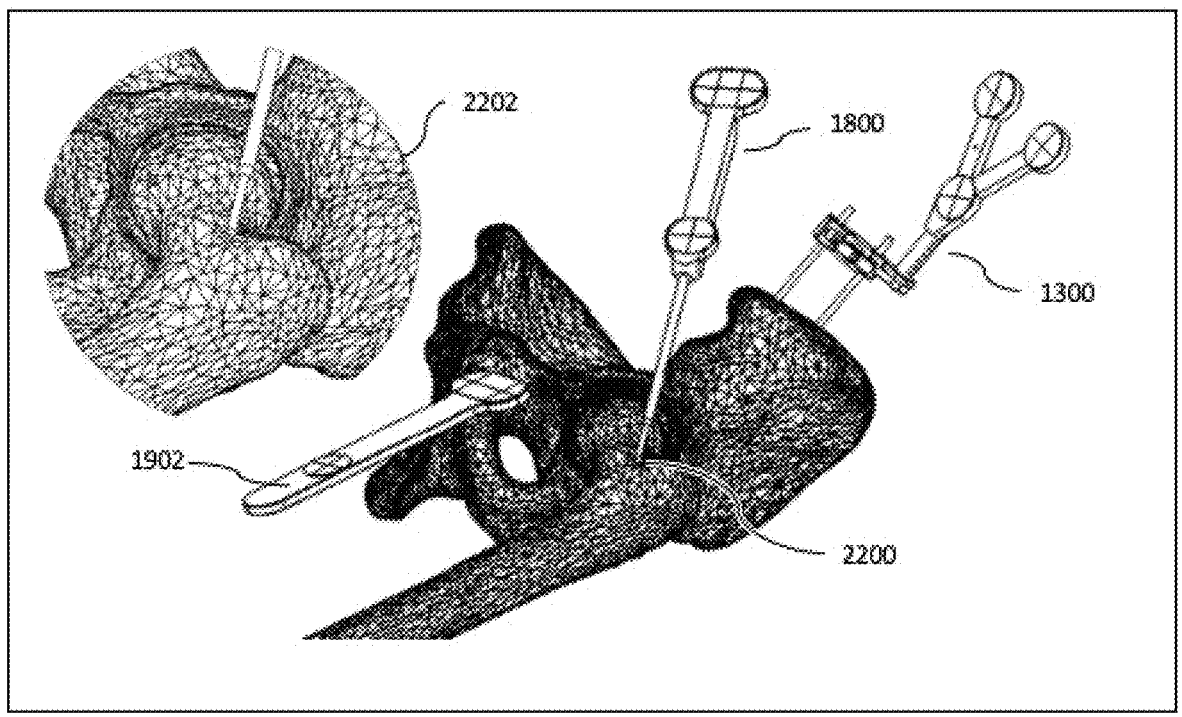
FIG. 22 is a diagrammatic depiction of a MXUI provided by system of FIG. 1 during a femoral registration step of a hip replacement procedure.

FIG. 22 depicts an exemplary embodiment of a MXUI shown to the user 106 via the display device 104 during femoral registration of a hip replacement procedure. The tip of the stylus 1800 is placed on a reference point 2200 on the proximal femur. At this time, the baseline orientation of the femur relative to the pelvis as defined by the relationship between markers 1902 and 1300 is determined and recorded. In addition, the coordinates of the reference point 2200 in the pelvic reference frame are recorded. The reference point 2200 may be enhanced by marking with a surgical pen, drilling a small hole in the bone or inserting a small tack. To improve the precision of the registration, a magnified stereoscopic image 2202 centered on the tip of the stylus is displayed as shown in FIG. 22. To aid the user 106 in finding the reference point later in the procedure, a baseline image, or images of the region around the point of the stylus may be recorded at the time of registration. These may be stereoscopic images. The user 106 then registers a point on the desired location of the femoral neck cut using the tip 1804 of the stylus 1800. This is typically the most superior/lateral point of the femoral neck. An optimum resection plane is calculated which passes through this point at the appropriate abduction and version angles.

Figure 23:
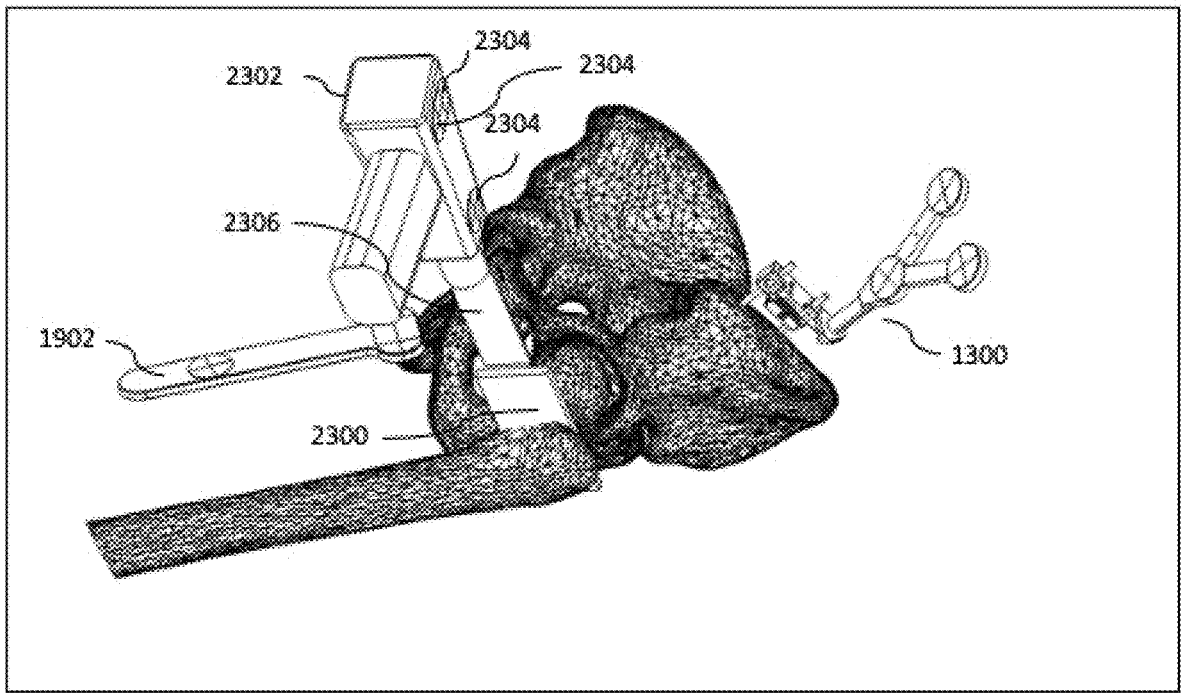
FIG. 23 is a diagrammatic depiction of a MXUI provided by system of FIG. 1 during resection of the femoral neck in a hip replacement procedure.

FIG. 23 depicts an exemplary embodiment of a MXUI shown to the user 106 via the display device 104 during resection of the femoral neck of a hip replacement procedure with a virtual resection guide 2300. A sagittal saw 2302 is shown having a plurality of fiducials 2304 defining a marker, allows the pose of the sagittal saw 2302 to be tracked. Resection of the femoral neck can be guided either by lining up the actual saw blade 2306 with the virtual resection guide 2300, in the case where the drill is not tracked, or by lining up a virtual saw blade (not shown) with the virtual resection guide 2300, in the case where the saw 2302 is tracked. As with the tracked drill shown in FIG. 20, the angles of the saw 2302 may be displayed numerically if the saw 2302 is tracked. These angles could be displayed relative to the pelvic reference frame or the femoral reference frame.

Figure 24:
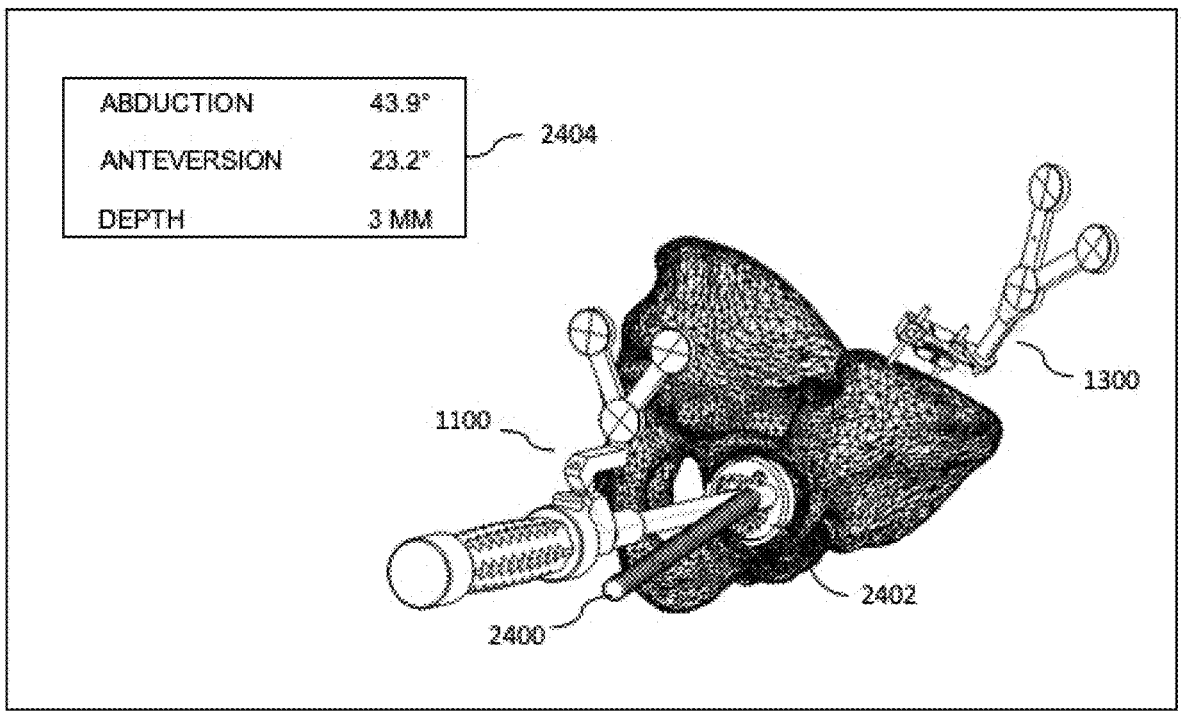
FIG. 24 is a diagrammatic depiction of a MXUI provided by system of FIG. 1 during positioning of an acetabular shell in a hip replacement procedure.

FIG. 24 depicts an exemplary embodiment of a MXUI shown to the user 106 via the display device 104 during positioning of the acetabular shell of a hip replacement procedure wherein a virtual target 2400 for the acetabular impactor assembly 1100 and a virtual shell 2402 are shown. Placement of the acetabular impactor assembly 1100 is guided by manipulating it to align with the virtual target 2400. The posterior/lateral quadrant of the shell portion of the virtual target may be displayed in a different color or otherwise visually differentiated from the rest of the shell 2402 to demarcate to the user 106 a target for safe placement of screws into the acetabulum. The numerical angle of the acetabular impactor and the depth of insertion relative to the reamed or un-reamed acetabulum are displayed numerically as virtual text 2404. A magnified stereoscopic image (not shown) similar to 2202 centered on the tip of the impactor may be displayed showing how the virtual shell interfaces with the acetabulum of the virtual pelvis 2102.

Figure 25:
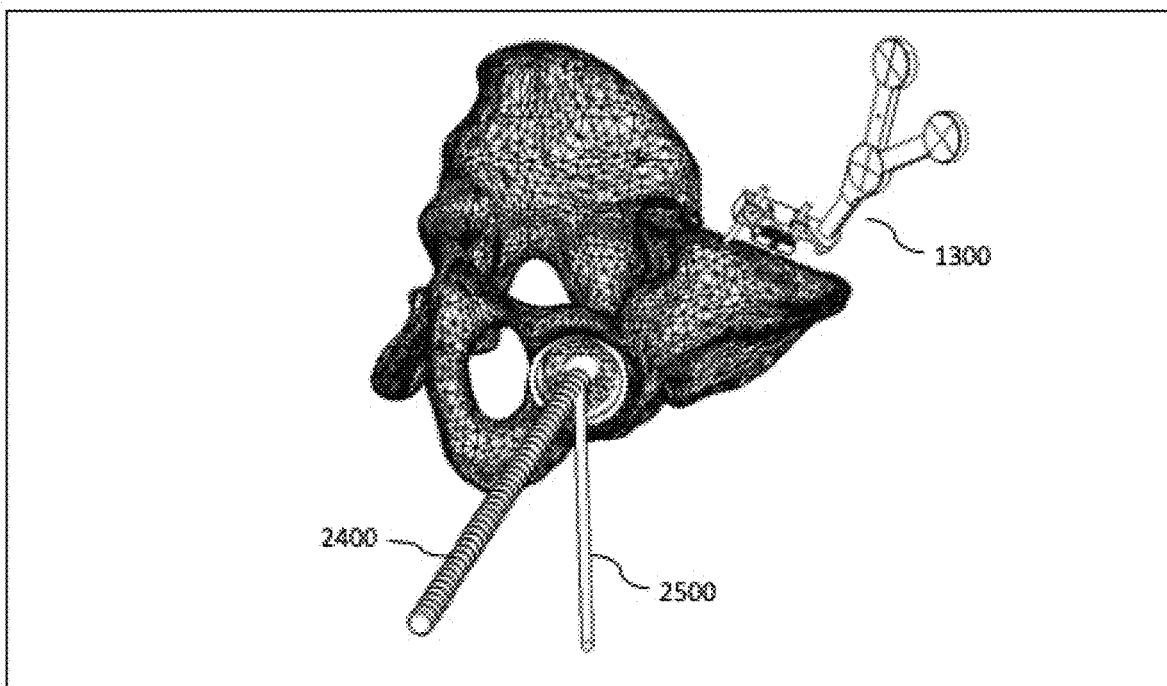
FIG. 25 is a diagrammatic depiction of a MXUI provided by system of FIG. 1 during positioning of an acetabular shell in a hip replacement procedure.

FIG. 25 depicts an exemplary embodiment of a MXUI shown to the user 106 via the display device 104 during positioning of the acetabular shell of a hip replacement procedure, wherein a virtual axis 2500 of the acetabular impactor and the virtual target 2400 are shown. Placement of the acetabular impactor is guided by manipulating it to align the virtual axis 2500 with the virtual target 2400.

Figure 26:
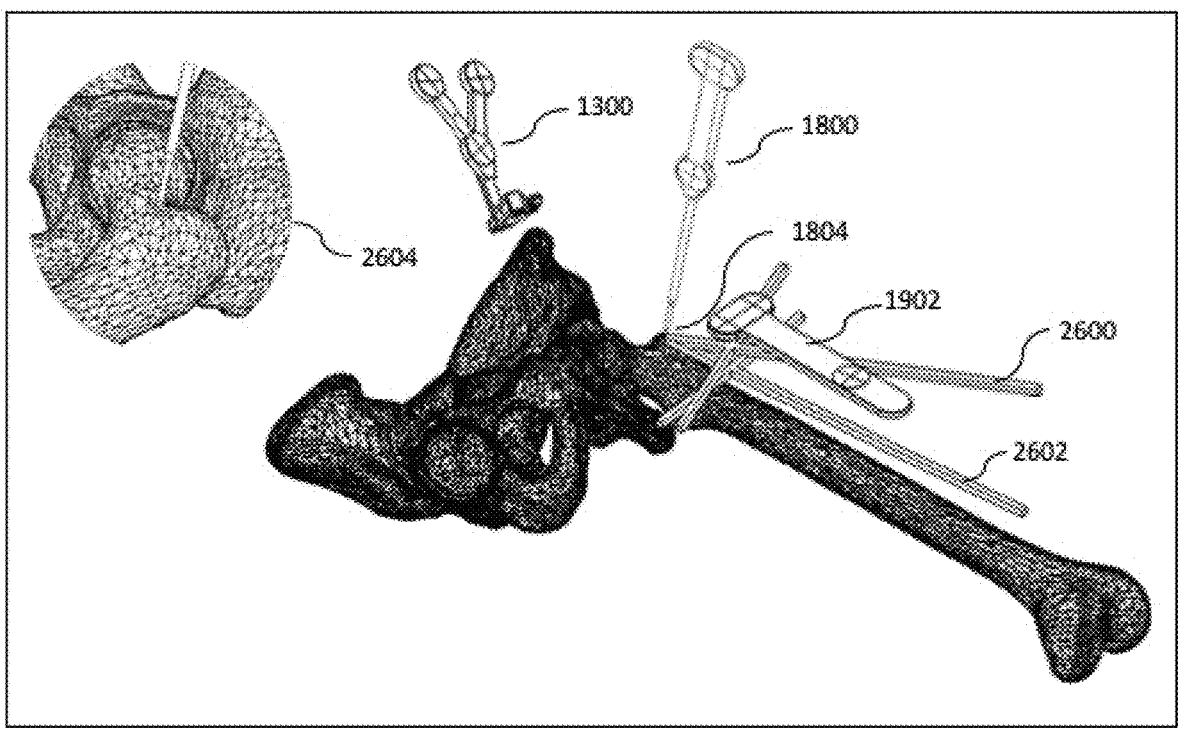
FIG. 26 is a diagrammatic depiction of a MXUI provided by system of FIG. 1 during repositioning of the femur in a hip replacement procedure.

FIG. 26 depicts an exemplary embodiment of a MXUI shown to the user 106 via the display device 104 during repositioning and registration of the femur of a hip replacement procedure. A virtual femur target 2600 is shown which represents the preoperative orientation of the femur relative to the pelvis during baseline femoral registration. The superior apex of this virtual femur target is placed near the reference point on the proximal femur. A virtual femur frame 2602 is shown which represents the current orientation of the femur. As the femur is moved, the virtual femur frame 2602 rotates about the superior apex of the virtual femur target 2600. Re-positioning the femur to the baseline orientation is achieved by manipulating the femur to align the virtual femur frame 2602 with the virtual femur target 2600 in abduction, flexion, and rotation. With the femur re-positioned in the baseline orientation, the user then uses the tip 1804 of the stylus 1800 to re-register a reference point on the proximal femur to determine the change in leg length and lateral offset from the baseline measurement. The baseline image 2604 recorded earlier during baseline femoral registration may be displayed to assist in precisely re-registering the same reference point.

Figure 64:
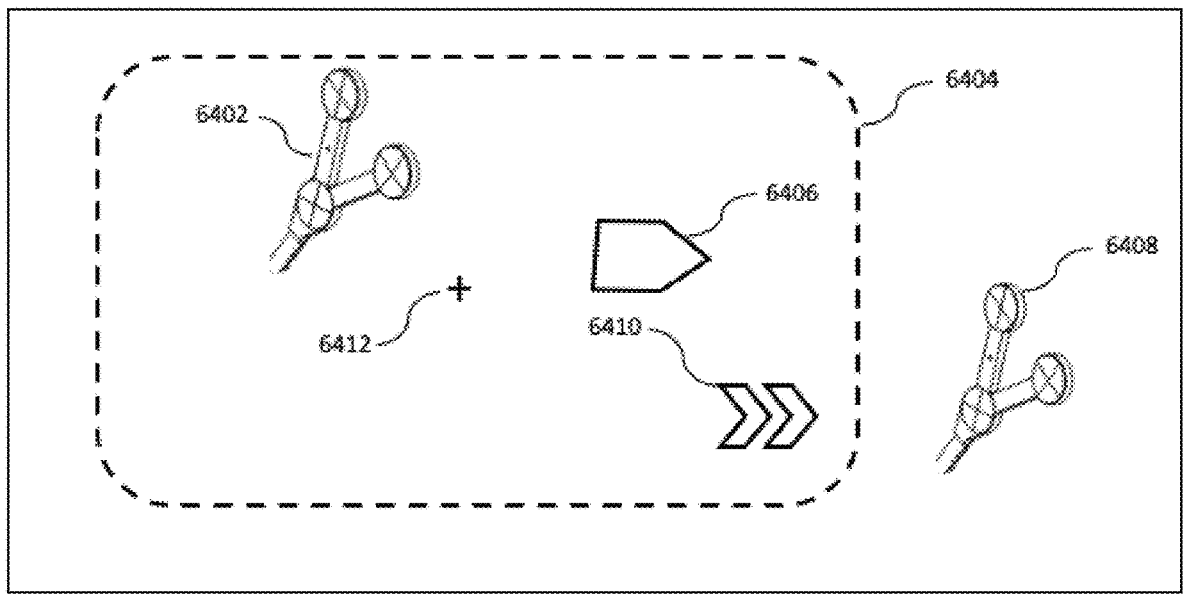
FIG. 64 is a diagrammatic depiction of a MXUI illustrating features to assist the user in positioning the camera FOV to encompass required markers.

In some applications, it may be advantageous to use cameras with a relatively small field of view to effectively decrease the size of the available pixels in order to maximize tracking accuracy. As a result, it becomes more difficult for the user to position the camera(s) so all required markers fall within the field of view, especially since it may not be obvious to the user which markers are or are not inside the field of view, or in which direction the camera(s) should be directed to capture all required markers. FIG. 64 depicts an exemplary embodiment of a MXUI with features designed to assist the user in positioning the field of view of the camera(s) to contain all required markers. In this embodiment, two markers 6402 and 6408 are required to be tracked by camera(s) to register a point or calculate navigation outputs. One marker 6402 is located within field of view 6404 of camera(s). A second marker 6408 is outside field of view 6404 of the camera(s). A virtual guide 6410 is displayed to user 106 in display device 104, indicating the direction in which missing marker 6408 is likely to be found. Virtual guide 6410 may be a symbol, such as an arrow, or text indicating a direction. In one embodiment, the expected location of marker 6408 is based on the relative positions of markers 6402 and 6408, which were either previously recorded when both markers were visible, or estimated by the system based on typical marker placement. For many applications, markers can reasonably be expected to move only small distances once they are set up for a particular procedure. For example, two markers mounted on the pelvis and the thigh during a hip replacement surgery will stay in roughly the same relative positions throughout the surgery. In this case, the system, having once detected the two markers simultaneously and measured their relative locations, can indicate to the user the direction of the missing marker if either marker is in the camera field of view 6404. Similarly, knowledge of typical anatomy informs the system about likely positions of markers. For example, markers placed by the user on the iliac crest on the pelvis and on the anterior aspect of the thigh of a hip replacement patient will always be roughly the same distance apart, and in roughly the same direction. In a simple example, an assumption that a second marker 6408 would be positioned approximately along the positive x-axis of a first marker 6402 would enable the system to generate a useful virtual guide 6410 directing the user to shift the camera field of view 6404 along that axis. In another embodiment, for example where no markers are in a camera field of view, inertial sensors in sensor suite are used to track the movement of the head of user (e.g., head angle) and calculate the relative position of marker 6408 based on its last known position (e.g., from the current head position and/or angle) when it fell within camera field of view 6404. In one embodiment, a virtual control 6406 is shown to the user via the display device mounted on the head of user. The user must activate virtual control 6406 (for example, to register a point) by moving his or her head to align a fixed reticle or cursor or user input control 6412 with virtual control 6406. In this embodiment, virtual control 6406 is positioned by the system relative to marker 6402 to center it between the two required markers 6402 and 6408, and the position of the virtual control 6406 is adjusted as the user turns his/her head to align the user input control 6412 with the virtual control 6406 until they are aligned. As user turns his head to align user input control 6412 with virtual control 6406, camera field of view 6404 moves or adjusts to encompass both markers 6402 and 6408, thereby allowing tracking of the at least two markers in the field of view of the camera.

Figure 50A:
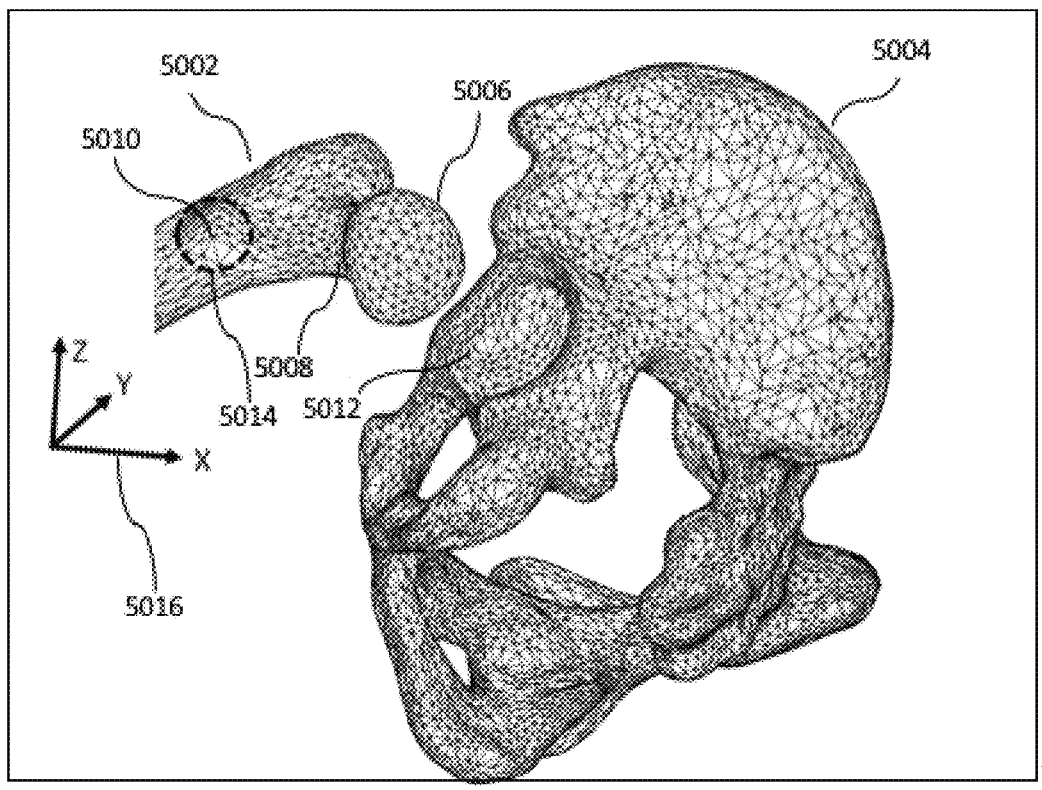
FIG. 50A is a diagrammatic depiction of exposed surfaces on the acetabulum and proximal femur in a reference position.
Figure 50B:
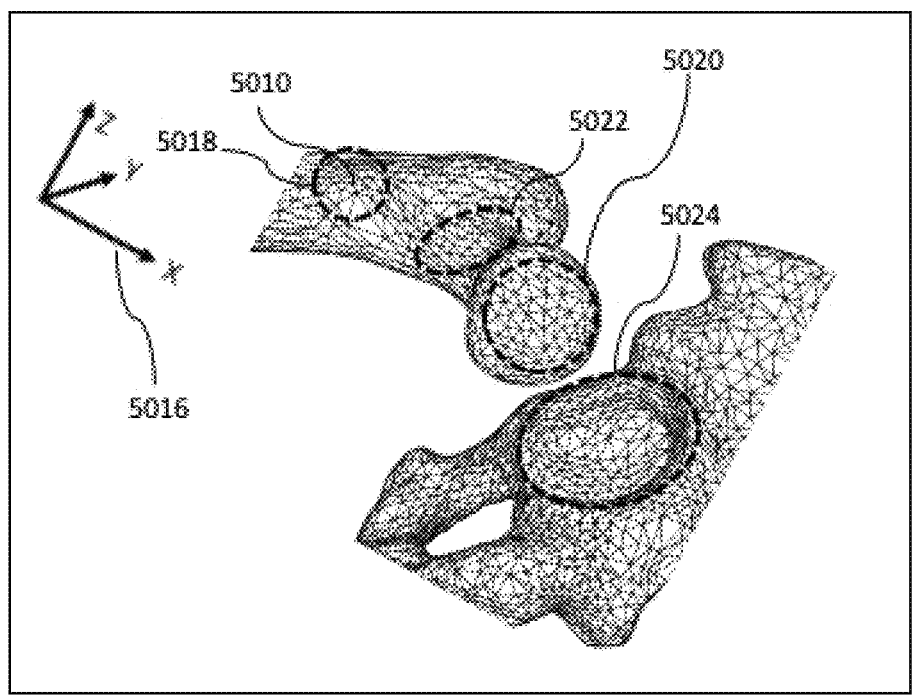
FIG. 50B is a diagrammatic depiction of exposed surfaces on the acetabulum and proximal femur in a displaced position.
Figure 51:
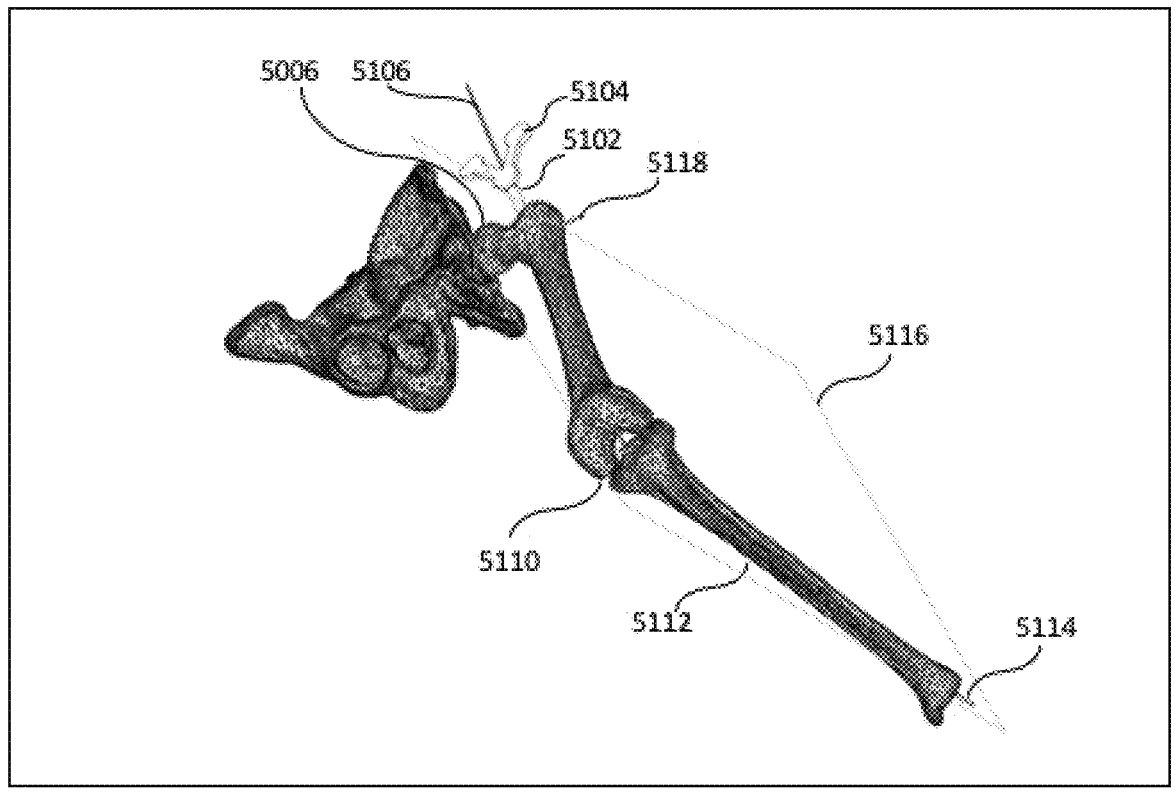
FIG. 51 is a diagrammatic depiction of a hip and leg, showing reference axes and planes for calculating femoral version.
Figure 52:
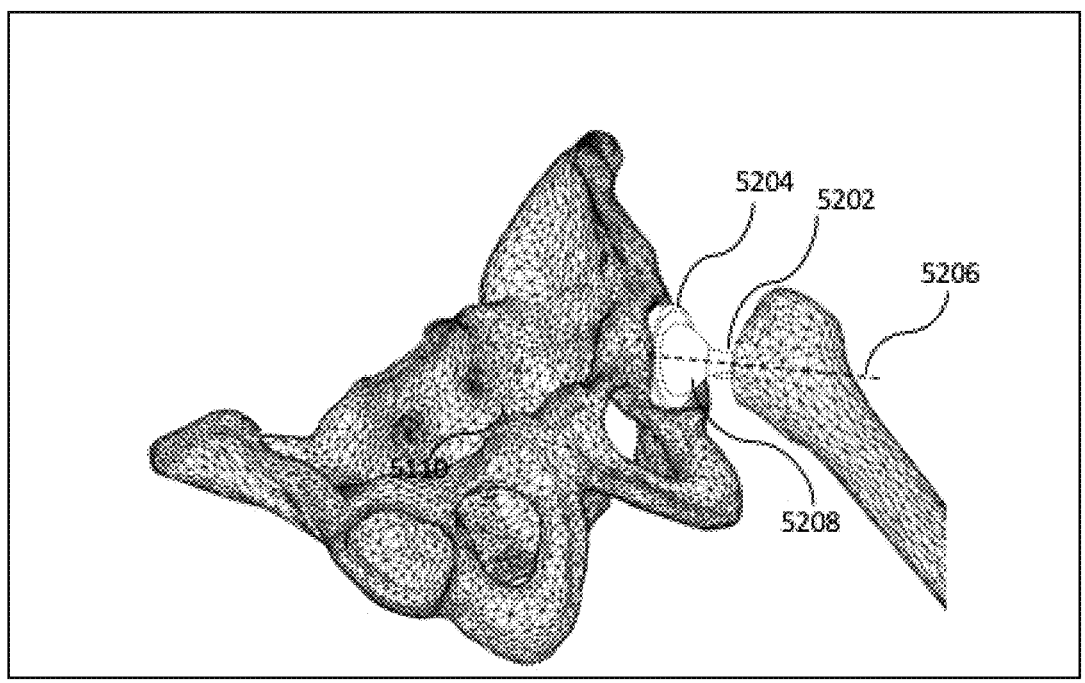
FIG. 52 is a diagrammatic depiction of a hip with implanted components.

Referring to FIGS. 50-52, the system 10 may optionally include a means for tracking anatomic structures without external fiducials fixed to the anatomy. FIGS. 50A-B depict an exemplary embodiment, in which the femur 5002 is dislocated, allowing the system 10, using sensor suite 210, to create a reference 3-dimensional surface map 5014 of the exposed surface of the lesser trochanter 5010. The surface of the lesser trochanter remains unchanged throughout the procedure and may be used by the system 10 to track the femur without additional fiducials. The boundary of the reference 3-dimensional surface map 5014 may optionally be indicated by the user by tracing a curve using a cursor or pointing device, which may operate by tracking the user's gaze. The system 10 may store the reference 3-dimensional map 5014 as a point cloud, as mathematical surfaces, or by other means. The system 10 may create a reference frame 5016 relative to the sensor suite 210 and record the initial pose of the surface map 5014 in reference frame 5016. The user 106 may register additional reference points or structures on the same bone or rigid body, such as the femoral head 5006, femoral neck 5008, and acetabulum 5012. The system may create additional 3-dimensional surface maps 5020, 5022, 5024 for the femoral head, femoral neck, and acetabulum, respectively, whose pose the system 10 records relative to the reference frame 5016. The system 10, using sensor suite 210, continuously re-scans the lesser trochanter 5010 and generates a displaced 3-dimensional surface map 5018 of the anatomy. Then comparing the displaced 3-dimensional surface map 5018 to the reference 3-dimensional surface map 5014 created for the same surface, the system 10 determines the geometric rotation and translation required to align the displaced surface map 5018 and reference surface map 5014 for best fit. The system 10 then applies the same rotation and translation to all stored reference points and structures on the rigid body of the femur 5002, calculating the current pose of all such points and structures relative to the reference frame of sensor suite 210. The system 10 may calculate diameter of the femoral head 5006 or acetabulum 5012 and display it to the user 106 as a guide for selecting an acetabular reamer size. The system 10 may calculate the center of the femoral head 5006 relative to the reference surface map 5014. The system 10 may also calculate the position of the center of the acetabulum 5012 relative to the pelvis 5004. The user 106 then inserts a broach or reamer 5102 with attached fiducial 5104 into canal of the femur, identifying a femoral axis 5106. The system 10 calculates a femoral neck axis 5118 between the femoral head 5006 and femoral axis 5106. With the knee 5110 flexed to approximately 90°, the cameras 206 scan the lower leg 5112, identifying its approximate central axis 5114, which is used with the femoral axis 5106 to define a reference plane 5116 from which the version angle of the native femoral neck axis 5118 is calculated. In the course of the procedure, the native femoral head 5006 and acetabulum 5012 are replaced with a femoral implant 5202 and acetabular implant 5204, respectively. The system 10 may detect the centers of the implanted acetabular shell 5204 and femoral head 5208, allowing the system 10 to calculate and display the change in distance from the femoral axis 5106 to the femoral head 5208 (femoral offset), or the change of position of the center of the acetabulum 5208, between the respective native and implanted conditions of each structure. Following replacement of the femoral head 5006, but prior to replacement of the acetabulum 5012, the system 10 may calculate and display the femoral version based on a new calculation of the femoral neck axis 5206 using the replaced femoral head 5208. The system 10 may calculate and display the additional anteversion required in the acetabular implant 5204 to achieve a target for combined anteversion of the femoral implant 5202 and acetabular implant 5204. The system 10 may calculate and display a change in distance between the femur 5002 and pelvis 5004 arising as a result of the procedure.

Figure 53:
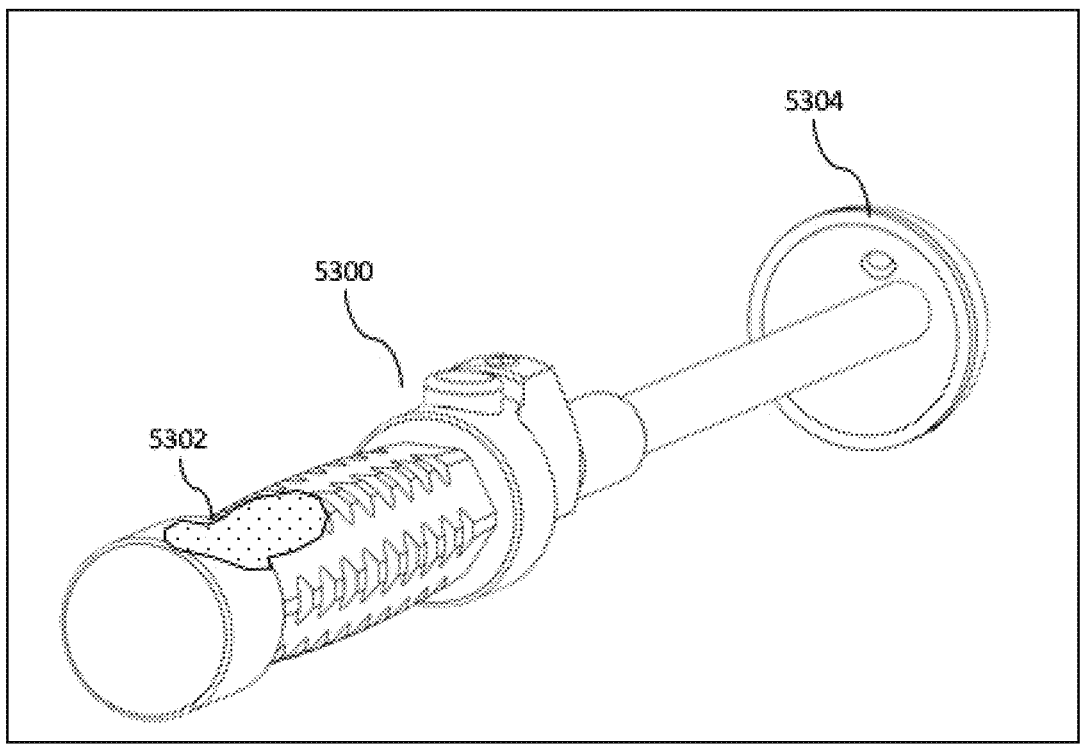
FIG. 53 is a diagrammatic depiction of a hip impactor and shell showing surfaces mapped on the impactor.

FIG. 53 depicts an exemplary embodiment of a hip impactor 5300 tracked via a 3-dimensional map of a portion of its exposed surface 5302, rather than by means of a supplementary fiducial. The system 10 may register an acetabular shell 5304 to this surface by simultaneously scanning the shell 5304 and impactor surfaces using the cameras 206.

Figure 59:
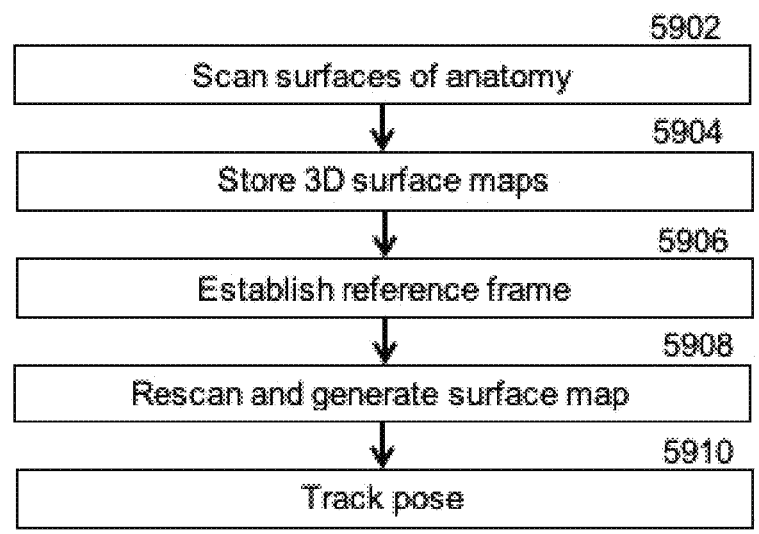
FIG. 59 is a flowchart showing an exemplary method of navigating a hip replacement procedure.

FIG. 59 depicts a flowchart showing how the system 10 and its sensor suite 210 can be used for navigation in a hip arthroplasty procedure. The sensor suite 210 can scan the lesser trochanter 5010 (5902). From this scan, reference 3-dimensional surface map 5014 can be stored (5904). The system 10 can then establish a reference frame 5016 for the femur 5002 relative to the sensor suite 210 (5906). Then, repeatedly scanning the exposed lesser trochanter 5010, the system 10 generates a displaced 3-dimensional surface map 5018 for each scan (5908). With each successive scan, the system can compare the displaced surface map 5018 to the reference surface map 5014 for the same region on the lesser trochanter 5010. Based on this comparison, the system 10 can track the pose of the femur 5002 relative to sensor suite 210 by determining the translation and rotation required to best fit the displaced surface map 5018 with the reference surface map 5014 (5910).

Figure 54:
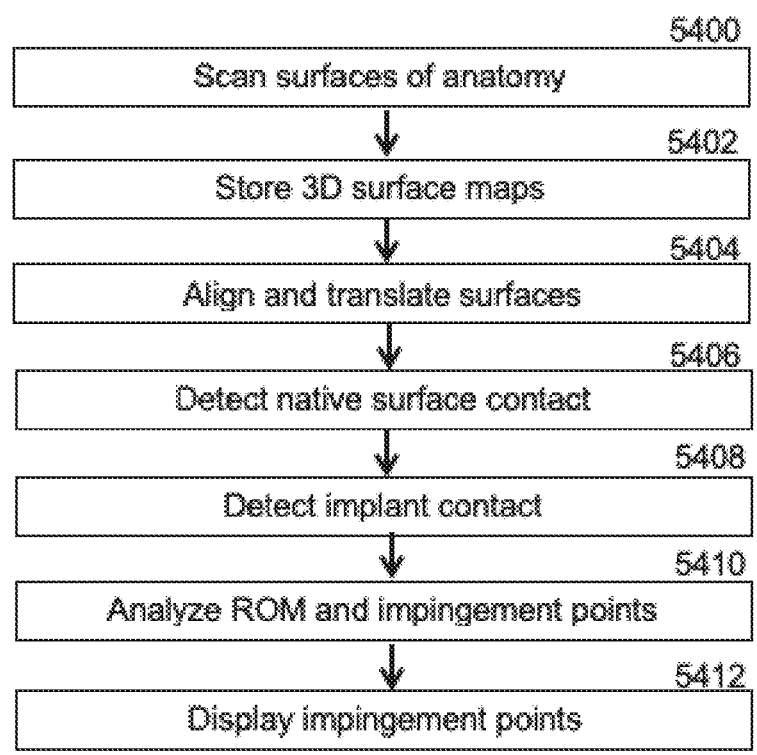
FIG. 54 is a flowchart showing how the system of FIG. 1 can be used to analyze hip kinematics in accordance with the principles of the present invention.

FIG. 54 depicts a flowchart showing how the system 10 and its sensor suite 210 can be used to analyze hip kinematics. The sensor suite 210 can scan exposed surfaces of the patient's anatomy, including the native femoral head 5006 and acetabulum 5012 (5400). From these surfaces, 3-dimensional maps 5020,5024 of each structure can be stored (5402). The system 10 can then rotate the surfaces into the orientations expected in a standing patient and translate them together in the direction of body weight (5404). The system 10 can then calculate the contact point or patch between the two surfaces, which may be a more appropriate center of rotation than the centers of the approximately spherical surfaces (5406). Following replacement of the native anatomy with femoral implant 5202 and acetabular implant 5204, the system 10 can similarly identify the contact points for the implants (5408). Using the implant geometry, the system 10 can perturb the hip angle to calculate the angular range of motion allowed in each direction prior to impingement between implants, or between implants and bone (5410). The location of first impingement, which limits range of motion, can be highlighted in the display device 104 (5412). For example, the femoral neck 5008 may impinge on the exposed rim of the acetabulum 5012, or on the acetabular implant 5204. If at least one of the impinging surfaces is on native bone, the user 106 may elect to trim the bone to increase the range of motion. If at least one of the impinging surfaces is on an implant, the user 106 may elect to adjust the position or angle of the implant.

IV. Use of System in Conjunction with a C-Arm System

Figure 27:
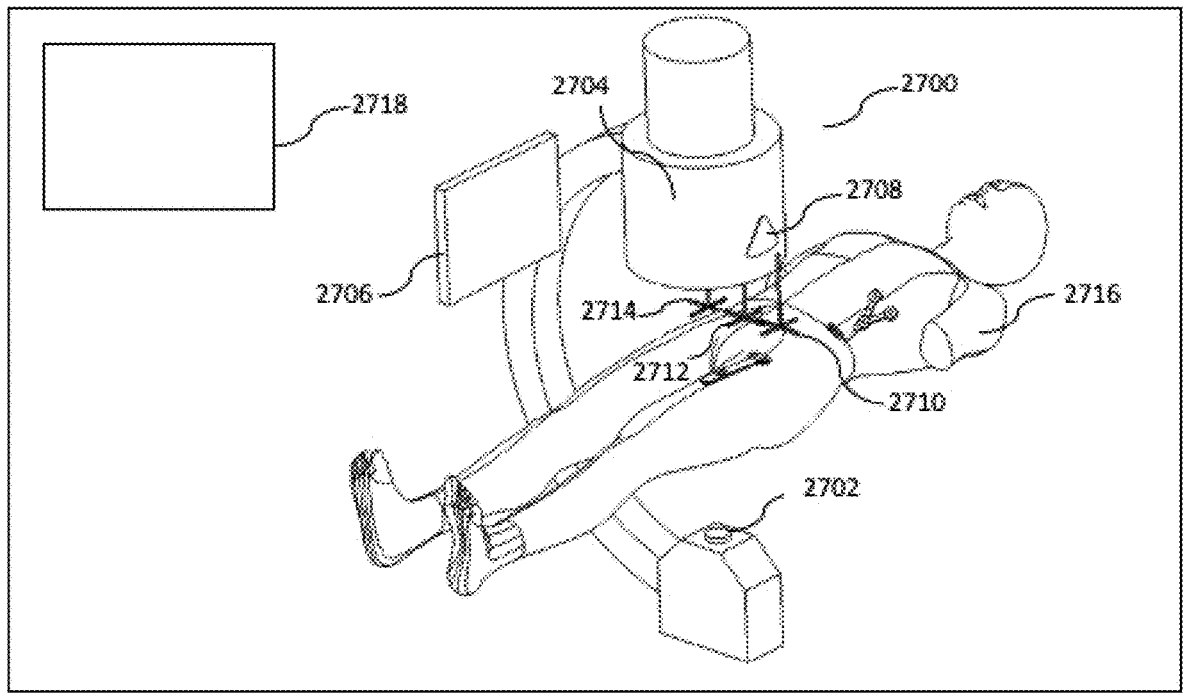
FIG. 27 is a diagrammatic depiction of a MXUI provided by system of FIG. 1 using a C-arm during a hip replacement procedure.

FIG. 27 depicts an exemplary embodiment of a MXUI shown to the user 106 via the display device 104 during imaging of a patient with a C-arm. A C-arm imaging system 2700 is shown having an X-ray source 2702, an imaging unit

2704 and a display unit 2706. A trackable label 2708 has been attached to the C-arm 2700. A virtual hip alignment guide 2710 and a virtual pelvis alignment guide 2712 are shown. These are perpendicular to the anterior pelvic plane and centered over the hip joint and pubic symphysis, respectively. Placement of the C-arm 2700 is guided by adjusting the surface of the imaging unit 2704 to be aligned with the appropriate virtual alignment guide. If the C-arm 2700 is trackable, then a virtual C-arm alignment guide 2714 may be displayed. In this case, placement of the C-arm 2700 is guided by adjusting the virtual C-arm alignment guide 2714 to be aligned with the appropriate virtual alignment guides 2710 or 2712. The positional and angular misalignment relative to the target can also be displayed numerically as virtual text 2718.

Figure 28:
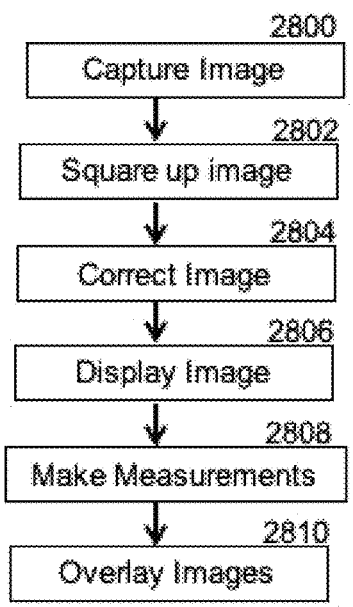
FIG. 28 is a flowchart showing how the system of FIG. 1 can be used in conjunction with a C-arm in a surgical procedure in accordance with the principles of the present invention.

FIG. 28 depicts a flowchart showing how the system 10 and its display device 104 (e.g., the AR headset 3600) can be used in conjunction with the C-arm 2700 in a surgical procedure. The camera 3904 (e.g., a high definition camera or the like) incorporated in the AR headset 3600 can be used to capture the image displayed on the C-arm monitor (2800). The image can be adjusted to "square it up" so that it matches what would be seen if the camera 3904 had been perfectly centered on and normal to the image on the monitor (2802). The knowledge of the position of the imager and source relative to the anatomy being imaged can be used to correct images for magnification and parallax distortion due to divergence of the X-ray beam from the source (2804). The corrected image can then be displayed in the AR headset 3600 (2806). This can then be used to allow the user 106 to make measurements relevant to the procedure such as acetabular cup placement or leg length (2808). Other images can be simultaneously displayed, overlaid, mirrored, or otherwise manipulated to allow the user 106 to make comparisons as shown, at least for example, in block 2810 of FIG. 28.

In another embodiment, image capture can also be achieved by wireless communication between the C-arm 2700 and the AR headset 3600, for example by transfer of file in DICOM format. Alternatively, algorithms incorporating machine vision could be employed to automatically make measurements such as the inclination and version of an acetabular shell. Edge detection can be used to trace the outline of the shell. The parameters of an ellipse, which optimally matches the outline, can be determined and used to calculate the anteversion of the shell from the ratio of the length of the minor and major axes of the optimum ellipse. The inclination can be calculated, for example, by placing a line tangential to the most inferior aspects of the pubic rami and calculating the angle between the major axis of the shell ellipse and the tangential line. Similarly, the comparative leg length and lateral offset of the femur can be determined and could be corrected for changes or differences in abduction of the femur by recognizing the center of rotation from the head of the femur or the center of the spherical section of the shell and performing a virtual rotation about this point to match the abduction angles. This type of calculation could be performed almost instantaneously and save time or the need to take additional radiographic images. Furthermore, and in another embodiment, an algorithm could correct for the effect of mispositioning of the pelvis on the apparent inclination and anteversion of the shell by performing a virtual rotation to match the widths and aspect ratios of the radiolucent regions representing the obturator foramens.

In yet another embodiment, C-arm imaging can be used to register the position of anatomy, such as the pelvis. For this, the anatomy marker 1300 would incorporate radio-opaque features of known geometry in a known pattern. The C-arm image is captured and scaled based on known marker features and displayed in the AR headset 3600. A virtual model of the anatomy generated from a prior CT scan is displayed to the user 106. The user 106 can manipulate the virtual model to position it in a way that its outline matches the C-arm image. This manipulation is preferably performed by tracking position and motion of the user's 106 hand using SLAM. Alternatively, the user 106 can manipulate a physical object, which incorporates a marker with the virtual model moving with the physical object. When the virtual model is correctly aligned with the C-arm image, the relationship between the patient's anatomy and the anatomy marker 1300 can be calculated. These steps and manipulations could also be performed computationally by the software by using edge detection and matching that to a projection of the profile of the model generated from the CT.

Due to the limited size of available C-arms, it may be difficult or impossible for the user to position the C-arm in such a way as to image the entire anatomy of interest. For example, the user may want to capture an image of a pelvis 14 inches wide, but only has access to a C-arm capable of imaging a 10-inch diameter field of view. This problem is compounded by distortion near the edges of C-arm images, effectively reducing the usable image size. Although algorithms exist to stitch together multiple images based on identifying and aligning shared features in each image, these techniques depend on overlap between images to create shared features for registration. For example, a user with a 10-inch C-arm would need to acquire at least four (and very likely more) overlapping images to create an image showing two anatomic features 36 inches apart in their correct anatomic alignment. In another embodiment of the present invention, the system can be used to digitally stitch multiple images from C-arm 2700 to create an image of a larger portion of the patient 2716 without overlap between images. For each image captured by C-arm 2700, AR headset 3600 measures the corresponding position of C-arm 2700 relative to patient 2716 using a tracker such as label 2708. The system then displays the collected images on display 2706 or AR headset 3600 with each image in its correct position and alignment relative to the common reference frame, allowing the user 106 to view and make measurements on a virtual image including a larger portion of patient 2716 than could fit in a single image, such as imaging a complete pelvis with a C-arm 2700 whose image size is less than the extent of a complete pelvis, or viewing a single image of a hip and a single image of an ankle in anatomic alignment. This feature is useful for evaluating alignment and/or length of limbs, spine, etc. while minimizing radiation from the imaging system.

V. Spinal Procedures

Figure 31:
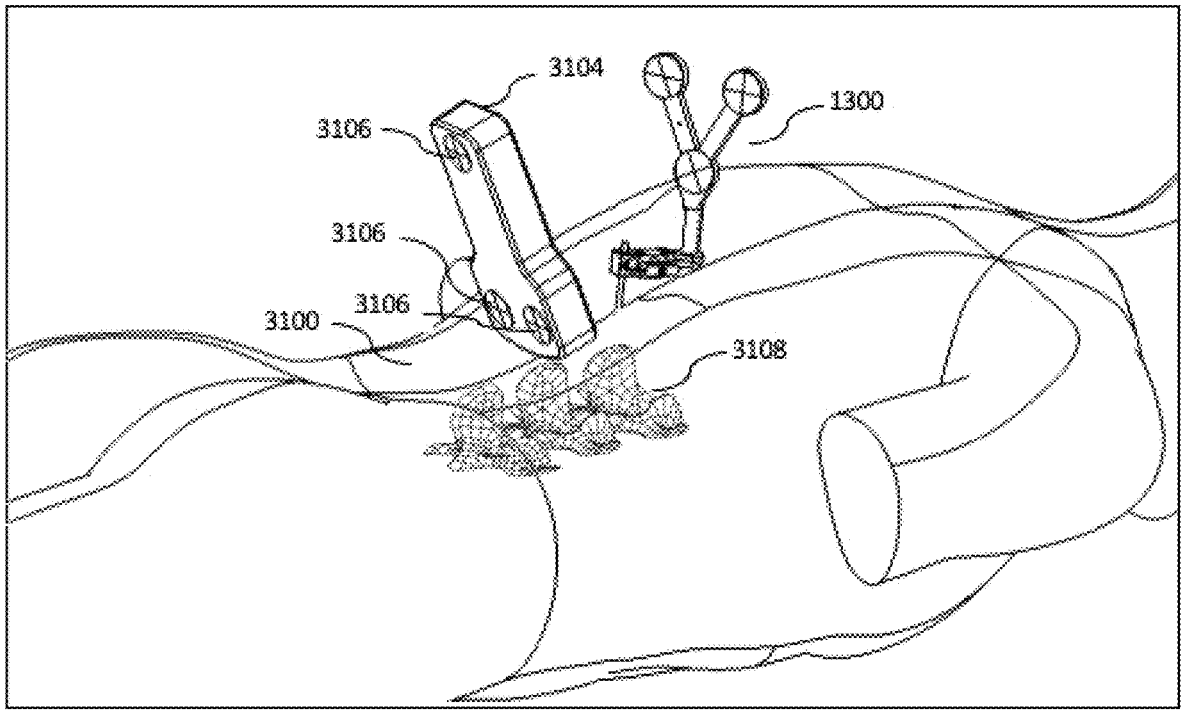
FIG. 31 is a diagrammatic depiction of a MXUI provided by system of FIG. 1 during registration of a spine with an ultrasound transducer in a spinal fusion procedure.

FIG. 31 depicts an exemplary embodiment of a MXUI shown to the user 106 via the display device 104 during registration of a spine with ultrasound. An anatomy marker 1300 is fixated to a vertebra adjacent to the operative site. An ultrasound transducer 3104 which includes a plurality of fiducials 3106 defining a marker is provided. In one embodiment, the ultrasound transducer 3104 is battery operated, cordless, and can communicate with the AR headset 3600 via radio. The software has geometric and other information necessary to be able to position and scale the 2D ultrasound image relative to the marker's 1300 position. The ultrasound transducer 3104 is moved over the surface of the patient 3100 to scan the region of interest. The software combines the 2D image data with the six degree of freedom pose information of the ultrasound transducer 3104 relative to the anatomy marker 1300 to generate a virtual model 3108 representing the surface of the vertebrae of interest. The ultrasound transducer 3104 may be rotated relative to anatomy of interest to get a more complete 3D image. The posterior contour of the spinous process and the left and right mammillary processes can be matched to the same features of a CT generated 3D model of the vertebra to register and subsequently position the virtual model of the vertebra in a mixed reality view. Alternatively, any appropriate features which are visible on an ultrasound scan can be utilized or the position of the virtual model can be relative to the surface of the patient as determined by SLAM. The latter is appropriate for procedures in which the patient anatomy of interest is stationary for the duration of the procedure and attachment of a marker would be unnecessarily invasive or burdensome. Ultrasound can similarly be used in this way to generate models of anatomy of interest such as, but not limited to, bony structures, nerves and blood vessels. Registration of any anatomy can be achieved. For example, a pelvic reference frame can be established using ultrasound to locate the proximal apex of the left and right ASIS and the pubis. The same method can be used to track the position of tools or implants percutaneously.

Figure 32:
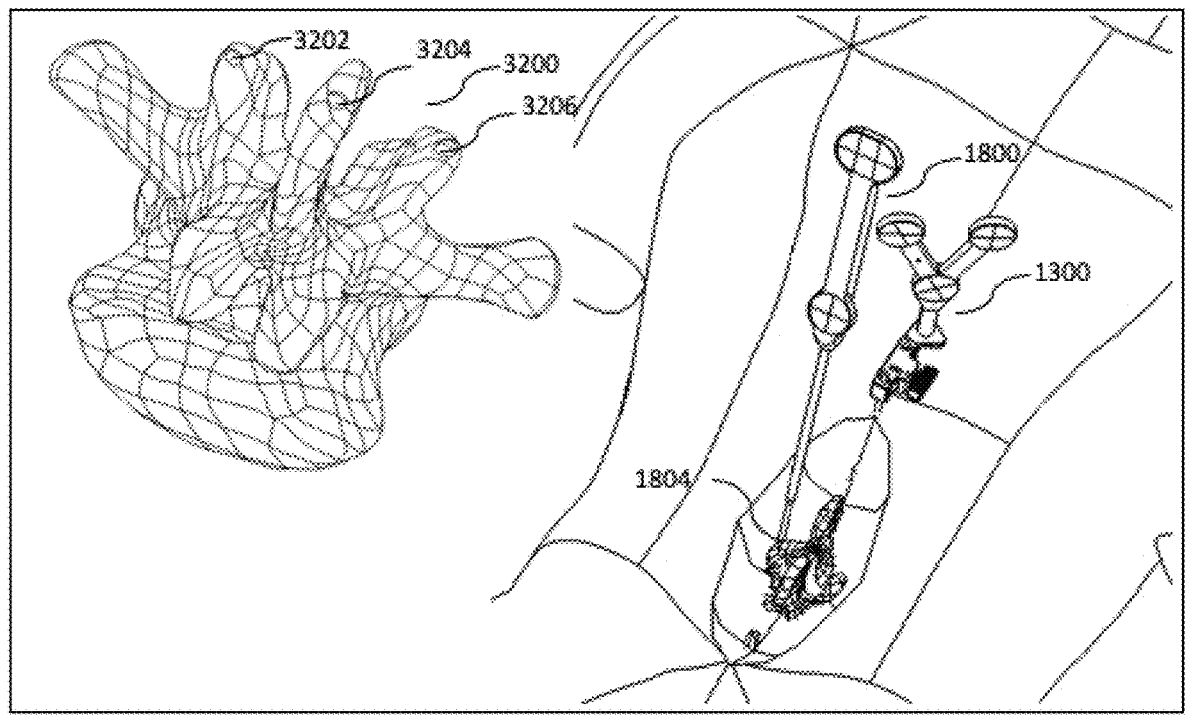
FIG. 32 is a diagrammatic depiction of a MXUI provided by system of FIG. 1 during registration of a spine with a stylus in an open spinal fusion procedure.
Figure 33:
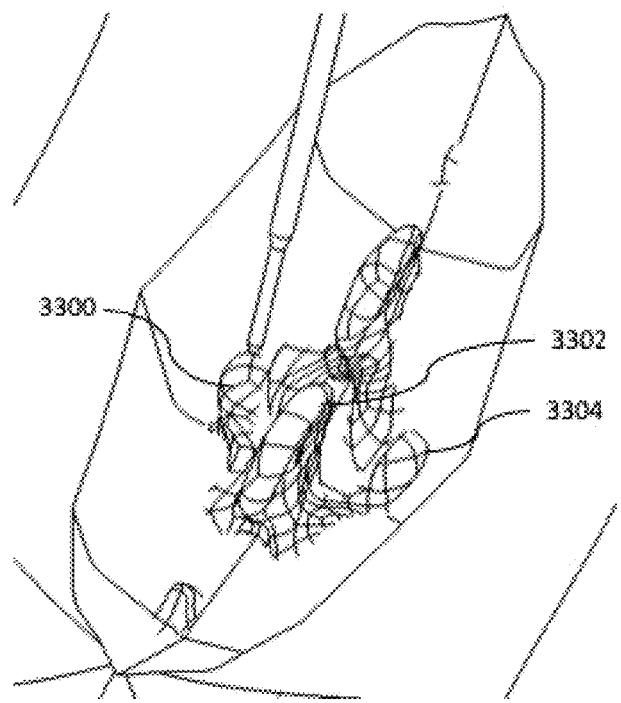
FIG. 33 is a close-up front view of the surgical exposure portion of FIG. 32.

FIG. 32 depicts an exemplary embodiment of a MXUI shown to the user 106 via the display device 104 during registration of a spine with a stylus 1800. The anatomy marker 1300 is fixated to a vertebra adjacent to the operative site. A virtual model 3200 of the patient's vertebra generated from pre-operative imaging is displayed. This virtual model includes a first landmark 3202, a second landmark 3204, and a third landmark 3206. FIG. 33 depicts a close-up view of the exposed anatomy shown in FIG. 32. The soft tissues of the patient have been dissected sufficiently to expose a first bony process 3300, a second bony process 3302, and a third bony process 3304, which contain the three landmarks. The user 106 registers the three landmarks by placing the stylus tip 1804 at the points on the actual vertebra that best match the location of the landmarks shown on the virtual model. The software then re-positions the virtual model 3200 in the user's view to best align these points. The user 106 visually verifies the quality of the registration by comparison of the virtual model to the actual exposed regions of the vertebra. If necessary, the user 106 may make adjustments by using the tip 1804 of the stylus 1800 to reposition the virtual model. In an alternative embodiment, the landmarks are arcs traced over the most posterior aspect of each process. In another embodiment, the contours of the exposed processes are established with SLAM, and the software performs a best fit on the position of the virtual model to match these contours.

Figure 34:
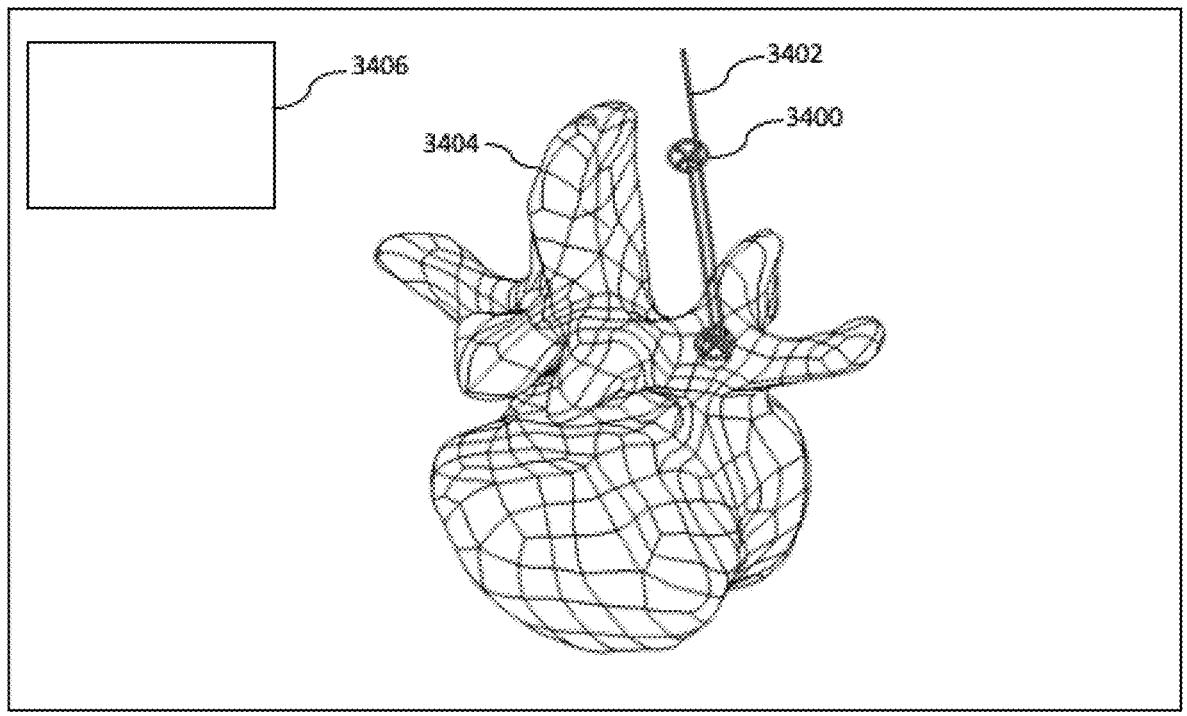
FIG. 34 is a diagrammatic depiction of a MXUI provided by system of FIG. 1 during drilling of a pedicle in a spinal fusion procedure.
Figure 35:
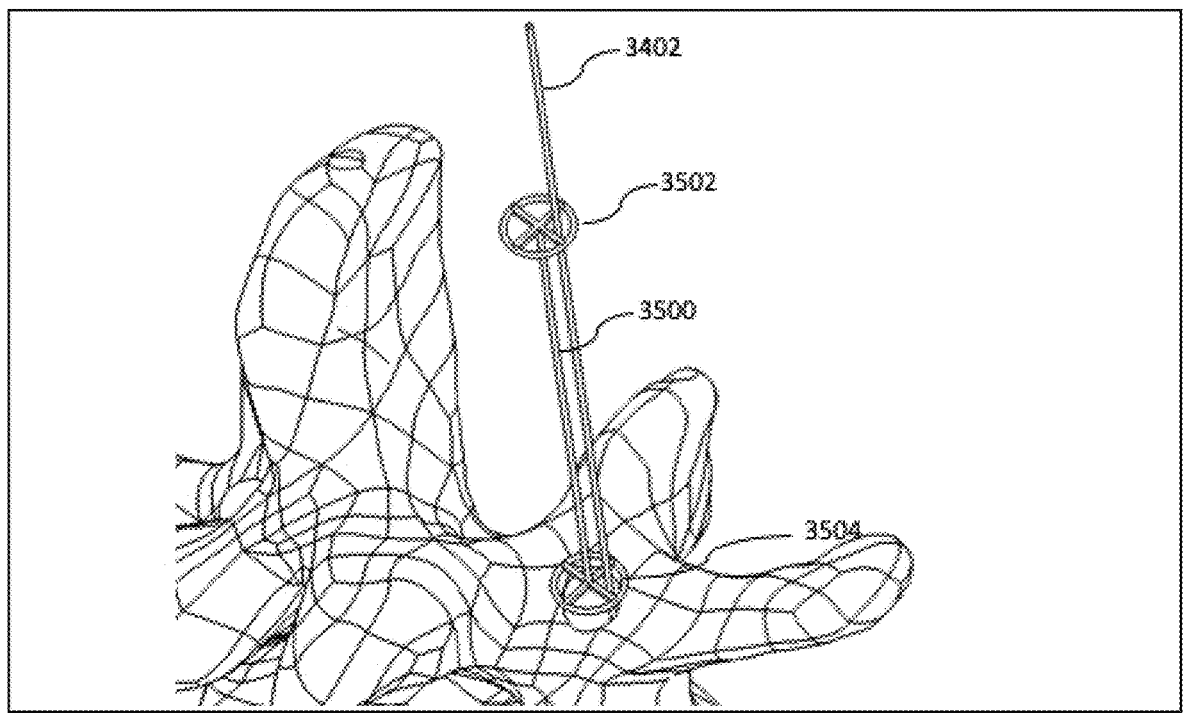
FIG. 35 is a close-up view of the virtual drill and target portion of FIG. 34.
Figures 36A, 36B:
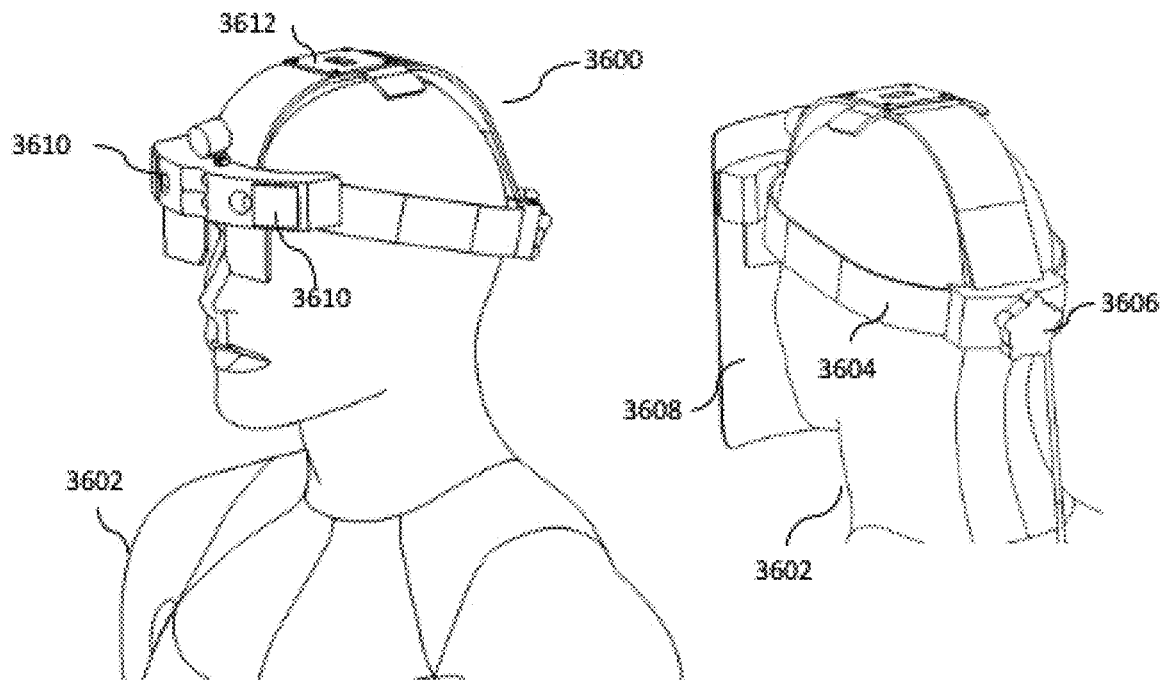
FIG. 36A shows a perspective front view of a diagrammatic depiction of a user wearing an AR headset of the system of FIG. 1.
FIG. 36B shows a perspective back view of a diagrammatic depiction of a user wearing an AR headset of the system of FIG. 1 having a protective face shield.
Figures 37A, 37B:
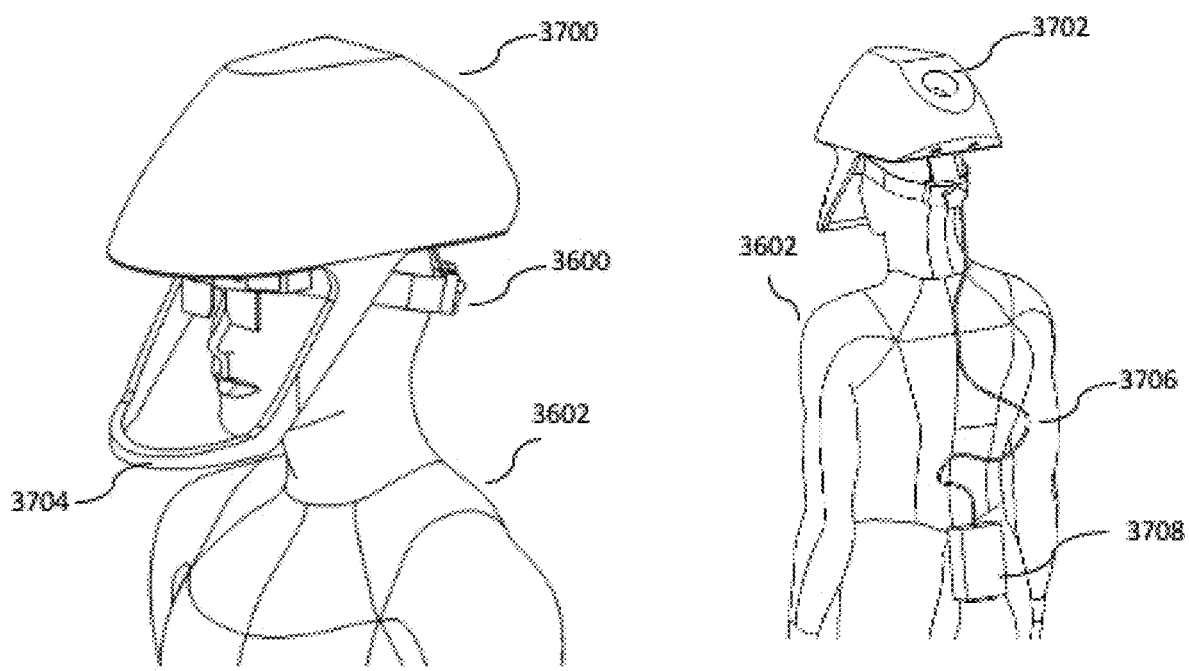
FIG. 37A is a perspective front view of diagrammatic depiction of a user wearing an AR headset of the system of FIG. 1 having a surgical helmet.
FIG. 37B is a perspective back view of the items shown in FIG. 37A.
Figures 38A, 38B:
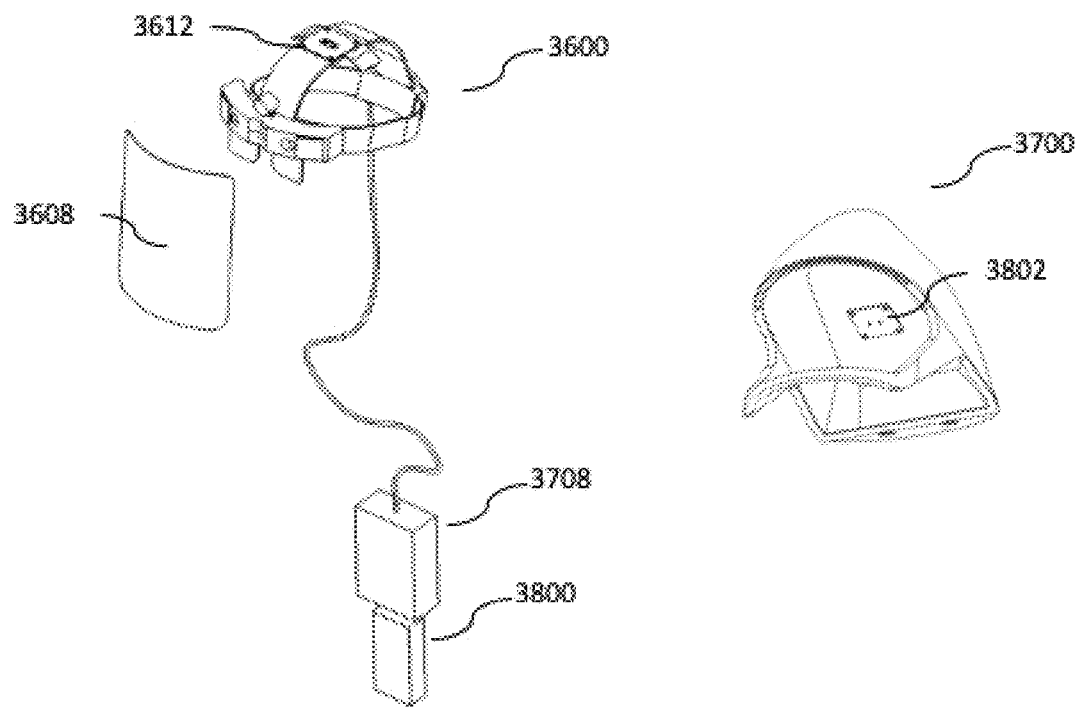
FIG. 38A is a perspective front view of diagrammatic depiction of various components of the system of FIG. 1.
FIG. 38B is a perspective back view of the surgical helmet shown in FIG. 37A.

FIG. 34 depicts an exemplary embodiment of a MXUI shown to the user 106 via the display device 104 during a spinal fusion procedure. A virtual target 3400 for the drill bit and a virtual drill bit 3402 are shown. A virtual vertebra 3404, rendered to be transparent relative to the virtual target 3400 and virtual drill bit 3402 are shown. The numerical angle of the drill bit and the depth of penetration or distance from the tip of the drill bit to the maximum safe depth of insertion are displayed numerically as virtual text 3406. FIG. 35 depicts a close-up view of the virtual target 3400 and virtual drill bit 3402 shown in FIG. 34. The virtual target 3400 is shown in the form of a rod 3500 which has a proximal crosshair 3502 and a distal crosshair 3504. To maintain the actual drill bit in a safe target trajectory, the user must maintain a position in which the virtual drill bit 3402 passes through the rings of both crosshairs of the virtual target 3400. The ideal trajectory is achieved when the virtual drill bit 3402 passes through the center of both crosshairs. If the actual drill bit moves outside a safe target trajectory, the color of the virtual target 3400 changes to alert the user and an audible warning is emitted. The distal crosshair 3504 is positioned at the planned starting point on the surface of the bone. The axial length of the virtual target 3400 and the virtual drill bit 3402 are scaled so that their proximal ends are coincident when the drill reaches its maximum planned depth. The scaling for motions of displacement of the virtual drill bit 3402 is 1:1 when it is far from the virtual target 3400 but expands to a higher magnification for greater precision when closer, allowing greater precision.

Although this is described in the context of drilling with a drill bit, this mixed reality view can be used for multiple steps including tapping of a pedicle or driving in a pedicle screw or use of a trackable awl to find the canal of the pedicle screw. As a quick means to re-calibrate the axial location of the tip of the drill, tap or screw as they are swapped out, the user places the tip into a dimple of a marker. Implants can be introduced less invasively by AR guidance, for example an interbody cage can be positioned during a PLIF, XLIF or TLIF procedure.

In another embodiment, a surgical drill could be equipped to communicate wirelessly with the headset to provide two-way communication. This could facilitate various safety and usability enhancing features including the following, for example: automatically stopping the drill or preventing operation if the drill is not within the safe target trajectory or reaches the maximum safe depth; and/or providing a convenient user interface to specify appropriate torque setting parameters for a torque limiting application. For example, a maximum insertion torque for a pedicle screw of a given size or a seating torque for the set screw of a pedicle screw. Actual values used could be recorded within the patient record for documentation or research purposes for example, the torque curve during drilling, the final seating torque of a pedicle screw or set screw, the implanted position of a pedicle screw, or the specific implants used.

In another embodiment, the AR headset 3600 could be connected wirelessly to a neuromonitoring/nerve localization system, to provide the user 106 (e.g., spine surgeon) real-time warnings and measurements within his field of view, particularly during minimally invasive procedures such as XLIF. Further, when used in conjunction with pre-operative imaging in which the patient's actual nerves have been imaged and reconstructed into 3D models, if the system detects that a particular nerve has been stimulated or is being approached by the stimulating probe, the hologram representing that nerve structure can be highlighted to the user 106 to make it easier to avoid contact with or injury to the nerve structure.

VI. Knee Replacement Procedures

Figure 42:
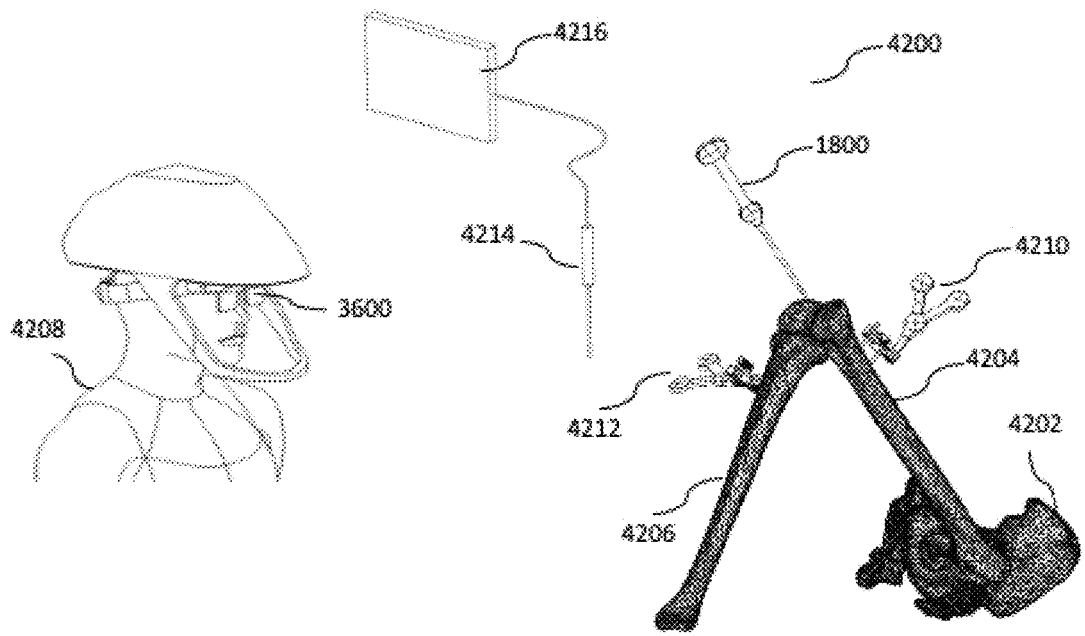
FIG. 42 is a perspective front view of components of the system shown in FIG. 37A used in a knee replacement procedure.

In another exemplary embodiment of the present invention and referring to FIG. 42, the system 10 is used for knee replacement surgery. A pelvis 4202, femur 4204, and tibia 4206 of a knee replacement patient are shown in FIG. 42, the surgeon 4208 (i.e., the user 106) is shown wearing the AR headset 3600. A femur marker 4210 and tibia marker 4212 are fixated to the femur and tibia, respectively, with pins. The femur is moved through a range of motion to determine the center of rotation as a proxy for the center of the hip in the reference frame of the femur marker 4210. The knee is then flexed through a range of motion to determine the baseline, pre-operative flexion axis of the knee. The surgeon 4208 then makes an incision to expose the knee joint. A stylus 1800 is used for registration of the center of the distal femur, based on a landmark, such as the most distal point of the sulcus of the trochlea. The proximal center of the tibia is defined by registration of the footprint of the ACL with the tip of the stylus. For certain minimally invasive procedures, bony landmarks may be registered arthroscopically by insertion of the stylus through one port into the joint capsule and visualizing it with an arthroscope 4214 inserted through a second port. Further, the arthroscopic image 4216 from the arthroscope may be communicated wirelessly to the AR headset 3600 and displayed as part of a MRUI. In an alternative embodiment, a stylus tip could be incorporated in a trackable arthroscope, allowing landmark registrations to be performed through a single port. The stylus 1800 may then be used to register the medial and lateral malleoli and determine the center of the ankle in the reference frame of the tibia marker 4212 by interpolation of these points. At this point a femoral reference frame is established with its origin at the center of the distal femur, with a first axis extending toward the center of the hip, a second axis defined by the flexion axis of the knee and a third axis defined as the normal to the first and second axes. A tibial reference frame is defined with its origin at the center of the proximal tibia, with a first axis extending toward the center of the ankle, a second axis defined by the flexion axis of the knee and a third axis defined as the normal to the first and second axes. These reference frames may be presented as virtual images in a MRUI.

Figure 43:
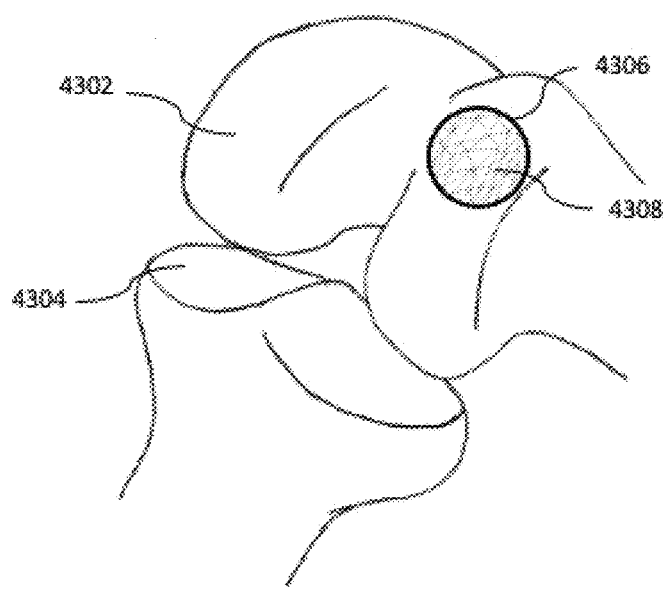
FIG. 43 is a diagrammatic depiction of a MXUI provided by system of FIG. 1 during registration of a distal femur in a knee replacement procedure.

FIG. 43 shows an exemplary embodiment of a MXUI shown to the surgeon 4208 via the AR headset 3600 during a knee replacement surgery with the knee exposed. A topographical map of the femoral condyles 4302 and tibial plateau 4304 can be generated by scanning with the depth sensor 3906 in the AR headset 3600 or by use of the stereoscopic cameras 3904 and SLAM. The knee would be flexed through a range of motion and the surgeon 4208 would adjust his vantage point to allow as much visualization of the condyles as possible. A circle 4306 at the center of the field of view is used by the surgeon 4208 to "paint" the condyles during the registration process and is used as a mask for the mapping algorithm. This circle may be coincident with the projection field of a structured light projector used to enhance the speed and precision of mapping. As surfaces are mapped, a virtual 3D mesh 4308 of mapped areas may be projected onto the articular surfaces to guide the surgeon 4208 and provide a visual confirmation of the quality of the surface registration. An algorithm is then used to determine the lowest point on the articular surfaces of the distal femur and the proximal tibia to determine the depth of the distal femoral and proximal tibial resections. The ideal implant sizes can be determined from the topographical map.

Figure 58A:
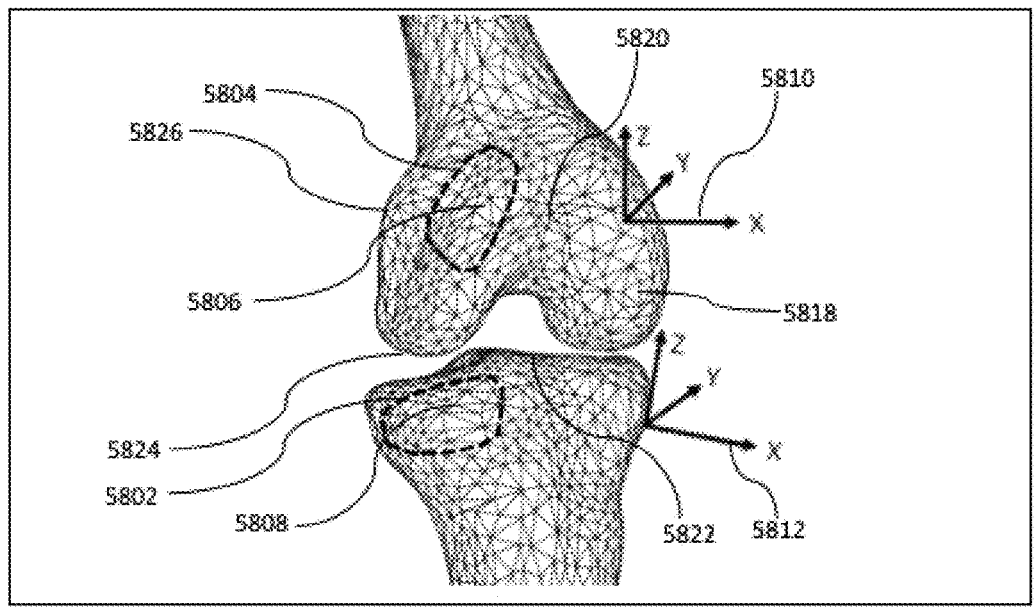
FIG. 58A is a diagrammatic depiction of a knee showing exemplary regions for surface mapping in a reference position.
Figure 58B:
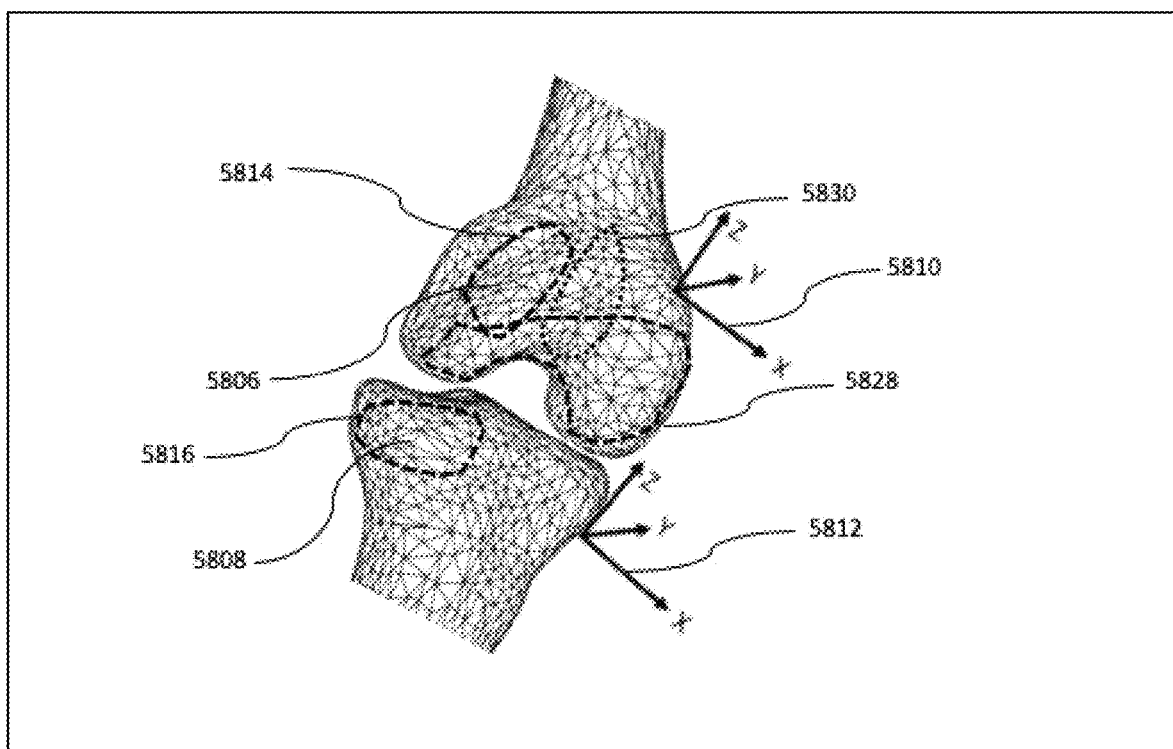
FIG. 58B is a diagrammatic depiction of a knee showing exemplary regions for surface mapping in a displaced position.
Figure 58C:
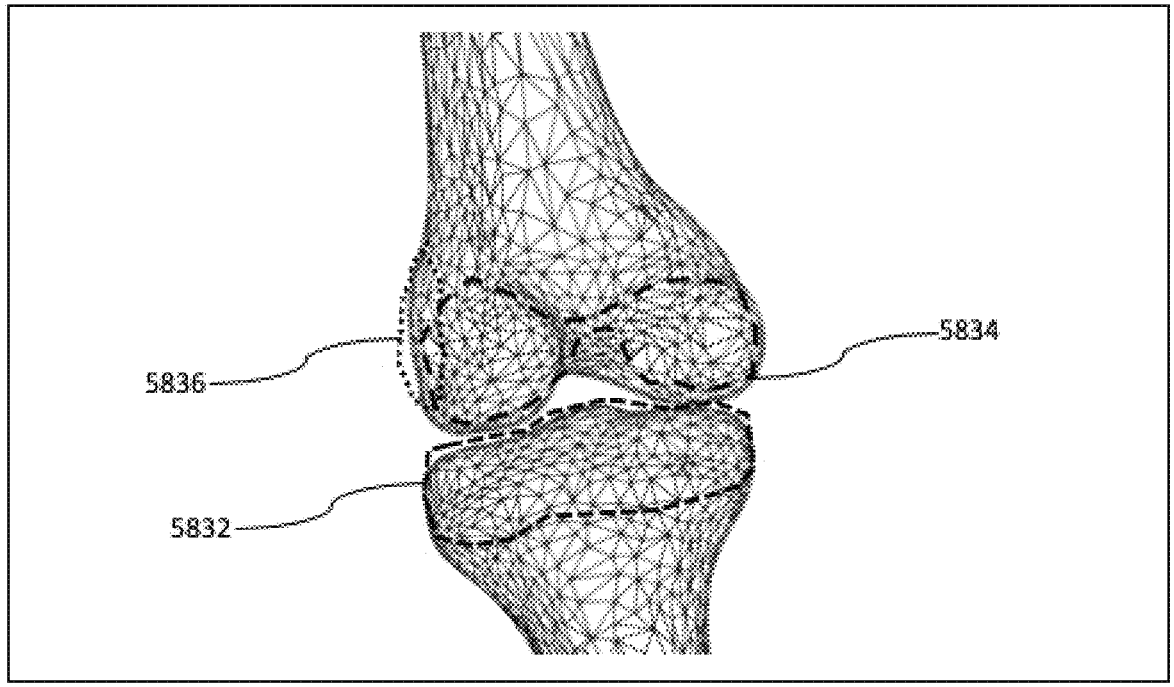
FIG. 58C is a diagrammatic depiction of a knee showing exemplary regions for surface mapping.

In another exemplary embodiment, the system 10 may use the topographical maps of the femur 4204 and tibia 4206 to track the poses of the respective bones (4204, 4206) in lieu of attaching a fiducial marker to the bones (4204, 4206). In one embodiment, the user 106 may select regions of the bones (4204, 4206) that will remain visible as the knee is flexed and extended. Referring to FIGS. 58A-C, the user 106 may select to map the antero-medial aspect of the tibia 5808 or the antero-medial aspect of the distal femur 5806, creating reference 3-dimensional surface maps 5802 and 5804, respectively. These regions are visible through the typical skin incision. Customary retracting instruments and techniques may be used to maintain visibility. The system 10 may store the reference 3-dimensional maps 5802 and 5804 as point clouds, as mathematical surfaces, or by other means. The system 10 may create tibial reference frame 5812 and femoral reference frame 5810 relative to the sensor suite 210 and record the initial pose of the surface maps 5802 and 5804 to reference frames 5812 and 5810, respectively. The user 106 may register additional reference points or structures on the same bone or rigid body, whose pose the system 10 records relative to the reference frame 5812 or reference frame 5810. The system 10, using sensor suite 210, continuously re-scans the same sections of the anatomy and creates displaced 3-dimensional surface maps 5816 and 5814 for the tibia and femur, respectively. Then comparing each displaced surface map 5816, 5814 to the corresponding reference surface map 5802, 5804 created for the same surface, the system 10 determines the geometric rotation and translation required to align the displaced and reference surface maps for best fit. The system 10 then applies the same rotation and translation to all stored reference points and structures on the rigid body of the femur 4204 or tibia 4206, calculating the current pose of all such points and structures relative to the reference frame of sensor suite 210.

Figure 55:
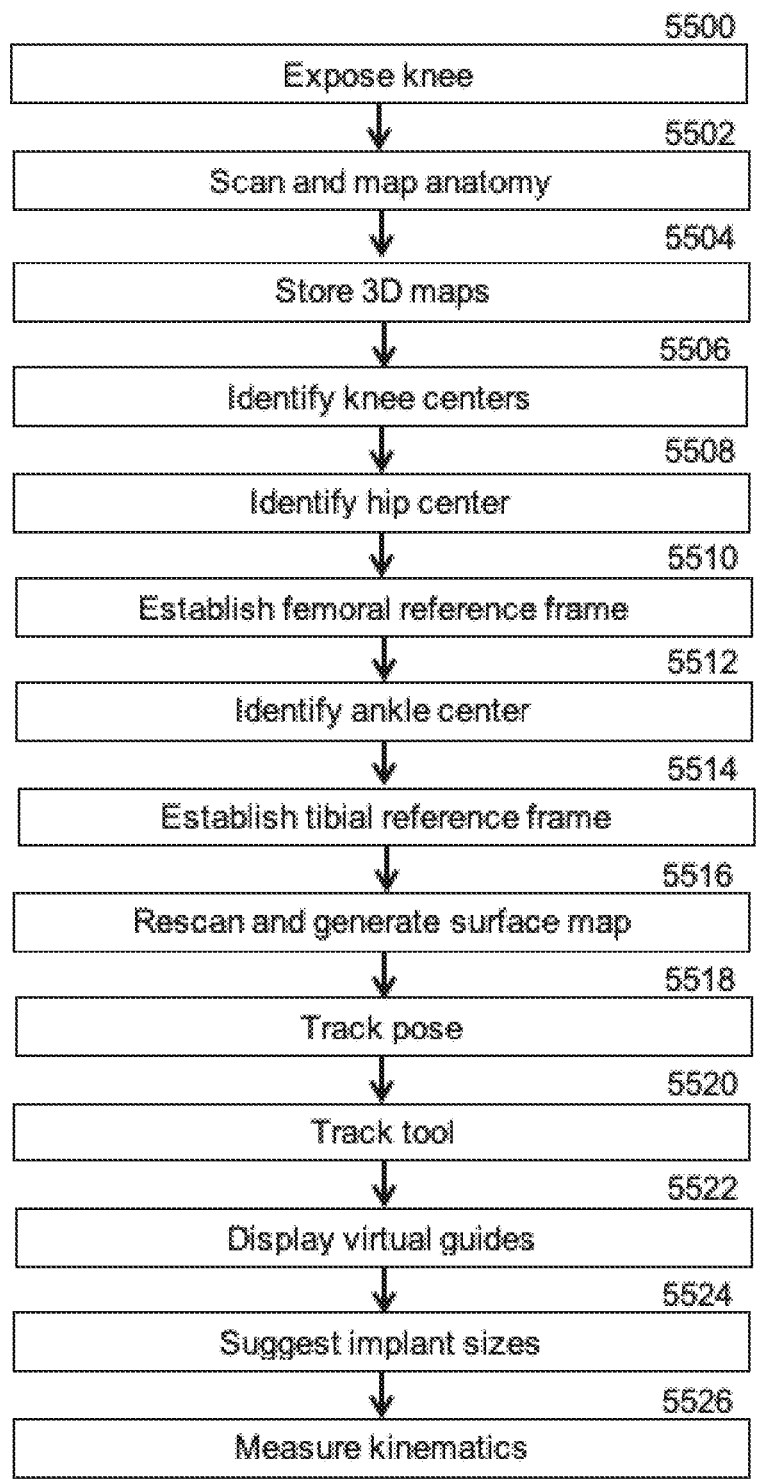
FIG. 55 is a flowchart showing an exemplary method of navigating a knee replacement procedure.

FIG. 55 depicts a flowchart showing an exemplary method for using the system to navigate a knee replacement procedure. The user (106) first exposes the knee to visualize the bony anatomy (5500). The sensor suite 210 then scans the antero-medial aspect of the distal femur 5806 and the antero-medial aspect of the proximal tibia 5808 (5502). From these surfaces, reference 3-dimensional surface maps 5802, 5804 are stored (5504). The system may optionally scan and map larger regions of the femoral condyles 5818, trochlea 5820, tibial plateau 5822, posterior condyles 5824, or epicondyles 5826. From these expanded surface maps 5828, 5830, 5832, 5834, 5836 respectively, and optionally using external anatomic data, the system 10 identifies the center on the distal femur 4204 and the center of the proximal tibia 4206 (5506). The femur is moved through a range of motion whilst scanning the distal femur 5806 to determine the center of rotation of the femur about the hip as a proxy for the center of the hip relative to the mapped distal femoral anatomy 5804 (5508). The user 106 then positions the knee at 90° flexion by arranging the lower leg 5112 approximately perpendicular to the femur 4204. With the knee flexed, the system 10 uses its sensor suite 210 to scan the distal femur 5806 and lower leg 5112, identifying its approximate central axis 5114. Alternatively, the system 10 uses its sensor suite 210 to scan the distal femur 5806 and proximal tibia 5808 as the knee is flexed through a 90-degree range of motion to identify an average flexion axis of the knee. The system 10 then establishes a reference frame 5810 for the femur 4204 relative to the sensor suite 210 with its origin at the center of the distal femur, with a first axis extending toward the center of the hip, a second axis parallel to the axis of the lower limb 5114, and a third axis defined as the normal to the first and second axes (5510). Alternatively, the system establishes a reference frame 5810 for the femur 4204 relative to the sensor suite 210 with its origin at the center of the distal femur, a first axis extending toward the center of the hip, a second axis parallel to the flexion axis of the knee, and a third axis defined as the normal to the first and second axes. The locations of the posterior condyles relative to the tibia are recorded, and an axis is constructed between them. The system 10 generates a surface map of a section of the dorsal surface of the foot for the purpose of tracking its pose. In alternative embodiments, the foot may be tracked via a marker affixed to the skin or overlying drapes, wrappings, or boot. The foot is moved through a range of motion to determine its center of rotation as a proxy for the center of the ankle relative to the mapped proximal tibial anatomy (5512). The mechanical axis of the tibia is then constructed between the proximal tibia and ankle centers and establishes a reference frame 5812 for the tibia 4206 relative to the sensor suite 210 with its origin at the center of the proximal tibia, with a first axis extending toward the center of the hip, a second axis parallel to the axis of the lower limb 5114, and a third axis defined as the normal to the first and second axes (5514). Alternatively, the system establishes a reference frame 5812 for the tibia 4206 relative to the sensor suite 210 with its origin at the center of the proximal tibia, a first axis extending toward the center of the ankle, a second axis parallel to the flexion axis of the knee and a third axis defined as the normal to the first and second axes. Then, repeatedly scanning the exposed distal femur 5806 and proximal tibia 5808, the system 10 generates displaced surface maps 5814 and 5816 for each scan (5516). With each successive scan, the system can compare the displaced surface maps 5814 and 5816 to the original surface maps 5804 and 5802 for the corresponding region on the distal femur 5806 and proximal tibia 5808, respectively. Based on this comparison, the system 10 can track the pose of the femur 4204 and tibia 4206 relative to sensor suite 210 by determining the translation and rotation required to align the displaced surface maps 5814 and 5816 with the reference surface maps 5804 and 5802 (5518). The system 10 then calculates and displays the angles and depths of resection on the distal femur and proximal tibia by simultaneously tracking the respective mapped anatomic surface and a cutting tool or guide (5520). The system 10 may then display virtual guides to assist the user 106 in aligning the cutting tool or guide with a user-defined target angle or depth (5522). The system 10 may suggest implant sizes to the user 106 based on external implant data (5524). Following placement of implants or trial implants, the system 10 may track the femur and tibia throughout a range of flexion and measure the relative rotation of the femur and tibia about one or more axes, representing, for example, axial rotation or varus/valgus rotation (5526).

Optionally, the system 10 may use the mapped topography to automatically determine the respective centers of the distal femur 5804 (e.g., by identifying the most distal point on the trochlea or the center of a line through the widest part of the condyles) or proximal tibia 5802 (e.g., by calculating the centroid of the plateau). Optionally, the identification of the center point may be supplemented by external data such as a library of anatomic topographical maps in which the center had been identified, allowing the system 10 to calculate the center point in cases in which the anatomy was partly obscured, preventing mapping of the entire surface.

Figure 56:
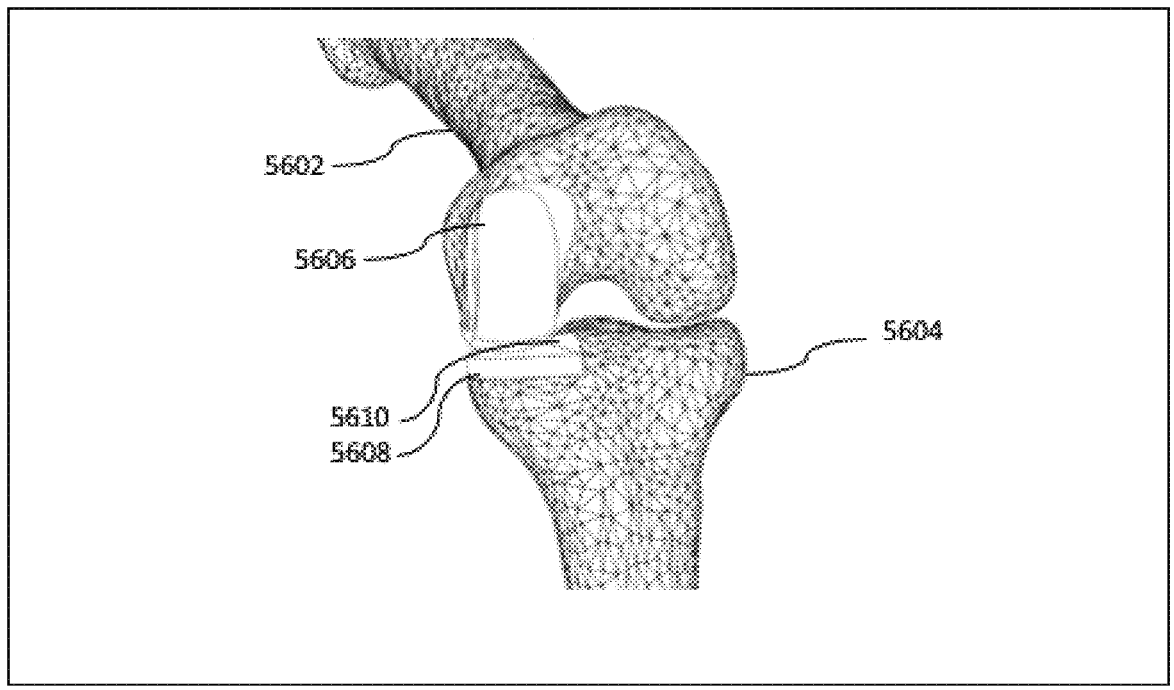
FIG. 56 is a diagrammatic depiction of a knee with unicondylar implants.

FIG. 56 depicts a knee with implanted unicondylar components. One compartment of each of the femur 5602 and tibia 5604 has been resected. A femoral implant 5606 and a tibial implant 5608 have been implanted. In one exemplary embodiment, the system 10 tracks and records the relative motion of the native femur 5602 and tibia 5604. Then, scanning and mapping the surfaces of the implants (5606, 5608) using cameras 206, the system 10 may calculate the paths of the implant surfaces following the recorded tibio-femoral motions. The system 10 may also map the remaining exposed bone 5610 and detect impingement between implants (5606, 5608) and bone 5610. The volume representing the overlap between interfering bodies may be calculated and overlaid as a virtual model in the display device 104. The system 10 may also highlight impingement sites in the display device 104. For example, the femoral implant 5606 may impinge on the ridge of tibial bone adjacent to the sagittal resection plane 5610, or this ridge may impinge on the femoral bone adjacent to the femoral implant 5606. If at least one contacting surface is a bone, the user 106 may elect to trim the bone to change the contact point. If at least one contacting surface is on an implant, the user 106 may elect to adjust the position of the implant to reduce impingement.

Figure 57:
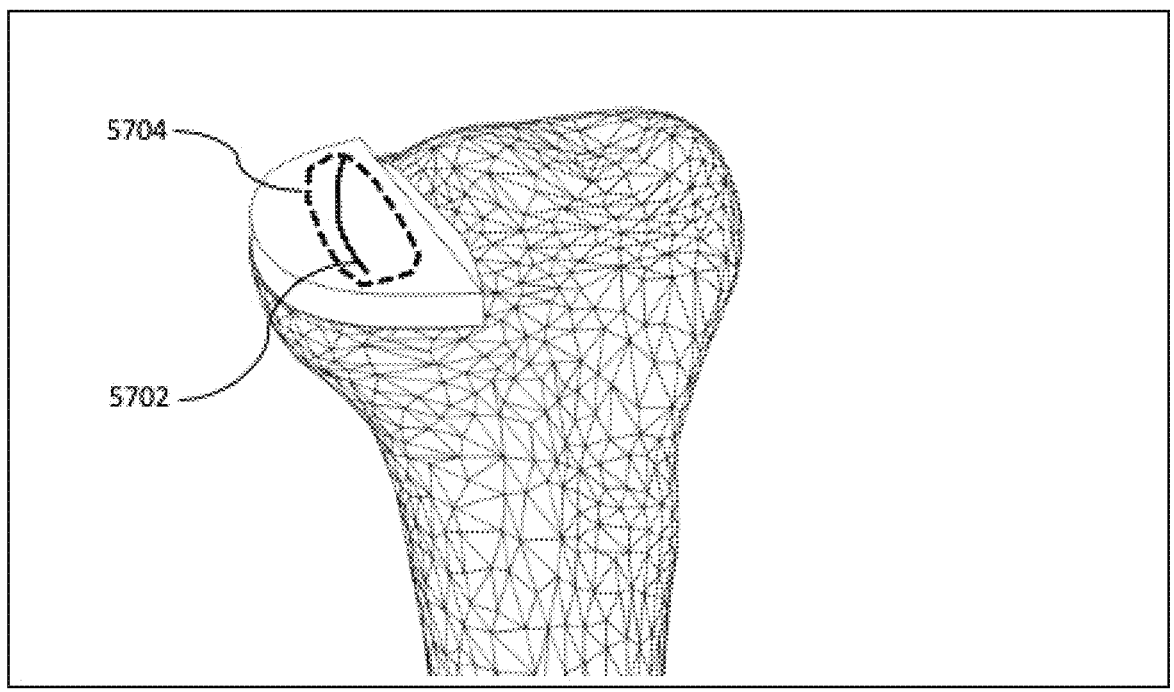
FIG. 57 is a diagrammatic depiction of a tibia with unicondylar implant.

Referring to FIG. 57, the system 10, having recorded the native tibio-femoral kinematics, may display to the user 106 the locus of the inter-implant contact point 5702 and a pre-defined safe zone 5704, projected onto the surface of the implant.

Figure 44:
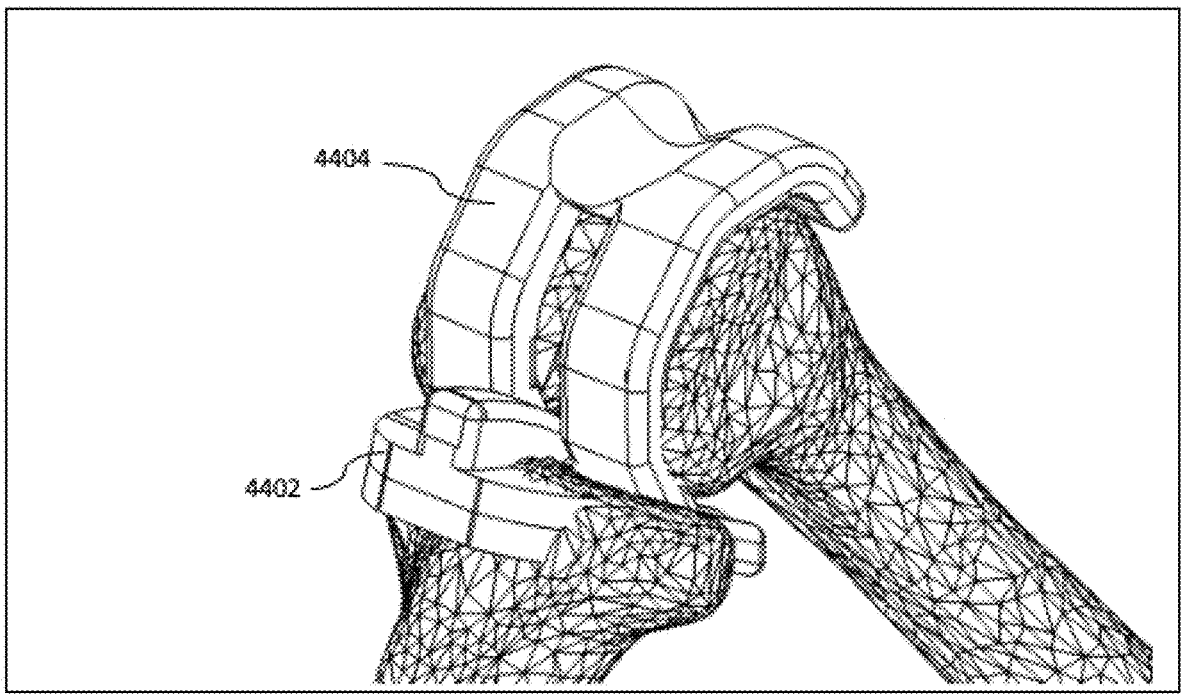
FIG. 44 is a diagrammatic depiction of a MXUI provided by system of FIG. 1 during resection plane planning in a knee replacement procedure.

Referring to FIG. 44, a virtual tibial implant 4402 and virtual femoral implant 4404 can be displayed in a MXUI shown to the surgeon 4208 via the AR headset 3600. The surgeon 4208 may switch the sizes and adjust the position of these virtual models until satisfied. In another embodiment, the virtual tibial implant may be displayed during preparation of the tibia for broaching to provide a guide for the rotational alignment of the tibial component.

Figure 45:
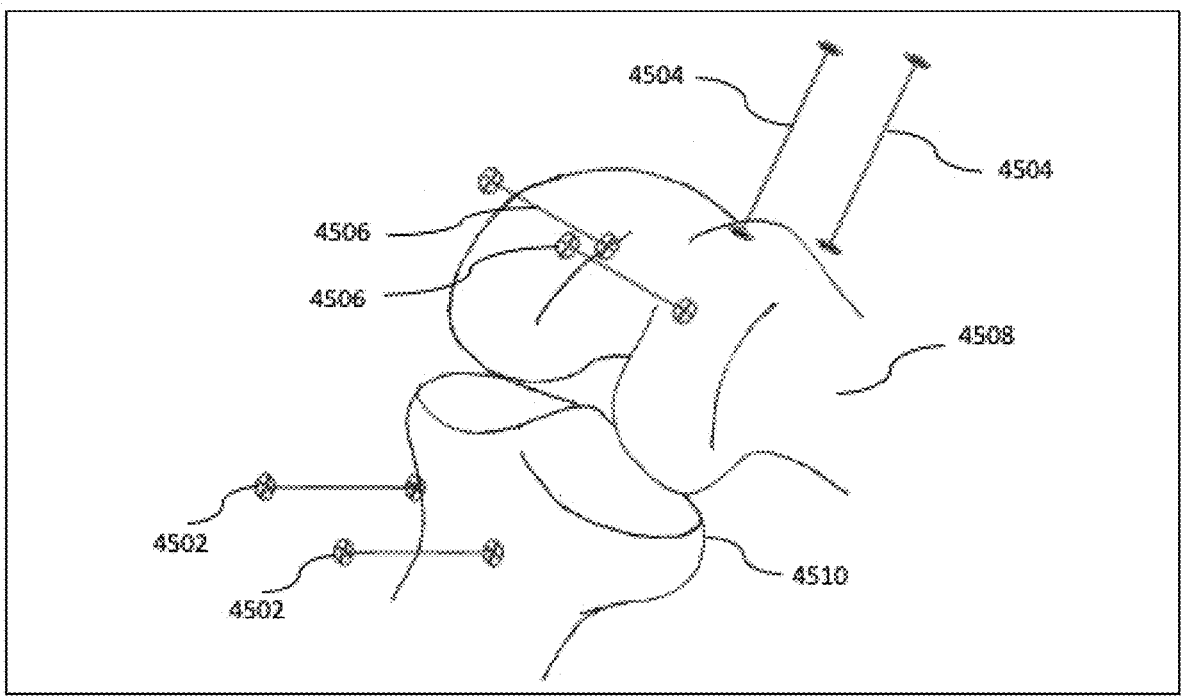
FIG. 45 is a diagrammatic depiction of a MXUI provided by system of FIG. 1 during placement of pins for location of cutting blocks in a knee replacement procedure.

Referring to FIG. 45, virtual guides 4502 for location of pins for the tibial cutting block are displayed in a MXUI shown to the surgeon 4208 via the AR headset 3600. Virtual guides 4504 for location of pins for the distal femoral cutting block are displayed. Virtual guides 4506 for location of pins for the 4 in 1 cutting block are displayed. Placement of the actual pins is guided by aligning them with the virtual guides 4502, 4504 or 4506. The femur 4508 and tibia 4510 may then be resected by placing cutting blocks on these pins.

Figure 46:
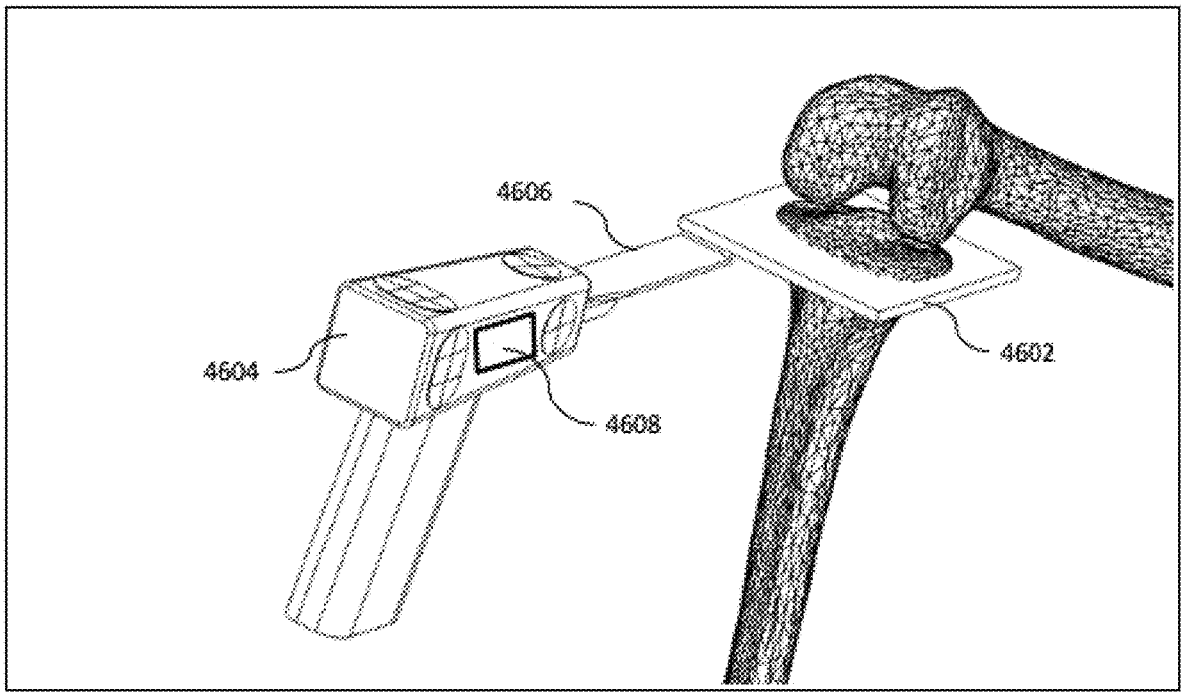
FIG. 46 is a diagrammatic depiction of a MXUI provided by system of FIG. 1 during tibial resection in a knee replacement procedure.

FIG. 46 depicts an alternative embodiment of the MXUI shown in FIG. 45 wherein a virtual guide 4602 is used to display the ideal plane of resection and the surgeon 4208 may resect the bone directly by alignment of the actual saw blade with the virtual guide 4602. Alternatively, in the case of a tracked saw 4604, the surgeon 4208 may resect the bone by alignment of a virtual saw blade 4606 with the virtual guide 4602. Virtual text 4608 showing the varus/valgus angle, flexion angle and depth of each resection may be displayed numerically when relevant.

Figure 47:
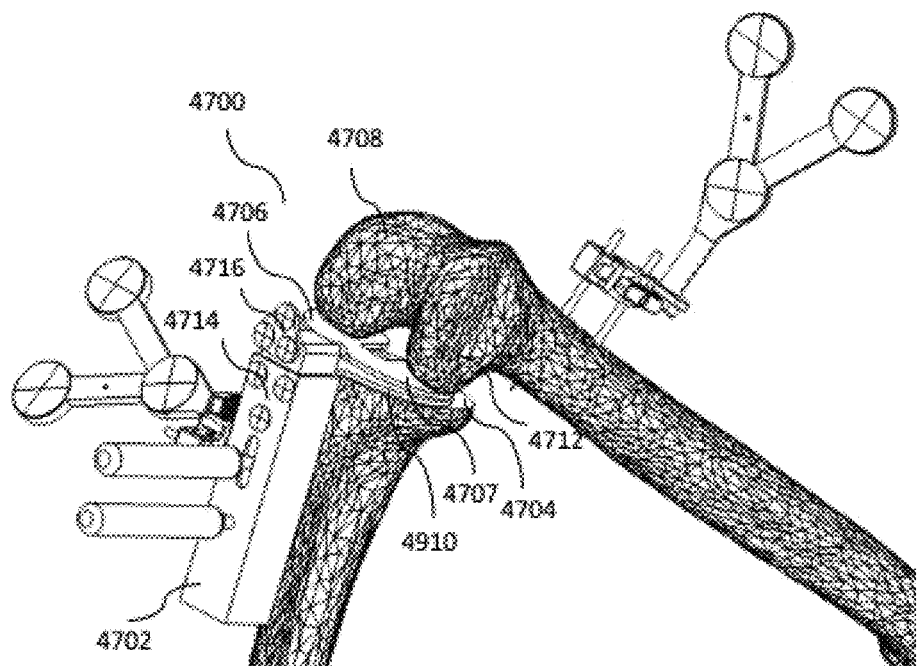
FIG. 47 is a perspective front view of a diagrammatic depiction of a knee balancing device that is optionally included in the system of FIG. 1 in use during a knee replacement procedure.
Figure 49:
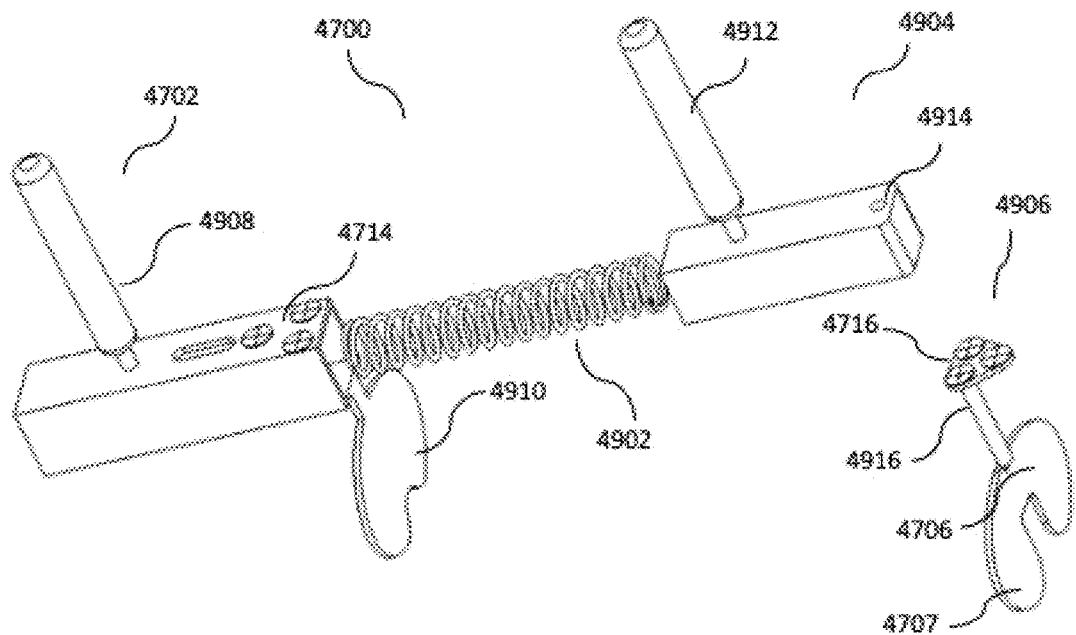
FIG. 49 is a perspective front view of the knee balancing device shown in FIG. 47.

FIGS. 47 and 49 depict a knee balancing device 4700 that may be optionally included in the system 10 having a base element 4702, a spring 4902, a condylar element 4904, and a condylar plate 4906. The base element 4702 includes a handle 4908, a target 4714 and a tibial plate 4910. The condylar element 4904 includes a handle 4912 and a cylindrical bearing hole 4914. The condylar plate 4906 includes a cylindrical bearing shaft 4916, a target 4716, and two paddles 4706 and 4707. The condylar plate 4906 pivots about a cylindrical bearing 4916, which allows medial/lateral tilt of the condylar plate 4906 relative to the base plate 4910. In an alternative embodiment, the bearing 4916 may be a ball-type allowing medial/lateral and flexion/extension tilt of the condylar plate 4906. In another embodiment, the condylar plate 4906 may be contoured to match the topography of the bearing surface of a tibial implant. In another embodiment, the design could include two fully independent condylar elements each with a rigidly integrated distraction paddle and a marker.

Referring to FIG. 47, the tibial plate 4910 is seated on the resected tibia 4704, and the distraction paddles 4706 and 4707 maintain contact with the medial femoral condyle 4708 and the lateral femoral condyle 4712, respectively. The distraction paddles 4706 and 4707 are pushed by the spring 4902 and pivot about an anteroposterior axis to provide a nearly equal and constant distraction force between each femoral condyle (4708, 4712) and the tibia 4704. The base element 4702 and distraction paddles (4706, 4704) include optical markers (4714, 4716) which allow the software to measure the degree of distraction of each femoral condyle (4708, 4712).

Figure 48:
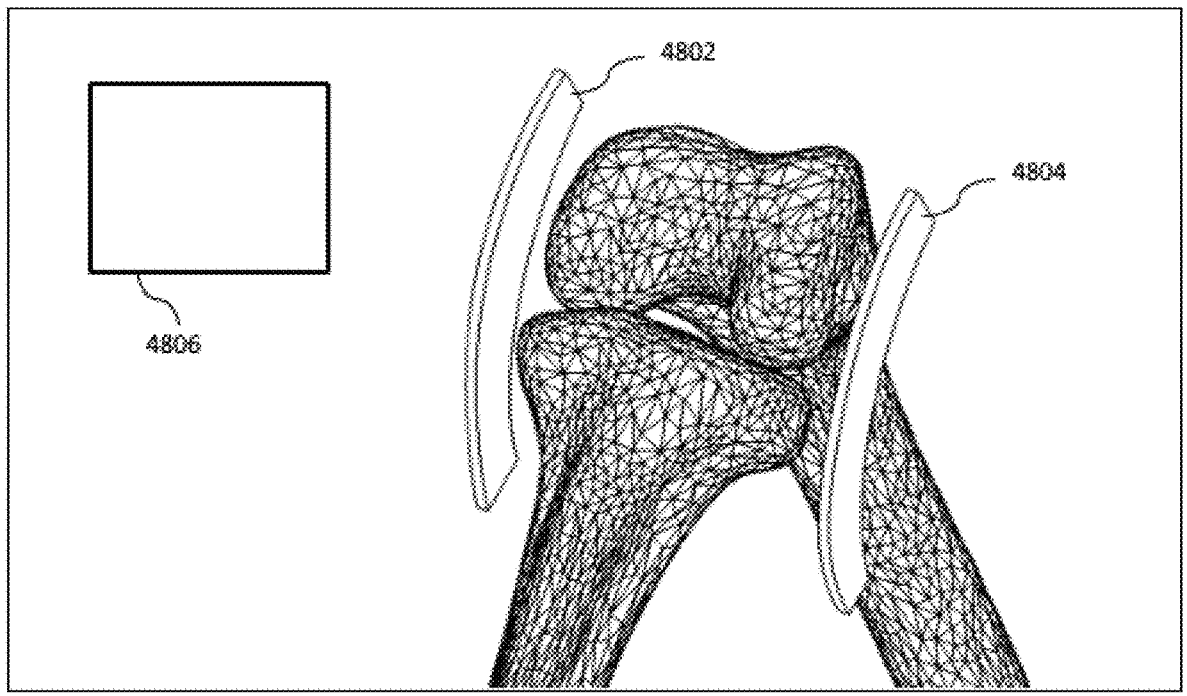
FIG. 48 is a diagrammatic depiction of a MXUI provided by system of FIG. 1 during a balancing assessment in a knee replacement procedure.

As the knee is flexed through a range of motion, the position of each target is tracked, as is the pose of the tibia and femur. This data is used to generate a plot of medial and lateral laxity as a function of flexion angle. This information is used to calculate the ideal location of the distal femoral cutting block location pins to achieve balance through the range of motion of the knee or to guide the user in removing osteophytes or performing soft tissue releases to balance the knee through its range of motion. This plot may be displayed in a MXUI as shown in FIG. 48 in which a first three-dimensional arc 4802 represents the medial laxity and a second three-dimensional arc 4804 represents the lateral laxity through the range of motion of the knee. The numerical values at the current flexion angle of the actual knee can be displayed as virtual text 4806.

Figure 66A:
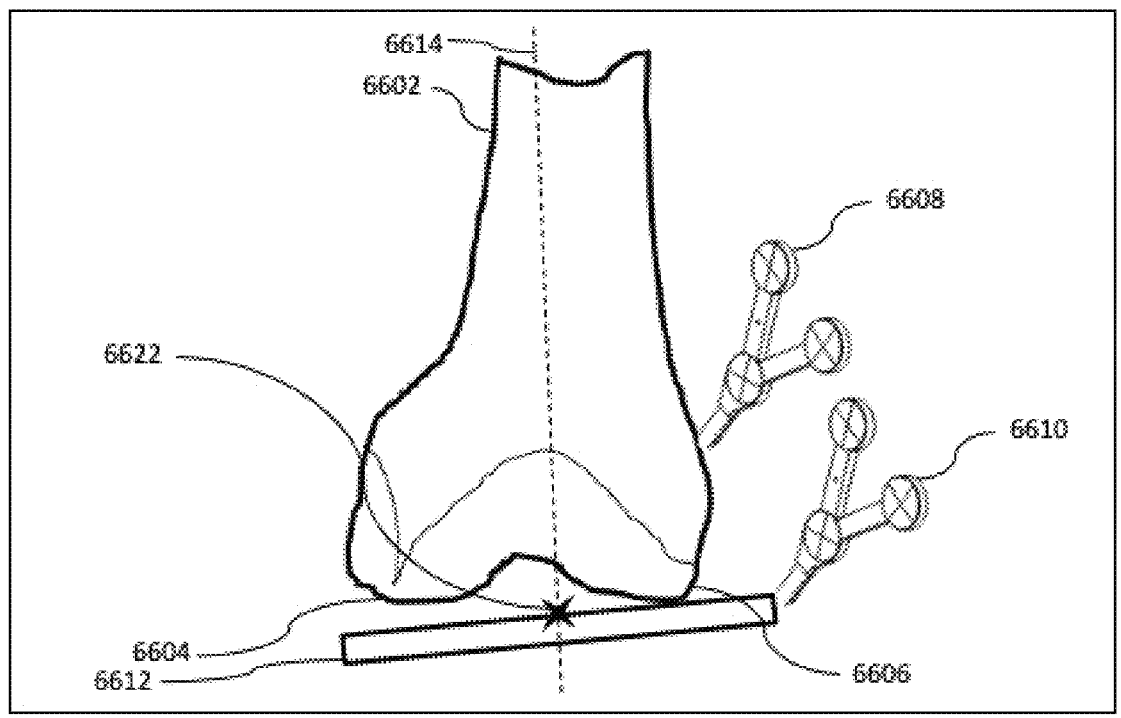
FIGS. 66A-66B show components of a system to measure resection depth in knee surgery.
Figure 66B:
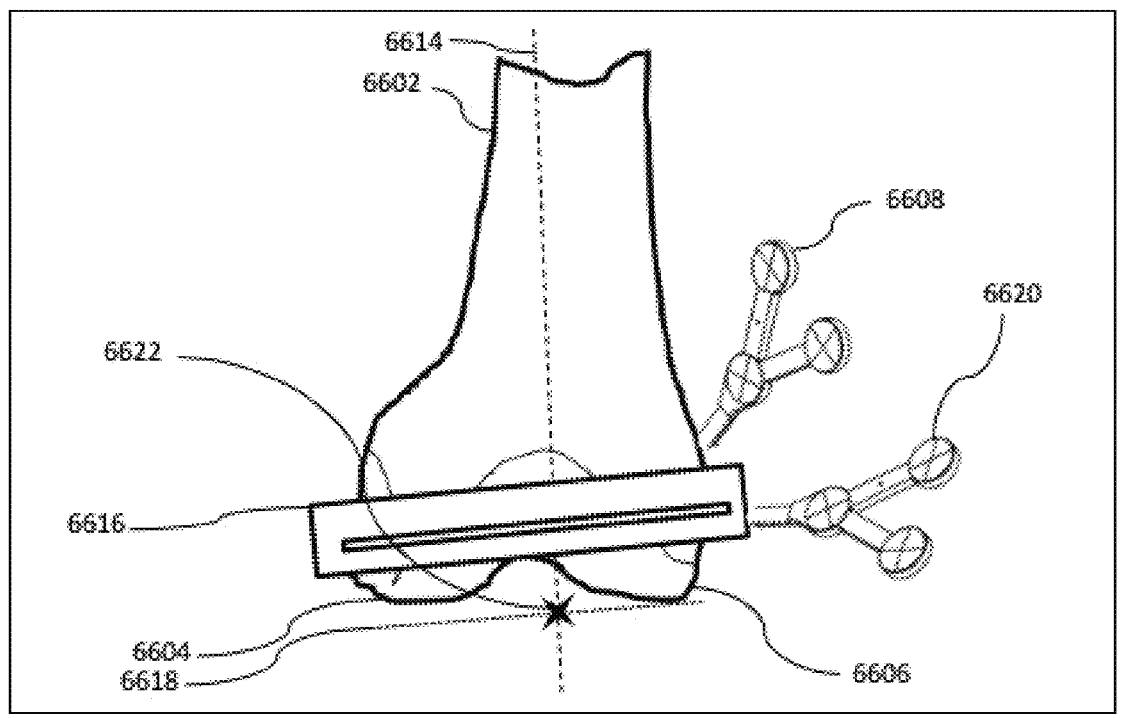

FIGS. 66A and 66B depict one embodiment of the system 10 used for measuring resection depth in knee surgery. Distal femur 6602 comprises condyles 6604 and 6606, and mechanical axis 6614. Markers 6608 and 6610 are rigidly fixed to femur 6602 and condylar guide 6612, respectively. Marker 6620 is rigidly fixed to cutting guide 6616.

Figure 67:
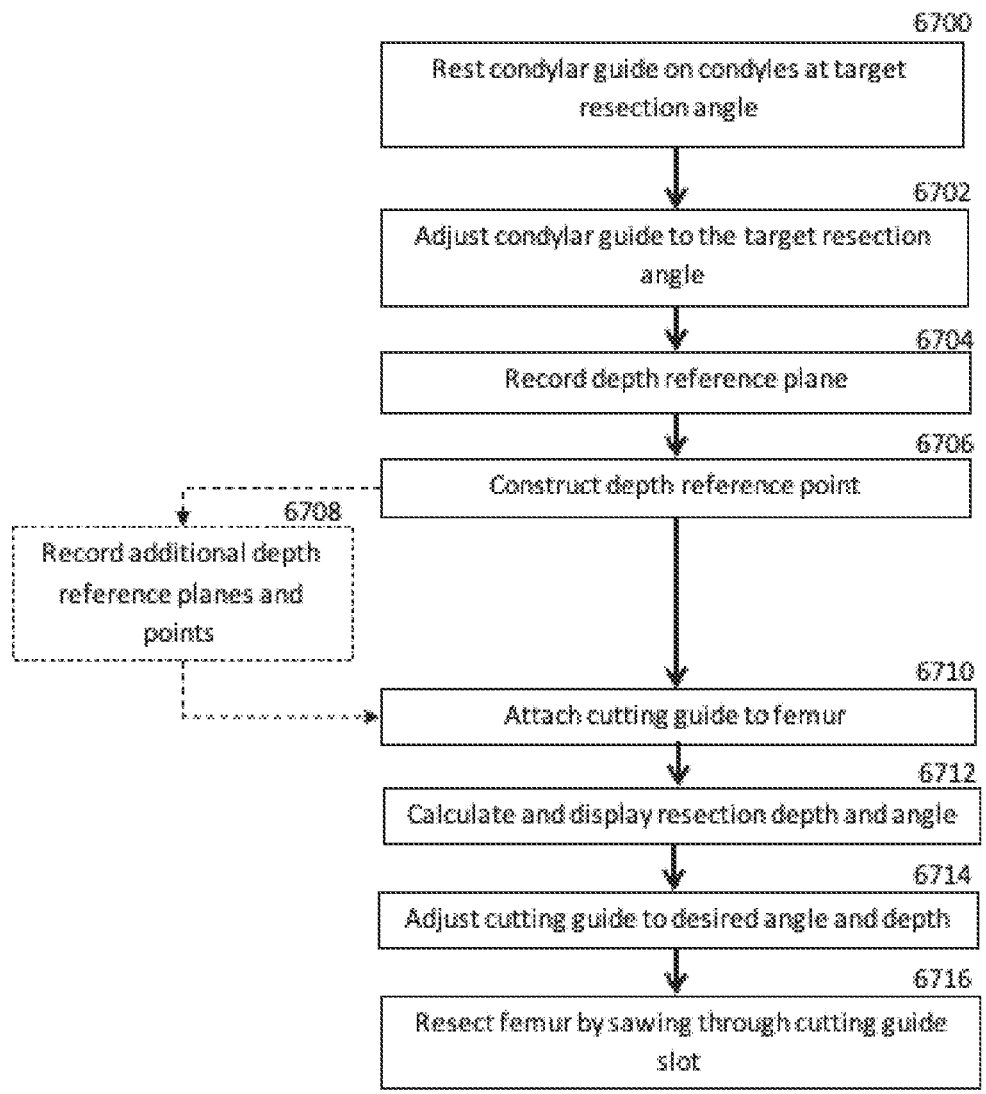
FIG. 67 is a flowchart showing an exemplary method of measuring resection depth on a femur.

A challenge in measuring resection depth is that the femoral condyles, which are used as a depth reference, are shaped irregularly such that their most prominent point changes depending on the angle of the resection plane. A common solution is to map the condylar surface by registering many points on the surface, which is time-consuming but allows a computer to calculate the depth at a particular angle by calculating the distance to the most prominent point along a perpendicular path. FIG. 67 depicts a flowchart illustrating a method of using a system 10 to register the anatomy of the distal femur and measure depth in a knee surgery without mapping the condylar surface. User 106 rests condylar guide 6612 on the condyles 6604, 6606 (block 6700). Following the guidance of the system 10, user 106 adjusts the angle of condylar guide 6612 to the target resection angle while maintaining contact between condylar guide 6612 and at least one of condyles 6604, 6606 (block 6702). The system 10, using sensor suite 210 to track markers 6608 and 6610, measures the pose of condylar guide 6612 relative to femur 6602 and records a depth reference plane 6618 coincident with the surface of condylar guide 6612 in contact with one or more of condyles 6604 and 6606 (block 6704). The system 10 then constructs and records a depth reference point 6622 at the intersection of mechanical axis 6614 and depth reference plane 6618 (block 6706). Optionally, the system 10 may direct user 106 to adjust the condylar guide 6612 to multiple orientations, still maintaining the condylar guide 6612 in contact with at least one of condyles 6604 or 6606, to record additional depth reference planes 6618 and depth reference points 6622 (block 6708). The user 106 then removes condylar guide 6612 from the femur and attaches cutting guide 6616, which is configured to allow user 106 to adjust its angle and depth on femur 6602 (block 6710). As cutting guide 6616 is adjusted, the system 10 measures the position of the cutting guide 6616 relative to femur 6602 by tracking markers 6620 and 6608, respectively. The instantaneous resection depth is calculated as the normal distance from the current resection plane defined by cutting guide 6616 to the depth reference point 6622 corresponding to the depth reference plane 6618 most nearly parallel to the angle of cutting guide 6616 (block 6712). User 106 adjusts cutting guide 6616 to the desired resection angle and depth, following feedback from system 10 (block 6714). Depth measurement accuracy decreases as the angle from the depth reference plane increases, due to the irregular shape of the condyles and uncertainty in identifying the most prominent point on the condylar surface. To minimize the depth error due to misalignment, the system 10 does not display depth measurements if cutting guide 6616 is more than a specified angular limit (e.g., 1 degree) away from the most nearly parallel depth reference plane 6618. Once the cutting guide 6616 is at the desired angle and depth, the user 106 resects the femur by sawing through a slot or against a face of cutting guide 6616 (block 6716). The angular limit may be selected based on a desired resolution. For example, a one degree angular limit may result in about or substantially 1 mm of error.

Figure 68A:
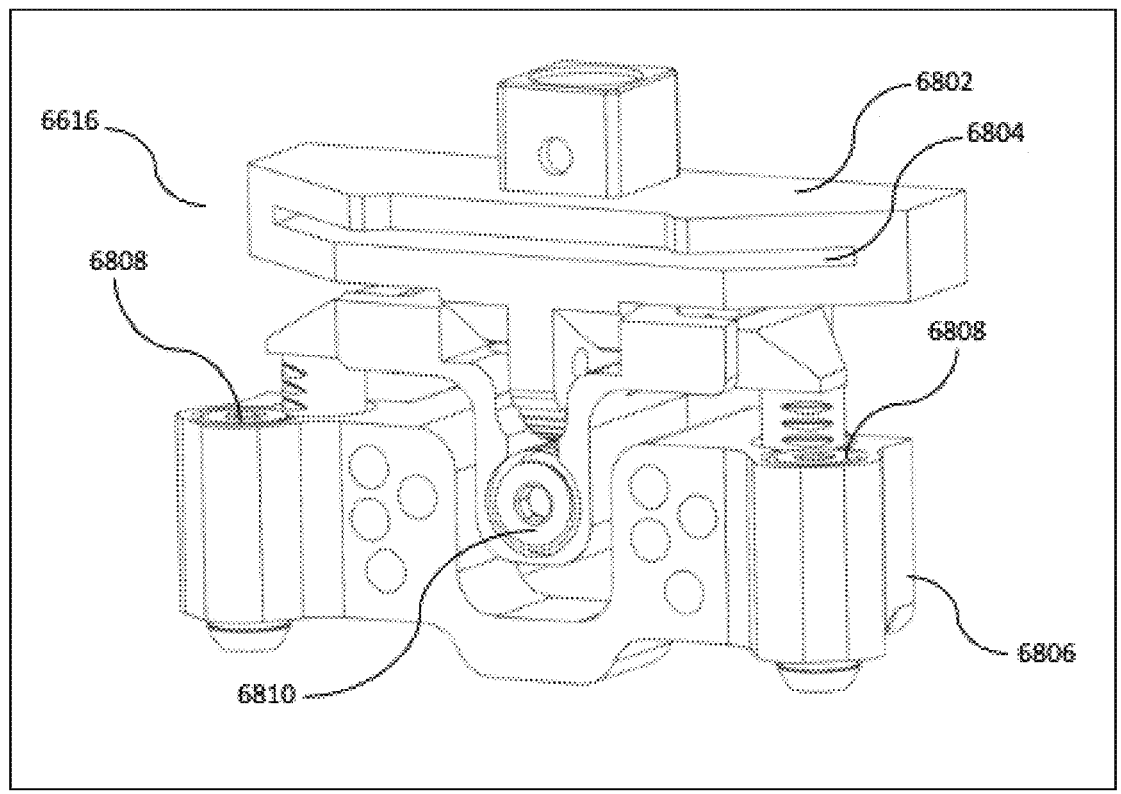
FIG. 68A shows a diagrammatic depiction of an adjustable cutting block.
Figure 68B:
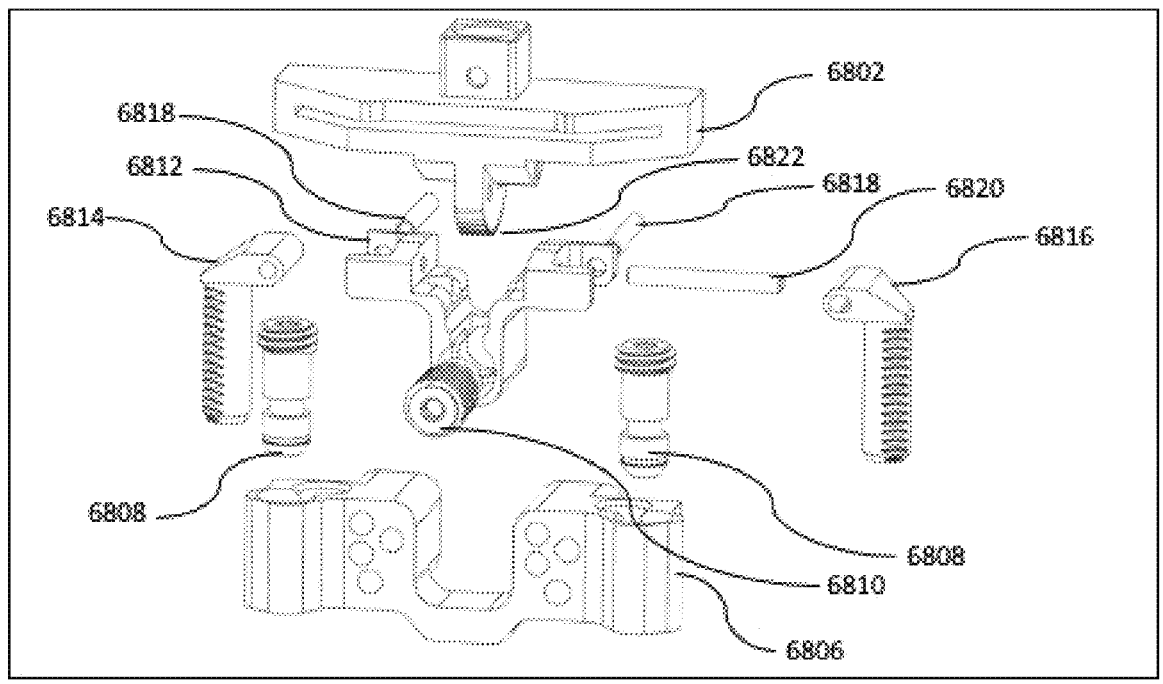
FIG. 68B shows an exploded view of the cutting block depicted in FIG. 68A.

FIGS. 68A and 68B depict one embodiment of cutting guide 6616 configured to be adjustable after mounting on a bone. Fixed base 6806 is rigidly attached to a bone. Movable cutting head 6802 includes a cutting slot 6804. Two valgus adjustment screws 6808 can be turned to adjust the angle of cutting head 6802 in a frontal plane, while flexion adjustment screw 6810 can be turned to adjust the angle of cutting head 6802 in a perpendicular plane. Valgus adjustment screws 6808 actuate left and right adjustment posts 6814 and 6816, respectively, by inter-meshing screw threads. Axial motion of either of these adjustment posts 6814 or 6816 in turn rotates valgus block 6812 and cutting head 6802 about one of valgus pins 6818. In one embodiment, valgus pins 6818 are spaced approximately the same distance as femoral condyles 6604 and 6606, allowing cutting head 6802 to rotate about an axis aligned with one condyle so the distance from cutting slot 6804 to that condyle remains constant as the user 106 adjusts the angle of cutting head 6802. This addresses a common problem with existing cutting guides, where adjusting the angle of the guide in the frontal plane also changes the depth of resection measured from one or both condyles. Further referring to FIG. 68B, cutting head 6802 is configured to pivot in a sagittal plane relative to valgus block 6812 about flexion pin 6820 when flexion adjustment screw 6810 is turned, actuating cutting head 6802 via inter-meshing screw threads 6822 incorporated therein.

VII. Other Medical Procedures

Figure 10:
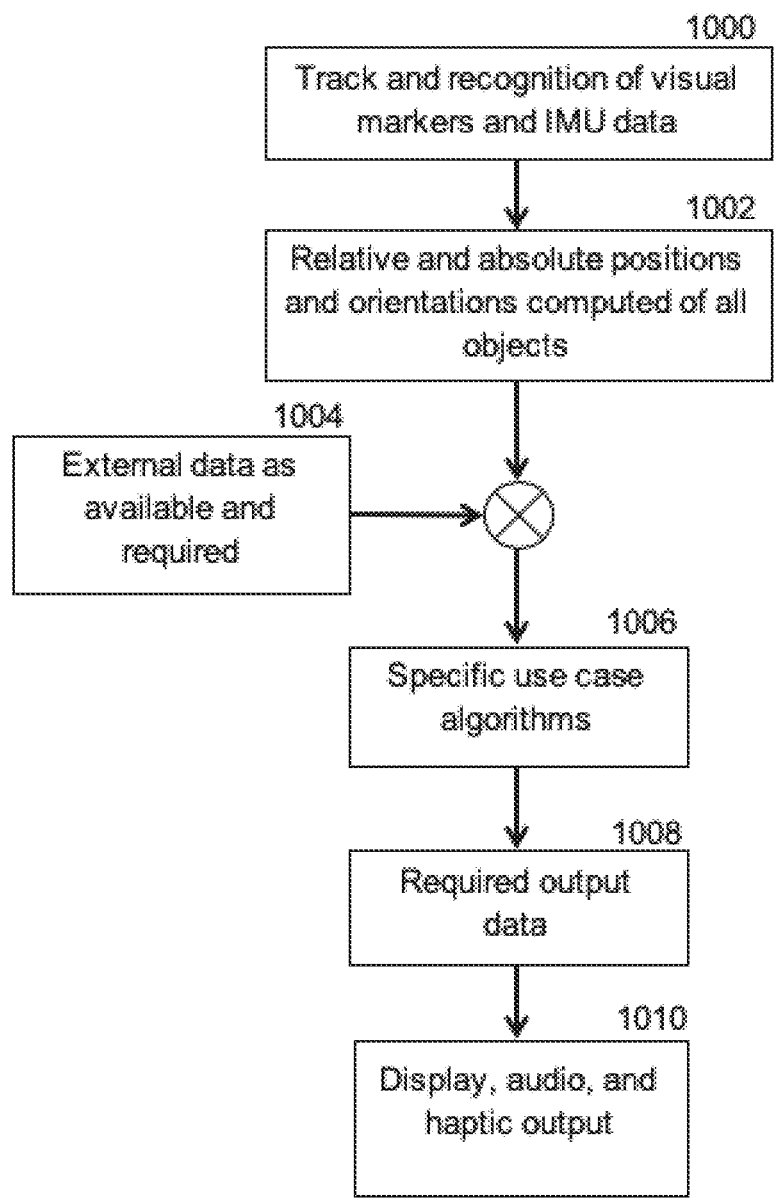
FIG. 10 is a flowchart showing a method of using the system of FIG. 1 to perform a general medical procedure in accordance with the principles of the present invention.

Referring to FIG. 10, the present invention further provides a method of using the system 10 to perform other surgical procedures (specific examples are provided below). The method includes data collection (1000) that includes, but is not limited to, tracking and recognition of visual markers and IMUs. This data is used to determine relative and/or absolute orientation and position of multiple items in the work view (1002). External data (1004) is brought into the algorithm. Algorithms are used to process the data for specific use cases (1006) and determine the required output (1008). This data is used in an augmented reality AR or virtual reality VR output display (1010) to assist the medical professional.

For example, the method can be used for total hip arthroplasty. The markers (e.g., 100, 108, 110, etc.) for anatomic landmarks and tools are used for data collection (1000) and the determination of position and orientation (1002) of hip and surgical tools. Algorithms (1006) are used to determine solutions including, but not limited to, component positioning, femoral head cut, acetabulum positioning, screw placement, leg length determination, and locating good bone in the acetabulum for revision setting.

The method can also be used for total knee arthroplasty. The markers (e.g., 100, 108, 110, etc.) for anatomic landmarks and tools are used for data collection (1000) and the determination of position and orientation (1002) of knee, tibia, and surgical tools. Algorithms (1006) are used to determine solutions including, but not limited to, location, angle, and slope of tibial cut; placement and fine-tuning of guide; avoidance of intra-medullary guide; and/or improvement of femoral cuts.

The method can be used for corrective osteotomy for malunion of distal radial fractures. The markers (e.g., 100, 108, 110, etc.) for anatomic landmarks and tools are used for data collection (1000), which may be combined with pre-operative CT scan data for the determination of position and orientation (1002) of malunion and surgical tools. Algorithms (1006) are used to determine solutions including but not limited to location of osteotomy, angle of cut and assessment of results.

The method can be used for corrective osteotomy for malunion of arm bones including the humerus, distal humerus, radius, and ulna with fractures that can be complicated and involve angular and rotational corrections. The markers (e.g., 100, 108, 110, etc.) for anatomic landmarks and tools are used for data collection (1000), which may be combined with pre-operative CT scan data for the determination of position and orientation (1002) of malunion and surgical tools. Algorithms (1006) are used to determine solutions including, but not limited to, location of osteotomy site, angle of cut, degree of correction, and assessment of results.

The method can be used for distal femoral and proximal tibial osteotomy to correct early osteoarthritis and malalignment. The markers (e.g., 100, 108, 110, etc.) for anatomic landmarks and tools are used for data collection (1000), which may be combined with pre-operative CT scan data or long-leg X-ray imagery for the determination of position and orientation (1002) of osteotomy location and scale and surgical tools. Algorithms (1006) are used to determine solutions including, but not limited to, location of osteotomy site, angle of cut, degree of correction, and assessment of results.

The method can be used for peri-acetabular osteotomy for acetabular dysplasia. The markers (e.g., 100, 108, 110, etc.) for anatomic landmarks and tools are used for data collection (1000), which may be combined with pre-operative CT scan data for the determination of position and orientation (1002) of osteotomy location and surgical tools. Algorithms (1006) are used to determine solutions including, but not limited to, location of osteotomy site, angulation, degree of correction, and assessment of results.

The method can be used for pediatric orthopedic osteotomies similar to the previous embodiments. The markers (e.g., 100, 108, 110, etc.) for anatomic landmarks and tools are used for data collection (1000), which may be combined with pre-operative CT scan data for the determination of position and orientation (1002) of osteotomy location and surgical tools. Algorithms (1006) are used to determine solutions including, but not limited to, location of osteotomy site, angle of cut, degree of correction, and assessment of results.

The method can be used for elbow ligament reconstructions including, but not limited to, radial collateral ligament reconstruction (RCL) and UCL reconstruction (Tommy-John). The markers (e.g., 100, 108, 110, etc.) for anatomic landmarks and tools are used for data collection (1000), which may be combined with pre-operative CT scan or MRI data for the determination of position and orientation (1002) of isometric points for ligament reconstruction and surgical tools. Algorithms (1006) are used to determine solutions including, but not limited to, precise localization of tunnel placement and assessment of results.

The method can be used for knee ligament reconstructions including, but not limited to, MCL, LCL, ACL, PCL and posterolateral corner reconstructions. The markers (e.g., 100, 108, 110, etc.) for anatomic landmarks and tools are used for data collection (1000), which may be combined with pre-operative CT scan or MRI data for the determination of position and orientation (1002) of isometric points for ligament reconstruction and surgical tools. Algorithms (1006) are used to determine solutions including, but not limited to, precise localization of tunnel placement, tunnel depth, tunnel angle, graft placement, and assessment of results.

The method can be used for ankle ligament reconstructions including, but not limited to, reconstruction to correct instability. The markers (e.g., 100, 108, 110, etc.) for anatomic landmarks and tools are used for data collection (1000), which may be combined with pre-operative CT scan or MRI data for the determination of position and orientation (1002) of isometric points for ligament reconstruction and surgical tools. Algorithms (1006) are used to determine solutions including, but not limited to, precise localization of tunnel placement, tunnel depth, tunnel angle, and assessment of results.

The method can be used for shoulder acromioclavicular (AC) joint reconstruction surgical procedures including, but not limited to, placement of tunnels in the clavicle. The markers (e.g., 100, 108, 110, etc.) for anatomic landmarks and tools are used for data collection (1000), which may be combined with pre-operative CT scan or MRI data for the determination of position and orientation (1002) of isometric points for ligament reconstruction and surgical tools. Algorithms (1006) are used to determine solutions including, but not limited to, precise localization of tunnel placement, tunnel depth, tunnel angle, and assessment of results.

The method can be used for anatomic and reverse total shoulder replacement (TSA and RSA) surgical procedures including revision TSA/RSA. The markers (e.g., 100, 108, 110, etc.) for anatomic landmarks and tools are used for data collection (1000), which may be combined with pre-operative CT scan or MRI data for the determination of position and orientation (1002) of humeral head, related landmarks, and surgical tools. Algorithms (1006) are used to determine solutions including, but not limited to, precise localization of humeral head cut and glenoid bone placement, baseplate and screws, and reaming angle and guide placement for glenoid correction, and assessment of results.

The method can be used for total ankle arthroplasty surgical procedures. The markers (e.g., 100, 108, 110, etc.) for anatomic landmarks and tools are used for data collection (1000), which may be combined with pre-operative CT scan or MM data for the determination of position and orientation (1002) of tibia, fibula, talus, navicular and other related landmarks and surgical tools. Algorithms (1006) are used to determine solutions including, but not limited to, precise localization of tibial head cut, anatomic axis determination, and assessment of results.

The method can be used for percutaneous screw placement for pelvic fractures, tibial plateau, acetabulum and pelvis, but not limited to these areas. The markers (e.g., 100, 108, 110, etc.) for anatomic landmarks and tools are used for data collection (1000), which may be combined with pre-operative CT scan or MRI data for the determination of position and orientation (1002) of anatomic and other related landmarks and surgical tools including screws. Algorithms (1006) are used to determine solutions including, but not limited to, precise localization of bones receiving screws, surrounding anatomy and soft tissue features to be avoided, localization of screws, angle of insertion (e.g., of an injection), depth of insertion (e.g., of an injection), and assessment of results.

The method can be used for in-office injections to areas including, but not limited to, ankle, knee, hip, shoulder, and spine. The markers (e.g., 100, 108, 110, etc.) for anatomic landmarks and tools are used for data collection (1000), which may be combined with pre-operative CT scan or MRI data for the determination of position and orientation (1002) of related landmarks and surgical tools. Algorithms (1006) are used to determine solutions including, but not limited to, precise localization of injection location, angulation, and depth in order to maximize effect and minimize interaction with internal organs and anatomy.

The method can be used for pedicle screw placement for spinal fusion procedures including the lumbar and thoracic spine, but not limited to these areas. The markers (e.g., 100, 108, 110, etc.) for anatomic landmarks and tools are used for data collection (1000), which may be combined with pre-operative CT scan or MM data for the determination of position and orientation (1002) of anatomic and other related landmarks and surgical tools including screws. Algorithms (1006) are used to determine solutions including, but not limited to, precise localization of bones receiving screws, opening of the cortex, cranial-caudal angulation or similar, medio-lateral inclination, screw insertion trajectory, depth of insertion, and assessment of results.

The method can be used for visualization of alternate spectrum imagery including, but not limited to, infrared, ultraviolet, ankle, knee, hip, shoulder, and spine. The markers (e.g., 100, 108, 110, etc.) for anatomic landmarks and tools are used for data collection (1000), which may include, but is not limited to, dual color camera(s) with alternate spectrum sensitivities and/or injection dye for highlight of the patient's features for the determination of position and orientation (1002) of related landmarks and surgical tools and position, location, and type of anatomic features more readily visible in alternate spectrums including nerves, tumors, soft tissues and arteries. Algorithms (1006) are used to determine solutions including, but not limited to, precise localization of nerves, tumors, soft tissues of interest, arteries and other features of interest that can be enhanced with this technique.

The method can be used for tumor diagnostic, staging, and curative surgical procedures. The markers (e.g., 100, 108, 110, etc.) for anatomic landmarks and tools are used for data collection (1000), which may be combined with pre-operative CT scan or MRI data for the determination of position and orientation (1002) of tumor location and surgical tools. Alternately during diagnostic surgery, localization of the tumor with respect to anatomic landmarks can be performed. Algorithms (1006) are used to determine solutions including, but not limited to, location of tumor site and size extent, removal guidance and assessment of results.

The method can be used for projection of a visible or invisible but camera visible point of light on objects of interest in the field of regard, including, but not limited to, bony landmarks, nerves, tumors, and other organic and inorganic objects. The markers (e.g., 100, 108, 110, etc.) are used to augment or supersede external data sets for anatomic data and can be used in place of a physical pointer or tool as has been described previously. The point of light can be displayed from the user's head display or other location. The point of light can also be manifested as a pattern or other array of lights. These light(s) highlight features on the patient for determination of position and orientation (1002) of related landmarks and surgical tools, as well as augmentation of data sets including, but not limited to, fluoroscopy, CT scans and MRI data. Algorithms (1006) are used to determine solutions previously described but with the alternate or added selection option.

The method can be used for minimally invasive positioning of implants and inserting locking screws percutaneously. A marker (e.g., 100, 108, or 110, etc.) is mounted on the proximal end of an intramedullary nail. Another marker (e.g., 100, 108, or 110, etc.) is mounted on the cross-screw insertion tool. A virtual model of the nail is displayed including the target trajectory for the locking cross-screw. The surgeon is able to insert the cross screw by aligning the virtual cross-screw with the target trajectory. In another embodiment, the same method can be applied to the external fixation plates. In this case, virtual locking plate with a plurality of locking screw trajectories, one for each hole, would be displayed.

The method can be used for visualization of ultrasound imaging data. In one application, the system can assist in guidance of needles during medical procedures, such as injection of anesthetic drugs. Ultrasound imaging can assist in needle visualization, but not until the needle enters the ultrasound field of view within the tissue, by which time its trajectory is already established and cannot be adjusted without causing pain to the patient. The system of the present invention can assist the user with tracking a needle both before and after insertion. Referring to FIGS. 10 and 31, a fiducial 3106 is mounted on an ultrasound transducer 3104. As the user 106 collects 2D images of an internal anatomy of a patient using the ultrasound transducer, the system 10 simultaneously tracks the position and orientation of the ultrasound transducer 3104 and receives the 2D ultrasound images 1004. The system 10 could, optionally and/or additionally, track patient 1900. The system 10 then combines the 2D images of the patient with the position and orientation of the ultrasound transducer 3104 relative to the patient; reconstructs the 2D images in a common reference frame using the acquired ultrasound transducer and patient position and orientation data; and displays the reconstructed images or 3D images to the user 106 in AR headset 3600. The system 10 can further use image analysis algorithms 1006 to generate and display surface or solid models 1008 created from anatomic structures identified in the imaging data. The system 10 can optionally display a virtual tool superimposed on the 3D imaging data based on the tracked position of one or more physical tools, such as a needle. Since the accuracy of the 3D reconstruction is subject to errors such as magnification discrepancies due to the speed of sound in various tissues, the relative position of a virtual tool may be imperfect. However, once the needle enters the ultrasound field of view, its positional accuracy is improved by direct visualization of the needle in the image. At this stage, the 3D reconstruction of the needle is valuable in determining the location of the needle tip, which is difficult to distinguish from a random cross-section in a standard 2D image. Knowing the location of the needle tip, not just its axis, assists the user in inserting the needle to the desired depth without causing injury to adjacent tissues. The system 10 continues to track a position and an orientation of a probe (e.g., needle, injection, pin, screw, etc.) and displays an axis (e.g., along an axial length of the probe) and/or location of the tip of the probe relative to the 3D image of the internal anatomy of the patient. The axis may be, for example, a virtual axis of the probe or a graphical representation of the probe. The tip of probe is then advanced to a desired position based on the location relative to the internal anatomy of the patient. Optionally, as shown in FIG. 31, an outer surface of the patient is mapped using stereo cameras and displayed in conjunction with the 3D images of the internal anatomy of the patient and/or ultrasound transducer 3104.

VIII. Database of Trackable Instruments and Equipment

Figure 29:
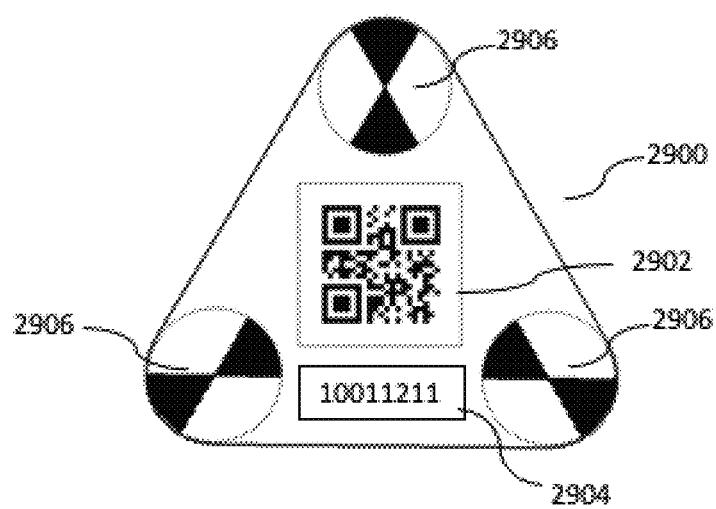
FIG. 29 shows a front view of a diagrammatic depiction of an equipment identification and tracking label that is optionally included in the system of FIG. 1.

The present invention optionally includes the construction of an electronic database of instruments and equipment in order to allow the AR headset 3600 to identify what instruments are present in the surgical field or in the operating room area. Referring to FIG. 29, a serialized tracking label 2900 is optionally included in the system to facilitate the construction of such database. The serialized tracking label 2900 includes a machine-readable serial number code 2902, a human readable serial number 2904, and a set of optical features which facilitate six-degree of freedom optical pose tracking such as a plurality of fiducials 2906. In one embodiment, the machine-readable number code 2902 pattern can be imaged by the camera(s) 3904 of the AR headset 3600 and used alone to determine pose and position of the medical instrument using machine vision algorithms. In another embodiment, the serial number image 2904 can be imaged by the camera(s) 3904 and used alone to determine pose and position of the medical instrument using machine vision algorithms. In yet another embodiment, the entire physical model of the tracking label 2900 can be imaged by the camera(s) 3904 and used alone to determine pose and position of the medical instrument using machine vision algorithms. In another embodiment, the tracking label 2900 may be comprised or contain a wireless RFID tag for non-optical identification of equipment in a kit that can be then verified automatically using optical recognition.

Figure 30:
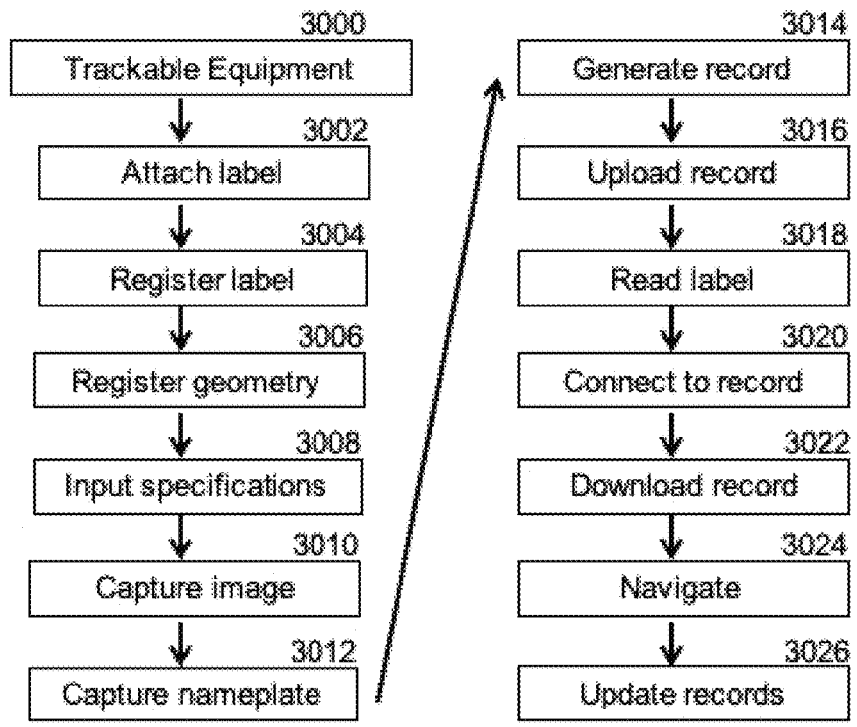
FIG. 30 is a flowchart of a method for registering, sharing, and/or tracking medical equipment using the system of FIG. 1 in accordance with the principles of the present invention

Referring to FIG. 30, a flowchart showing a system for registering item type and physical parameters of equipment and storing and sharing this data for use in surgery using an augmented reality headset is provided. In this exemplary embodiment, serialized trackable labels are pre-printed on durable self-adhesive material. The label is attached (3002) to an item of equipment (3000), which could be, but is not limited to, a C-arm, impactor, pointer, or any other equipment used in the procedure, in a location which will be most advantageously viewed during a surgical procedure or in the preparatory effort leading to the procedure (i.e. back table operations). The label is then registered (3004) by viewing with the camera(s) 3904, identifying the label, and initiating a database record associated with that serial number. Geometry of interest relating to the item of equipment can also be registered (3006) and stored relative to the trackable sticker. For example, in the case of a C-arm, a registration stylus may be used to register three points around the perimeter of the face of the imager and a point representing the origin of the X-ray beam source. This provides a coordinate frame, orientation (pose) data, and position data of the X-ray beam source with respect to the AR headset 3600 coordinate frame for use by the AR headset's 3600 algorithms. In one alternate embodiment, the cameras 3904 are stereo cameras and are used to scan and recognize C-arm geometry by recognition of key features such as the cylindrical or rectangular surface of the imager. Additional relevant specifications (3008) for the item of equipment can be entered into the record and includes, but is not limited to, the equipment type and model, calibration due date, electronic interface parameters, and wireless connectivity passwords. An image of the device is captured 3010 with the camera(s) 3904. An image of the equipment label (3012) of the device is captured. All these items are added to the completed record (3014), which is currently local to the AR headset 3600. The record is then time-stamped and shared with a central database (3016). This may be located on a local server within the hospital system or in any remote server including any cloud-based storage via the internet. Upload of the database may be done via Wi-Fi common network protocols or other art-disclosed means. The above actions may be performed by a company representative, a technician employed by the hospital, or any other trained individuals. To prevent poorly registered equipment entering the database, administrator privileges may be required to capture a record.

When an item of equipment is being used in surgery, the camera(s) 3904 are utilized to recognize the label as a trackable item of equipment and read the serial number (3018). The AR headset 3600 can then connect (3020) to the database and download the equipment record (3022). The equipment can thus be used in a six-degree of freedom trackable manner during the surgery (3024). If applicable, to the equipment with the data labels, the records (3026) may also be updated with data specific to the equipment itself, for example, upload images captured by the equipment during a surgery or capture logs of equipment activity during a surgery in a log. Log entries describing the use of the equipment in the surgery can be added to the database and to the patient record showing utilization of the equipment. The database thus generated can be mined for various reasons such as retrieving usage of defective equipment.

The system may also be used to recognize surgical instruments and implants encountered during surgery. A database of CAD models of instruments and equipment to scale is held in memory. During a procedure, SLAM or similar machine vision algorithms can capture topography of items in the scene and compare to the database on instruments and equipment. If a match is found, system can then take actions appropriate such as tracking the position and orientation of instruments relative to the patient and other instruments being used in surgery or enter a mode relevant to use of that instrument. For example, in a hip replacement procedure, if an acetabular impactor is detected, the mode for cup placement navigation is entered.

The system may also use its knowledge of the current software workflow steps to provide applicable instructions to OR staff, such as a scrub tech. Instructions may be displayed on a remote monitor or a second AR headset 3600 networked with the surgeon's system. For example, the system may display information about the next step coming in the workflow and instruct the scrub tech or assistant which instruments to prepare, optionally including pictures, video, or audio instructions for locating, identifying, or assembling the required instrumentation. The system's cameras could be used to identify specific instruments or instrument sets and indicate required instruments to an assistant and via an AR headset display. The surgeon or other experienced user could optionally input custom instructions to be displayed to assistants or staff for each step in a surgical workflow.

Figure 65:
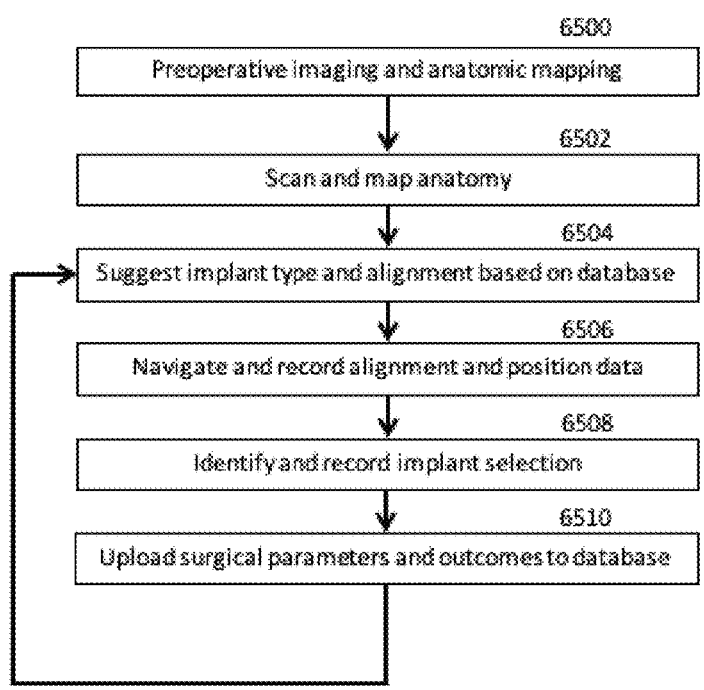
FIG. 65 is a flowchart showing an exemplary method of optimizing surgical parameters.

The system may also be used to optimize implant selection and/or placement based on outcomes data or common practice. FIG. 65 depicts a flowchart showing an exemplary method for using the system to assist in surgical decision-making. The system first scans and maps the native anatomy using sensor suite 210 (block 6502). Optionally, the anatomic data may be augmented or replaced by preoperative imaging such as CT or MRI. Then, comparing the anatomy to a database and identifying cases with similar anatomy, the system suggests implant types, alignment, and positioning of components (block 6504). The user 106 proceeds to navigate and complete the surgery as the system 10 records the actual alignment and positioning data (block 6506). The system 10 proceeds to record the implant type and size selected by the user 10, either by automated scanning with sensor suite 210, or with manual input (block 6508). The surgical data are uploaded to a database including surgical outcomes, if available (block 6510). The updated database is used to inform the next case at block 6504. Suggestions may be based on desired surgical outcomes, if available in the database, or based on common practice by the same user 106 or other users in similar situations. Other data may be collected intraoperatively, including data on procedure time and instrument usage. Sensor suite 2010 may use machine vision algorithms to automatically identify instruments during surgery and record which instruments are used in each procedure, as well as when instruments are used. Hospitals may use this information for efficiently packaging instrument sets to contain the most commonly used instruments, or for training or instructing staff on when in a procedure specific instruments are needed. Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

Unless stated otherwise, dimensions and geometries of the various structures depicted herein are not intended to be restrictive of the invention, and other dimensions or geometries are possible. Plural structural components can be provided by a single integrated structure. Alternatively, a single integrated structure might be divided into separate plural components. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention.

The systems and methods of the preferred embodiment and variations thereof can be embodied and/or implemented at least in part as a machine configured to receive a computer-readable medium storing computer-readable instructions. The instructions are preferably executed by computer-executable components preferably integrated with the system and one or more portions of the processor in the support module and/or a computing device. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific processor, but any suitable dedicated hardware or hardware/firmware combination can alternatively or additionally execute the instructions.

As used in the description and claims, the singular form "a", "an" and "the" include both singular and plural references unless the context clearly dictates otherwise. For example, the term "sensor" may include, and is contemplated to include, a plurality of sensors. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The invention claimed is:

1. A self-contained surgical navigation system configured for use with a helmet and a face shield, comprising:
   a head-worn display device to be worn by a user during surgery comprising:
      a display generator for generating a visual display on the display device,
      a sensor suite having at least one tracking camera,
      a visible light source,
      an infrared light source, and
   a processor unit configured to receive data from the sensor suite and calculate a position and an orientation of at least one marker; and
   a shroud comprising a plurality of sidewalls arranged around the infrared light source, wherein the plurality of sidewalls define an aperture through which light from the infrared light source is emitted,
   wherein the shroud, the at least one tracking camera, the visible light source, and the infrared light source are positioned behind a face shield when the head-worn display device is attached to a helmet, and
   wherein the plurality of sidewalls is in contact with the face shield when the head-worn display device is attached to the helmet such that light emitted by the infrared light source is prevented from being reflected into the at least one tracking camera and only passes through the face shield.

2. The system of claim 1, further comprising an infrared light filter coupled to the visible light source, such that the visible light source is prevented from emitting infrared light when the infrared light filter is coupled to the visible light source.

3. The system of claim 1, further comprising:
at least two markers affixed to one or more objects of interest for tracking the one or more objects of interest, wherein a first marker is within a field of view of the at least one tracking camera and a second marker is outside of the field of view of the at least one tracking camera,
wherein the processor unit is further configured to:
determine a position of the first marker within the field of view of the at least one tracking camera,
display a virtual guide to the user on the display device to direct the user to a position of the second marker relative to the first marker, and
determine the position of the second marker with the at least one tracking camera based on the direction from the virtual guide.

4. The system of claim 1, further comprising a support module comprising:
a user-replaceable, modular battery that is removably insertable into a housing of the support module, and
a processor unit configured to receive data from the sensor suite and calculate a position and an orientation of at least one marker,
wherein the support module is electrically coupled to the head-worn display device to provide power and data to the head-worn display device, and wherein the support module is worn on a body of the user on a location other than a head of the user, and
wherein the display device and the support module together comprise the entire sensing and computing capability of the system, without requiring external sensors, cameras, computers, or other electrical equipment.

5. The system of claim 1, wherein a front surface coupled to the plurality of sidewalls is in close proximity with the face shield and has a radius of curvature that approximately matches a radius of curvature of the face shield.

6. The system of claim 1, wherein one or more of the plurality of sidewalls is angled 10 to 20 degrees relative to a central axis of the infrared light source.

7. A self-contained surgical navigation system, comprising:
a head-worn display device to be worn by a user during surgery comprising:
a display generator for generating a visual display on the display device, and
a sensor suite having at least one tracking camera; and
a support module comprising:
a user-replaceable, modular battery that is removably insertable into a housing of the support module,
at least one marker affixed to an object of interest for tracking the object of interest, wherein the at least one marker is outside of a field of view of the at least one tracking camera, and
a processor unit configured to receive data from the sensor suite and calculate a position and an orientation of the at least one marker, wherein the processor unit is further configured to:
track an angle of the head of the user using one or more sensors of the sensor suite,
calculate a relative position of the at least one marker based on a last known position of the at least one marker when the at least one marker was positioned in the field of view of the at least one tracking camera, wherein the last known position is relative to the angle of the head, and
display a virtual guide to the user on the display device to direct the user to a position of the at least one marker,
wherein the support module is electrically coupled to the head-worn display device to provide power and data to the head-worn display device, and wherein the support module is worn on a body of the user on a location other than a head of the user, and
wherein the display device and the support module together comprise an entire sensing and computing capability of the system, without requiring external sensors, cameras, computers, or other electrical equipment.

8. The system of claim 7, further comprising one or more of: a face shield and a helmet, wherein the display device is mounted to the face shield or helmet.

9. The system of claim 8, wherein the head-worn display device further comprises an infrared light source.

10. The system of claim 9, wherein the head-worn display device further comprises a visible light source and an infrared light filter coupled to the visible light source, such that the visible light source is prevented from emitting infrared light when the infrared light filter is coupled to the visible light source.

11. The system of claim 9, further comprising a shroud comprising a plurality of sidewalls arranged around the infrared light source and defining an aperture through which light from the infrared light source is emitted,
wherein the shroud, the at least one tracking camera and the infrared light source are positioned behind a face shield when the head-worn display device is attached to a helmet, and
wherein the plurality of sidewalls is in close proximity with the face shield when the head-worn display device is attached to the helmet such that light emitted by the infrared light source is prevented from being reflected into the at least one tracking camera and only passes through the face shield.

12. The system of claim 7, wherein the processor unit is further configured to:
acquire an initial position of the first marker and the second marker; and
when the second marker is not in the field of view of the at least one tracking camera, estimate the position of the second marker relative to the first marker based on the acquired initial position.

13. The system of claim 7, wherein the processor unit is further configured to:
acquire an initial position of the first marker and the second marker relative to known anatomical landmarks;
calculate a distance between the known anatomical landmarks; and
when the second marker is not in the field of view of the at least one tracking camera, estimate the position of the second marker relative to the first marker based on the calculated distance.

14. The system of claim 7, wherein the processor unit is further configured to:

track a movement of the head of the user using one or more sensors in the sensor suite; and calculate the position of the second marker based on a last known position of the second marker when the second marker was within the field of view of the at least one tracking camera.

15. A self-contained, head-worn surgical navigation system, comprising:

a display generator for generating a visual display on a display device;

a sensor suite having at least one tracking camera;

at least two markers affixed to one or more objects of interest for tracking the one or more objects of interest; and a processor unit configured to:
receive data from the sensor suite and calculate a position of the at least two markers by:
projecting a virtual control into the user's field of view at a specific location relative to at least one marker,
displaying a user input control that is configured to be aligned with the virtual control based on user input,
setting a position of the virtual control such that, when the user turns its head to align the user input control with the virtual control, the at least two markers lie in the field of view of the at least one tracking camera,
activating the virtual control by aligning the user input control with the virtual control, and
tracking the at least two markers in the field of view of the at least one tracking camera.

16. A self-contained surgical navigation system, comprising:

a head-worn display device to be worn by a user during surgery comprising:
a display generator for generating a visual display on the display device, and
a sensor suite having at least one tracking camera; and a support module comprising:
a user-replaceable, modular battery that is removably insertable into a housing of the support module,
at least two markers affixed to one or more objects of interest for tracking the one or more objects of interest, wherein a first marker is within a field of view of the at least one tracking camera and a second marker is outside of the field of view of the at least one tracking camera, and
a processor unit configured to receive data from the sensor suite and calculate a position and an orientation of the at least two markers, wherein the processor unit is further configured to:
determine a position of the first marker within the field of view of the at least one tracking camera,
display a virtual guide to the user on the display device to direct the user to a position of the second marker relative to the first marker, and
determine the position of the second marker with the at least one tracking camera based on the direction from the virtual guide, wherein the support module is electrically coupled to the head-worn display device to provide power and data to the head-worn display device, and wherein the support module is worn on a body of the user on a location other than a head of the user, and wherein the display device and the support module together comprise an entire sensing and computing capability of the system, without requiring external sensors, cameras, computers, or other electrical equipment.

17. A self-contained surgical navigation system, comprising:

a head-worn display device to be worn by a user during surgery comprising:
a display generator for generating a visual display on the display device, and
a sensor suite having at least one tracking camera; and a support module comprising:
a user-replaceable, modular battery that is removably insertable into a housing of the support module,
at least two markers affixed to one or more objects of interest for tracking the one or more objects of interest, wherein one or both of the at least two markers is outside of the field of view of the at least one tracking camera, and
a processor unit configured to receive data from the sensor suite and calculate a position and an orientation of the at least two markers, wherein the processor unit is further configured to:
display a virtual control between the at least two markers;
display a user input control that is configured to be aligned with the virtual control based on user input;
adjust a position of the virtual control when the user turns its head to align the user input control with the virtual control; and
track the at least two markers in the field of view of the at least one tracking camera when the at least two markers are both in the field of view of the at least one tracking camera, wherein the support module is electrically coupled to the head-worn display device to provide power and data to the head-worn display device, and wherein the support module is worn on a body of the user on a location other than a head of the user, and wherein the display device and the support module together comprise an entire sensing and computing capability of the system, without requiring external sensors, cameras, computers, or other electrical equipment.

* * * * *